(12) United States Patent
Mathur et al.

(10) Patent No.: US 9,713,730 B2
(45) Date of Patent: Jul. 25, 2017

(54) APPARATUS AND METHOD FOR TREATMENT OF IN-STENT RESTENOSIS

(71) Applicant: Boston Scienitfic Scimed, Inc., Maple Grove, MN (US)

(72) Inventors: Prabodh Mathur, Laguna Niguel, CA (US); Meital Mazor, San Diego, CA (US); Dolores Perez, Escondido, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 532 days.

(21) Appl. No.: 13/644,367

(22) Filed: Oct. 4, 2012

(65) Prior Publication Data
US 2013/0282084 A1 Oct. 24, 2013

Related U.S. Application Data

(60) Provisional application No. 61/542,949, filed on Oct. 4, 2011.

(51) Int. Cl.
*A61B 18/14* (2006.01)
*A61N 5/00* (2006.01)
(Continued)

(52) U.S. Cl.
CPC ............ *A61N 5/00* (2013.01); *A61B 18/1492* (2013.01); *A61B 2018/00267* (2013.01);
(Continued)

(58) Field of Classification Search
CPC .. A61B 2018/0022; A61B 2018/00648; A61B 2018/00654; A61B 2018/124;
(Continued)

(56) References Cited

U.S. PATENT DOCUMENTS 164,184 A 6/1875 Kiddee
1,167,014 A 1/1916 O'Brien
(Continued)

FOREIGN PATENT DOCUMENTS

EP 1053720 A1 11/2000
EP 1180004 A1 2/2002
(Continued)

OTHER PUBLICATIONS

US 8,398,630, 03/2013, Demarais et al. (withdrawn)
(Continued)

*Primary Examiner* — Thomas Giuliani

(57) ABSTRACT

A catheter and catheter system can use energy tailored for remodeling and/or removal of target material proximate to a body lumen, often of stenotic material or tissue in the luminal wall of a blood vessel of a patient. An elongate flexible catheter body with a radially expandable structure may have a plurality of electrodes or other electrosurgical energy delivery surfaces to radially engage the luminal wall when the structure expands. Feedback using one or parameters of voltage, current, power, temperature, impedance magnitude, impedance phase angle, and frequency may be used to selectively control the delivery of energy.

29 Claims, 73 Drawing Sheets
(7 of 73 Drawing Sheet(s) Filed in Color)

(51) Int. Cl.
  *A61B 18/00* (2006.01)
  *A61B 18/12* (2006.01)
(52) U.S. Cl.
  CPC ............ *A61B 2018/00404* (2013.01); *A61B 2018/00779* (2013.01); *A61B 2018/00791* (2013.01); *A61B 2018/00827* (2013.01); *A61B 2018/00875* (2013.01); *A61B 2018/00892* (2013.01); *A61B 2018/124* (2013.01); *A61B 2018/1467* (2013.01)
(58) Field of Classification Search
  CPC .. A61B 2018/1467; A61B 2018/00404; A61B 18/1233
  USPC ...................... 606/41, 42; 607/113
  See application file for complete search history.

(56) References Cited

U.S. PATENT DOCUMENTS

| | | |
|---|---|---|
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |

(56) References Cited

U.S. PATENT DOCUMENTS

| | | |
|---|---|---|
| 5,601,526 A | 2/1997 | Chapelon et al. |
| 5,609,606 A | 3/1997 | O'Boyle et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy-Chutorian et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy-Chutorian et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |

(56) References Cited

U.S. PATENT DOCUMENTS

| | | |
|---|---|---|
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |

(56) References Cited

U.S. PATENT DOCUMENTS

| | | |
|---|---|---|
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Panescu et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |

(56) References Cited

U.S. PATENT DOCUMENTS

| | | |
|---|---|---|
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |

(56) References Cited

U.S. PATENT DOCUMENTS

| | | |
|---|---|---|
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |

(56) References Cited

U.S. PATENT DOCUMENTS

| | | |
|---|---|---|
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 * | 1/2013 | Stone et al. .................. 600/381 |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 8,939,970 B2 * | 1/2015 | Stone et al. .................. 606/41 |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0087208 A1 * | 7/2002 | Koblish et al. .............. 607/113 |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |

(56) References Cited

U.S. PATENT DOCUMENTS

| | | |
|---|---|---|
| 2002/0198520 A1 | 12/2002 | Coen et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |

(56) References Cited

U.S. PATENT DOCUMENTS

| | | |
|---|---|---|
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0168743 A1* | 7/2010 | Stone et al. ............... 606/42 |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0204560 A1* | 8/2010 | Salahieh ............... A61B 5/01 600/373 |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |

(56) References Cited

U.S. PATENT DOCUMENTS

| | | |
|---|---|---|
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1* | 4/2012 | Herscher et al. .......... 606/45 |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1* | 6/2012 | Steinke et al. .......... 606/33 |
| 2012/0157988 A1* | 6/2012 | Stone et al. .......... 606/33 |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramaniam et al. |
| 2013/0066316 A1* | 3/2013 | Steinke et al. .......... 606/41 |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |
| 2014/0180196 A1* | 6/2014 | Stone et al. .......... 604/21 |

FOREIGN PATENT DOCUMENTS

| | | |
|---|---|---|
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | 03026525 A1 | 4/2003 |
| WO | 2004100813 A2 | 11/2004 |
| WO | 2004110258 A2 | 12/2004 |
| WO | 2006105121 A2 | 10/2006 |
| WO | 2008014465 A2 | 1/2008 |
| WO | 2009121017 A1 | 10/2009 |
| WO | 2010067360 A2 | 6/2010 |
| WO | 2010102310 A2 | 9/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2013049601 A2 | 4/2013 |

OTHER PUBLICATIONS

Van Den Berg, "Light echoes image the human body," OLE, Oct. 2001, p. 35-37.

(56) References Cited

OTHER PUBLICATIONS

"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: LightLab Imaging Starts US Cardiology Clinical Investigations," LightLab Imaging Technology, 2002.
"Optical Coherencce Tomography: LightLab Sees Bright Prospects For Cardiac Application of OCT Technology," LightLab Imaging Technology, 2001, vol. 27, No. 35.
"Products—Functional Measurement," Volcano Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, an Antagonist of 5-HT(2A) Receptor, Treatment Reduces Restenosis After Coronary Stenting," American Heart Association, 2002.
Gabriel, "Appendix A: Experimental Data," 1999, p. 1-21.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.

Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Baun, "Interaction with Soft Tissue," Principles of General & Vascular Sonography, Chapter 2, pp. 23-24, Before Mar. 2012.

(56) References Cited

OTHER PUBLICATIONS

Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
Gabriel, "Appendix C: Modeling the frequency dependence of the dielectric properties to a 4 dispersions spectrum," p. 1-49, Nov. 6, 1997.
Han et al., "Third-Generation Cryosurgery for Primary and Recurrent Prostate Caner," BJU International, vol. 93, pp. 14-18, 2004.
Omura et al., "A Mild Acute Compression Induces Neurapraxia in Rat Sciatic Nerve," The International Journal of Neuroscience, vol. 114 (12), pp. 1561-1572, Dec. 2004.
"Optical Coherence Tomography: Advantages of OCT," LightLab Imaging Technology, printed Sep. 3, 2003.
"Optical Coherence Tomography: Image Gallery Cardiovascular Procedures," LightLab Imaging Technology, printed Sep. 3, 2003.
"Optical Coherence Tomography: What is OCT?," LightLab Imaging Technology, printed Sep. 3, 2003.
"Optical Coherence Tomography: Why Use OCT?," LightLab Imaging Technology, printed Sep. 3, 2003.
Popma et al., "Percutaneous Coronary and Valvular Intervention," Braunwald's Heart Disease: A Textbook of Cardiovascular Medicine, 7th edition, p. 1364-1405, 2005.

\* cited by examiner

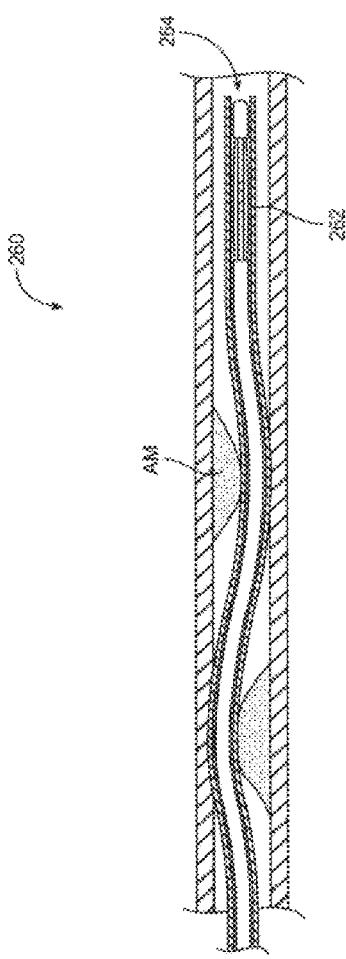

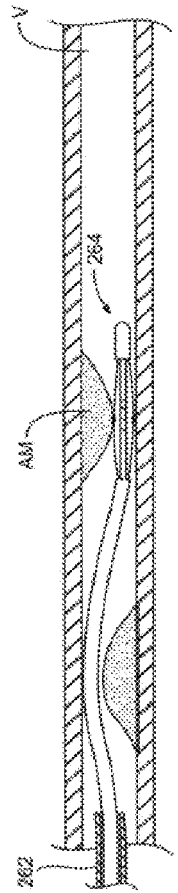
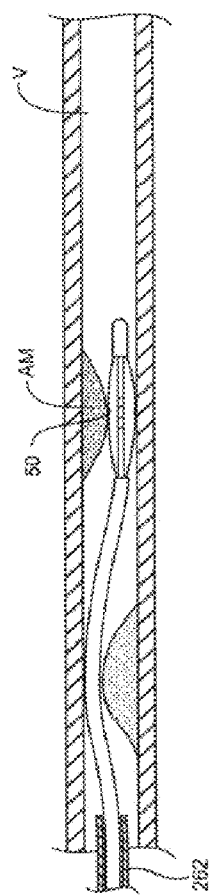
FIG. 14C
FIG. 14D

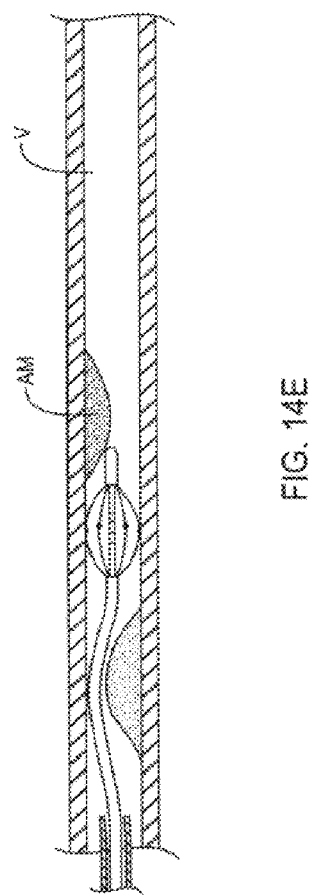

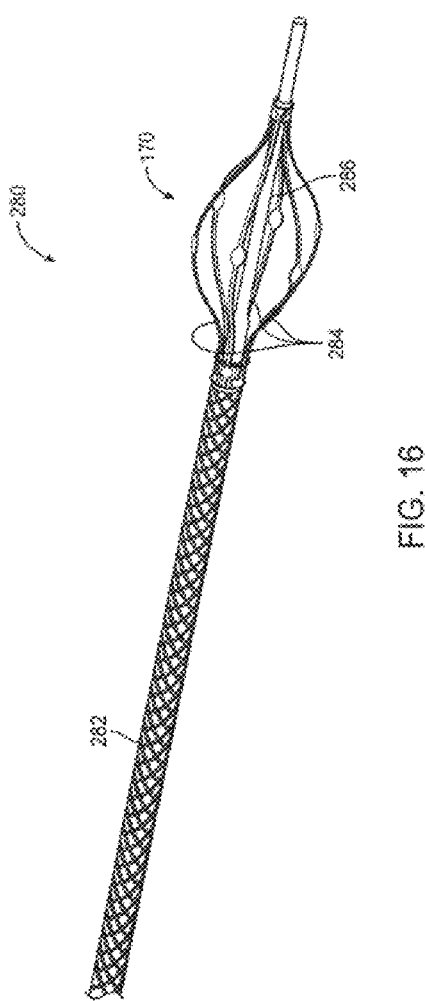

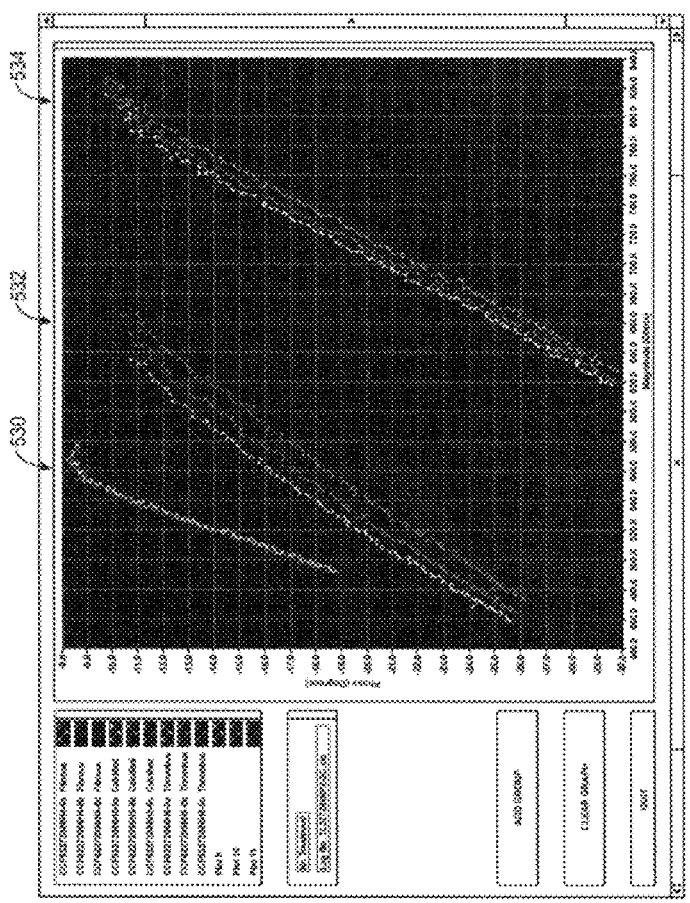

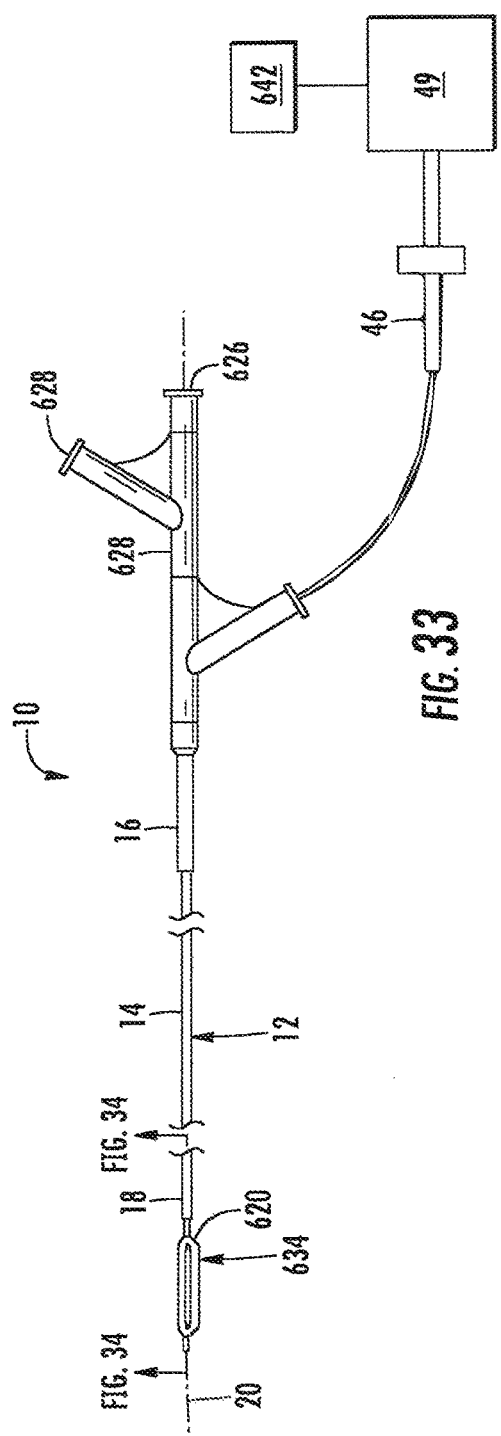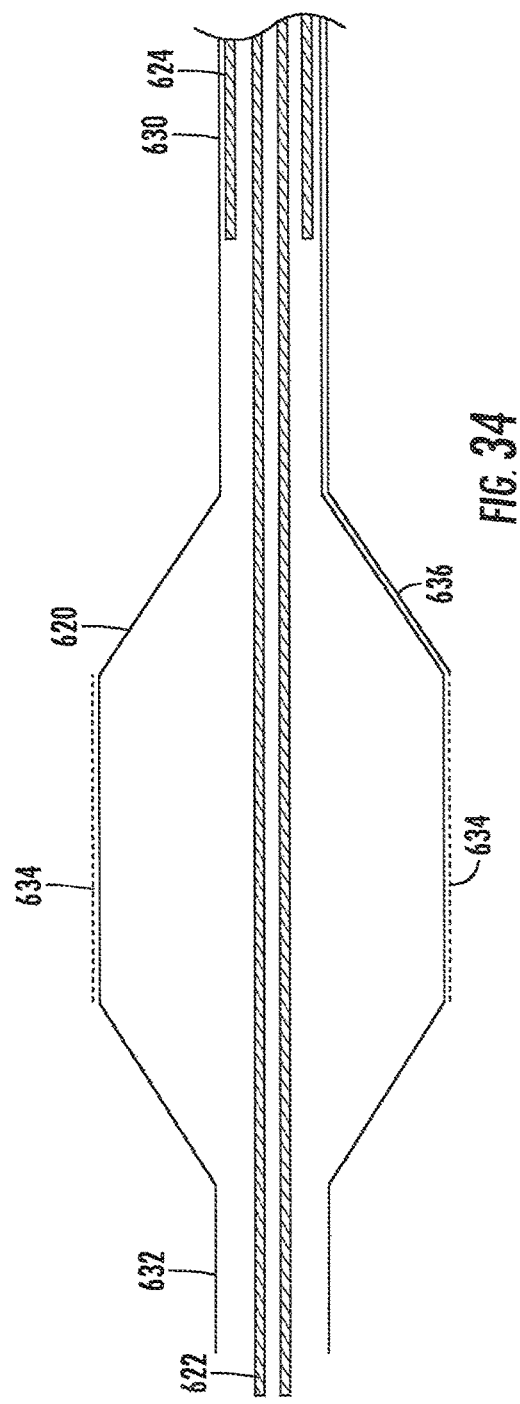

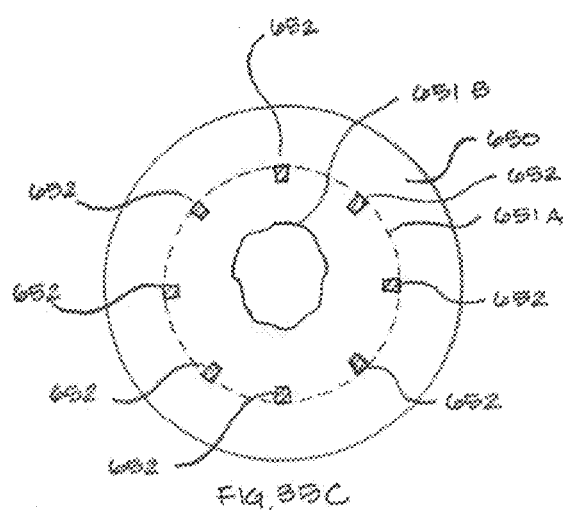

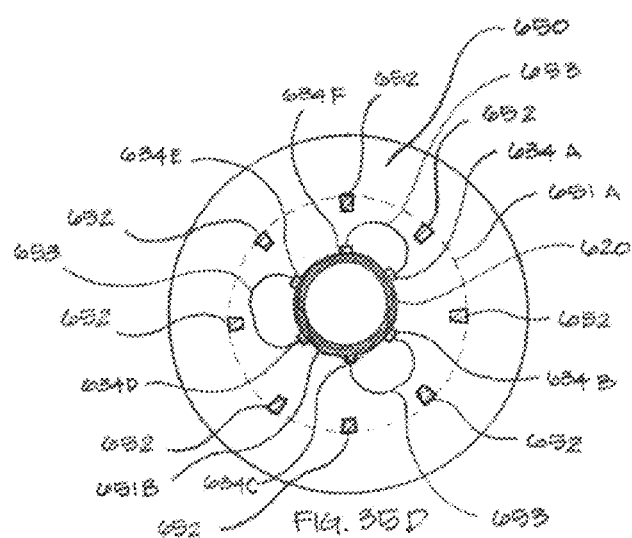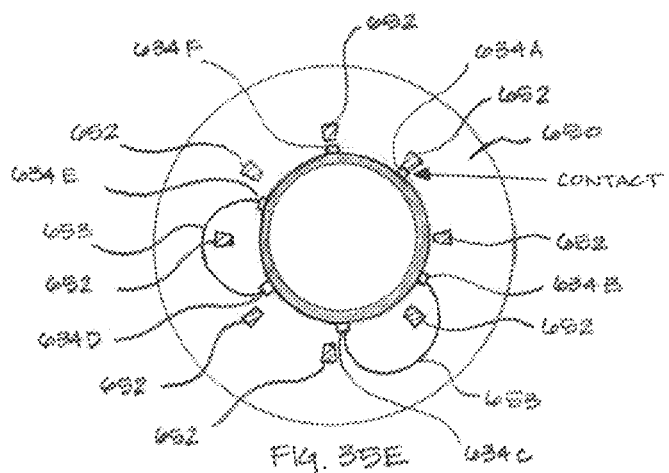

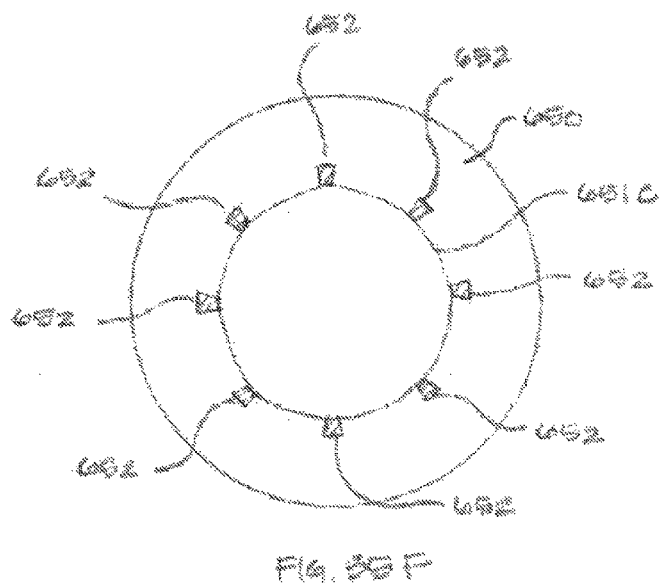

(2 Watts / 4 Seconds), 30 Day, 145b

Dose #5: (3 Watts / 2 Seconds), 7 Day,

APPARATUS AND METHOD FOR TREATMENT OF IN-STENT RESTENOSIS

CROSS-REFERENCES TO RELATED APPLICATIONS

The present application claims the benefit under 35 USC 119(e) of U.S. Provisional Application No. 61/542,949 filed Oct. 4, 2011. The full disclosure of which is incorporated herein by reference in its entirety for all purposes.

The present application is related to U.S. patent application Ser. No. 12/660,515 filed Feb. 26, 2010 (Allowed), entitled "Tuned RF Energy for Selective Treatment of Atheroma and Other Target Tissues"; U.S. patent application Ser. No. 11/392,231 filed Mar. 28, 2006 (now U.S. Pat. No. 7,742,795); entitled "Tuned RF Energy for Selective Treatment of Atheroma and Other Target Tissues, the full disclosures of which are incorporated herein by reference. The present application is related to U.S. patent application Ser. No. 10/938,138 filed on Sep. 10, 2004 (now U.S. Pat. No. 7,291,146), entitled "Selectable Eccentric Remodeling and/or Ablation of Atherosclerotic Material"; U.S. Provisional Application No. 60/852,787 filed on Oct. 18, 2006, entitled "Tuned RF Energy and Electrical Tissue Characterization For Selective Treatment Of Target Tissues"; U.S. Provisional Application No. 60/921,973 filed on Apr. 4, 2007, entitled "Tuned RF Energy and Electrical Tissue Characterization For Selective Treatment Of Target Tissues"; U.S. patent application Ser. No. 11/975,651 filed on Oct. 18, 2007, entitled "Tuned RF Energy and Electrical Tissue Characterization For Selective Treatment Of Target Tissues"; U.S. patent application Ser. No. 12/617,519 filed on Nov. 12, 2009 (Allowed), entitled "Selective Accumulation of Energy With or Without Knowledge of Tissue Topography"; U.S. patent application Ser. No. 11/975,474 filed on Oct. 18, 2007, entitled "Inducing Desirable Temperature Effects on Body Tissue"; U.S. patent application Ser. No. 11/975,383 filed on Oct. 18, 2007, entitled "System for Inducing Desirable Temperature Effects On Body Tissue"; U.S. patent application Ser. No. 12/616,720 filed on Nov. 13, 2009, entitled "Selective Drug Delivery in a Lumen"; U.S. application Ser. No. 12/564,268 filed on Sep. 22, 2009, entitled "Inducing Desirable Temperature Effects on Body Tissue Using Alternate Energy Sources"; and U.S. Provisional Application 61/177,744 filed on May 13, 2009, entitled "Directional Delivery of Energy and Bioactives", the full disclosures of which are incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

The present invention is generally related to medical devices, systems, and methods. In exemplary embodiments, the invention provides catheter-based treatment for body tissues, which may further include treatment for luminal tissues, particularly for vascular stenosis and/or for delivery of energy proximate to a luminal wall. The methods, systems, and structures of the invention allow controlled delivery of tissue treatment energy, tissue remodeling and/or removal, often using both electrical diagnostic and/or control signals and electrosurgical energy.

Physicians use catheters to gain access to and repair interior tissues of the body, particularly within the lumens of the body such as blood vessels. A variety of means are known in the art for providing localized therapeutic effects in the area surrounding the target location. For example, balloon angioplasty, atheterctomy, laser, cryogenic ablation, stents, and other catheter-based treatments of the like often are used to open arteries that have been narrowed due to disease.

Balloon angioplasty is often effective at opening a stenosed blood vessel, but the trauma associated with balloon dilation can impose significant injury, so that the benefits of balloon dilation may be limited in time. Stents are commonly used to extend the beneficial opening of the blood vessel.

Stenting, in conjunction with balloon dilation, is often the preferred treatment for stenotic disease such as atherosclerosis. In stenting, a collapsed metal framework is mounted on a balloon catheter that is introduced into the body. The stent is manipulated into the site of stenosis and expanded in place by the dilation of the underlying balloon. Stenting has gained widespread acceptance, and produces generally acceptable results in many cases. Along with treatment of blood vessels (particularly the coronary arteries), stents can also be used in treating many other tubular obstructions within the body, such as for treatment of reproductive, gastrointestinal, and pulmonary obstructions.

Restenosis occurs when the treated vessel becomes re-blocked following its initial interventional treatment. It usually occurs within six months after the initial procedure. The mechanism of restenosis after balloon angioplasty is a combination of recoil, arterial vessel remodeling, and neointimal hyperplasia. Late lumen loss in stented segments is the result of intimal hyperplasia. Compared with balloon angioplasty alone, where the chance of restenosis may, for example, be estimated to be about 40%, stents have been shown to reduce the chance of restenosis in some cases to about 25%. Therefore, the majority of patients having angioplasty today are treated with stents. Restenosis can occur after the use of stents, and physicians refer to this as in-stent restenosis, which is typically seen three to six months after the stenting procedure. Several approaches have been developed to treat restenosis including ablation, atheroectomy, and drug eluting stents. In addition, work has also been initiated with systemic drug delivery (intravenous or oral) that may also improve procedural success rates. The existing available options for treatment of in-stent restenosis may have limitations such as procedural complexity, constraints caused by the pre-existing implant, limitations in long-term efficacy, extremely high product development costs and protracted regulatory pathways, costly medication regimens, and the challenges of vascular biomechanics in places such as the leg.

In-stent restenosis involves the growth of new tissue within the arterial wall, and may be caused by a biological cascade mechanism of platelets, polymorphonuclear leucocytes, and macrophage aggregation leading to the migration of smooth muscle cells from the media to the intima coupled with smooth muscle cell proliferation at the intimal layer.

The acute onset of in-stent restenosis can begin with relocation of plaque and reorganization of thrombus, in conjunction with an acute inflammatory response to injury of the endothelium that promotes fibrin and platelet deposition. Leucocytes gather in and around the injury caused by balloon dilation and stent implantation. As the biological cascade continues, leucocyte recruitment is further sustained.

As the in-stent restenosis process continues, smooth muscle cells in the medial layer modify and migrate from the medial layer to the intimal layer before further proliferating as neointimal tissue. The volume of stenotic neointimal tissue is increased by smooth muscle cell synthesis of extracellular matrix predominantly comprised of proteoglycans and collagens.

None of the available interventional modalities provides optimal acute results, and long-term results can be poor. This is especially true for diffuse in-stent restenosis lesions, which are common. For example, treatment of a diffuse, long, coronary artery lesion with overlapping bare metal stents has been known to be associated with high rates of restenosis. By way of example, drug eluting stents were thought to be a revolutionary method of significant and sustained suppression of neointimal proliferation in cases of diffuse, long coronary lesions requiring overlapping stents. However, hypersensitivity reactions or cytotoxicity have been shown to be serious problems with stents coated with an antiproliferative drug. Nebeker, et al. have recently published data suggesting that the window of thrombotic risk associated with drug eluting stents extends far beyond that seen with bare metal stents, thus, post-operative anti-platelet therapy may be requisite for drug eluting stent patients (J Am Coll Cardiol (2006), 47: 175-181), the full contents of which are incorporated herein by reference. Furthermore, United States Food and Drug Administration reports and autopsy findings suggest that drug eluting stents may be a cause of systemic and intra-stent hypersensitivity reactions that, in some cases, have been associated with late thrombosis and death. This hypersensitivity or cytotoxicity, possibly induced by the coating comprising the drug carrier, is associated with delayed healing and poor endothelialization (Virmani, et al., Coron Artery Dis (2004), 15: 313-318.), the full contents of which are incorporated herein by reference.

The application of energy to tissue has been shown to promote beneficial therapeutic responses, including for the treatment of tissue in or proximate to a body lumen. For example, thermal energy in controlled dosages may play a role in tissue debulking after thermal therapy by activation of Heat Shock Proteins (HSP's). HSP's are proteins that exist in most living cells (i.e. mammals, plants, and yeast). They often act like "chaperones" to ensure that a cell's normal functional proteins are in the right place at the right time. Their concentrations can increase in response to stress, such as heat, cold or lack of oxygen. Their increased presence can be a signal to the immune system for sick or necrotic cells that require removal, and therefore play a role in tissue debulking after a thermal treatment. Beneficial thermally-induced tissue effects have been disclosed by U.S. patent application Ser. No. 11/975,474 the full disclosure of which is incorporated herein by reference.

The application of energy to tissue proximate to an energy source is not limited to inducing tissue debulking. For example, radiofrequency energy may be used to affect energy conduction in nervous tissue in the fields of electrophysiology and neuromodulation; common examples include cardiac ablation to regulate heartbeat, neuromodulation to affect an expansive array of efferent and afferent nerve activity in physiologic processes such as those of the brain, digestive system, excretory processes, kidney and other organ function, sensory function, and the like.

In the example of thermal treatment of nerve tissue, such treatments may be ablative or non-ablative, wherein ablation causes long-term tissue damage while non-ablative energy may be in the form of stimulation or disruption of nerve conduction. The disruption of nerve conduction may be achieved by means that block or interfere with the transmission of nerve signals, which may for example be accomplished by means that change the nature of nerve tissue properties. The duration and extent of disruption may be tailored to the particular biologic process and may be a function of the energy dosage applied to the target site.

In the example of in-stent restenosis, a controlled application of radiofrequency energy may be used to cause resistive heating, and as a result the hydrogen bonds of the collagen contained in the tissue may be broken. This breaking of bonds may result in a more compliant stenosis that may be made to reshape around a balloon catheter while applying low pressure to the vessel wall (6 or less atmospheres) as opposed to the relatively high pressure (about 10-15 atmosphere) typical of regular balloon angioplasty. Thereby, this may facilitate restenotic tissue compression by the balloon and may result in a larger vessel lumen. In addition, Brasselet et al. have reported that moderate heating represents a promising approach to reduced neointimal hyperplasia by a mechanism involving decreased smooth muscle cell proliferation (Eur Heart J. (2008) 29(3):402-12), the full contents of which are incorporated herein by reference.

In light of the above, it would be advantageous to provide new devices, systems, and methods for diagnosing, characterizing, remodeling, and/or delivering therapeutic energy to tissues, which may further include stenosis of the lumens of the body, and particularly of the blood vessels. Specifically, it would be desirable to provide devices, systems, and methods for treating in-stent restenosis or energy delivery to other tissues proximate to a lumen where the delivery of energy in the form of a controlled dosage provides a means for interrupting biological activity. It would further be desirable to avoid significant cost or complexity while providing structures that could both characterize and remodel or remove target tissues such as plaques or other stenotic materials, nerve tissue, or other tissues such tissues found proximate to a lumen. It is further advantageous to avoid having to resort to the trauma known to be associated with dilation, excessive input of thermal energy to tissue, and the like, which may lead to chronic inflammatory response. It would also be beneficial if diagnosing and treating systems could provide some feedback on the progress of treatment.

BRIEF SUMMARY OF THE INVENTION

The present invention generally provides improved devices, systems, and methods for treating tissues proximate to a body lumen, including diseases of body lumens. Embodiments of the invention may allow treatment and/or analysis of the materials along these body lumens, optionally allowing target tissues such as nerve tissue, plaques, in-stent restenosis, or other lesions to be characterized using a variable frequency electrical power or signal source. Tissues may be locally treated by radially expanding an electrode array-supporting structure within (for example) a blood vessel. Further, circuits formed using selected electrodes of the array may be used for monitoring temperature and/or electrical characteristics (such as characteristic frequency, impedance phase angle, and impedance magnitude) of tissues along and adjacent to the blood vessel, so as to deliver a desired treatment to a targeted tissue region while avoiding significant thermal alteration of collateral tissues. Optionally, the same electrodes may be used to selectively (and often eccentrically) treat targeted tissues.

Embodiments of the invention may employ electrical energy to selectively heat target tissues and/or other body structures. For example, the electrical energy waveforms, application cycles, potentials, delivery systems, and the like may be tailored to help direct therapeutic energy into target tissues of the vasculature while inhibiting injury to collateral tissue structures. Tailoring may improve the efficacy of luminal therapies, may decrease collateral tissue damage, and in the case of in-stent restenosis, provide a means for delivering energy to stenotic material while avoiding electrical grounding caused by direct contact with an implanted stent.

For the treatment of in-stent restenosis, the ability to selectively energize electrodes based on temperature and/or electrical characteristics proximate to the points of an electrode array, in conjunction with monitoring changes in characteristics, may allow for a controlled delivery of energy. Furthermore, monitoring changes in electrical characteristics may provide the ability to halt energy delivery as an electrode comes into proximity or direct contact with the previously implanted stent while allowing energy delivery to continue in other circumferential locations where stenosis may remain present, until a substantially uniform recanalization of the restenosis occurs. Exemplary treatment systems and methods for physical targeting (for example, axial and/or radial targeting of occlusive tissues from within a blood vessel) and/or frequency targeting may make use of target tissue or disease localization information (for example, from intravascular imaging, or impedance measurement) and may optionally employ cooling to protect at least some tissues along a luminal wall.

In a first aspect, the invention provides an energy delivery catheter system for energy delivery for such purposes as remodeling and/or reduction of material of, or adjacent to, a body lumen of a patient. The system comprises an elongate flexible catheter body having a proximal end and a distal end with an axis there between. At least one energy delivery surface, preferably comprised to include an electrode, is disposed near the distal end. A power source is electrically coupled to the energy delivery surface(s). The power source energizes the energy delivery surface(s) with an electrical energy form that helps the energy heat the target material while inhibiting collateral tissue damage.

In another aspect, the invention provides a method and system for analyzing a vessel wall of a blood vessel. The method comprises engaging the vessel wall with an electrode of a probe (most preferably comprised of an expanding structure), and energizing the electrode with a variable frequency power source. The frequency of the power source is varied, and a target location of the vessel wall is characterized by monitoring a frequency-dependent characteristic of an electrical circuit. The electrical circuit comprises the power source, the electrode, and the engaged vessel wall. The system comprises a vascular probe having a proximal end, a distal end, and at least one electrode disposed near the distal end for engaging the vessel wall. A variable frequency power source may be coupled to the electrode such that, when the electrode engages the vessel wall, an electrical circuit (including the power source, the electrode, and the engaged vessel wall) may be established. A processor may be coupled with the variable frequency power source, the processor configured to control energy delivery to one or more target treatment zones of the vessel wall by monitoring a frequency-dependent characteristic of the electrical circuit.

Optionally, the probe expands radially within the blood vessel so as to engage a plurality of electrodes against the vessel wall. The electrodes of the expanded probe may generally define a circumferentially distributed electrode array, and the electrodes of the array may be supported by the associated expandable structure of the probe. The expandable structure may comprise a balloon, or alternately an expandable basket having struts that may expand resiliently and independently within the blood vessel so as to couple the array to the vessel wall within non-circular lumens. An eccentric subset of the array, optionally a single electrode or a pair of electrodes adjacent the target tissue, may be energized to characterize tissues locally, and/or to eccentrically treat the characterized target tissue using a remodeling electrical potential. Feedback on the remodeling may be obtained by monitoring temperature and/or one or more characteristics of the electrical circuit while applying a variable-frequency signal, either during remodeling or by halting remodeling at least temporarily.

In exemplary embodiments, characterized target tissue may comprise a stenotic portion of a blood vessel, and the remodeling may be halted in response to temperature and/or the electrical characteristics of the circuit. For example, the remodeling may be halted in response to a change in a tissue signature signal, such as an impedance phase angle and magnitude at a selected frequency or range of frequencies, that may be related to a tissue temperature, actual or impending electrical contact with the metallic body of a stent, or the like. Target tissue may be characterized using tissue signature and/or tissue signature profiles, with the signature profiles comprising curves or sets of data representing a plurality of tissue signature measurements at different frequencies throughout a frequency range. The target tissue may be characterized by comparison of a measured tissue signature profile to at least one other tissue signature profile, and may allow for an eccentric selection of electrodes about the circumference of lumen. Some embodiments may allow differentiation between an implant or other inorganic object, targeted tissue and other tissues that have not been treated, optionally by checking changes of a subset of the tissue signature measurements of the signature profiles. Tissue signature profiles may be normalized and/or benchmarked to a known tissue of the patient (such as a healthy tissue identified using intravascular ultrasound or other known techniques). Target tissues may be characterized using relative slopes of tissue signature profiles or offsets between tissue signature profiles (and preferably both). The frequency range of the profiles will often extend below 50 KHz, typically extending from below about 50 KHz to over 1 MHz, and in some embodiments extending from about 4 Hz to about 2 MHz.

Many embodiments will be suitable for treating or characterizing a plurality of localized materials distributed about the blood vessel or proximate to the wall of the blood vessel at a depth as deep as 5 mm or more, and optionally for selectively treating the characterized materials with different remodeling treatments using the electrodes.

In many embodiments, gentle heating energy added before, during, and/or after dilation of a blood vessel may increase dilation effectiveness while lowering complications. Benefits of the heating may be enhanced (and/or complications inhibited) by limiting heating of the adventitial layer below a deleterious response threshold. In many cases, such heating of the intima and/or media may be provided using heating times of less than about 180 seconds, often being less than 60 seconds, and sometimes 10 seconds or less. Power may range from less than 0.5 Watts to 20 Watts or more. In some cases higher power may be used for shorter periods of time, while in other cases, very low power may be used for longer durations. Efficient coupling of the energy to the target tissue by matching the driving potential of the circuit to the target tissue phase angle may enhance desirable heating efficiency, effectively maximizing the area under the electrical power curve. The matching of the phase angle need not be absolute, and while complete phase matching to a characterized target tissue may have benefits, alternative systems may pre-set appropriate potentials to substantially match typical target tissues; though the actual phase angles may not be matched precisely, heating localization within the target tissues may be significantly better than using a standard power form.

In many embodiments, electrodes may be energized using closed loop control. Most typically the power generator may be controlled to vary voltage or electrode firing time such that a controlled output is held substantially constant; alternately current may be varied. Further, control loop parameters may be selected from one or more of power, impedance, impedance phase angle, and temperature. Power generation and control that may be used in combination with the embodiments described herein has been described by U.S. Patent Application 61/342,191, entitled "Power Generating and Control Apparatus for the Treatment of Tissue", the full disclosure of which is incorporated herein by reference.

In embodiments where power is used as a regulated parameter, voltage and current may be measured and voltage may be modulated to achieve a relatively constant power output within a tolerance according to a preset or defined power set point. Optionally the phase angle difference between voltage and current may be included in the power calculation to make power factor corrections based on the phase angle difference.

In embodiments where impedance is used as a regulated parameter, measured changes in impedance or impedance phase angle based on changes in tissue temperature and/or tissue state may be used to define a threshold at which power may be halted or allowed to continue where power is modulated to maintain the defined impedance or phase angle within a tolerance for a period of time.

In embodiments where temperature is used as a regulated parameter, a temperature sensor comprised of a thermocouple, thermistor, infrared sensor, or the like, may be used to measure temperature where a defined temperature or temperature range may be used in conjunction with power modulation to maintain temperature in proximity to the sensor within a temperature range. In some embodiments, a relatively uniform temperature in the region proximate to a powered electrode may be achieved by establishing a reference voltage and varying the firing time of one or more electrodes such that electrodes are fired to reach a temperature and then hold the temperature through the control of the duty cycle of the power to each electrode. Power control schemes may calculate the power requirements of the electrode having the greatest draw and then modulate firing time for electrodes having a lesser power draw over a given time interval (most often being small fractions of a second).

In some embodiments, more than one of voltage, current, impedance, and temperature may be used as closed loop control parameters. For example, current may be a closed loop control parameter where power is delivered in the proximity of highly conductive materials, such as metallic stents. In this case it may be prudent to limit current, such as by stopping power delivery when the impedance is at or below a given level. Or, in the case of a power-limited control algorithm (which will increase current when impedance drops) one may additionally limit the maximum current that is delivered at or below a given impedance level. This method has the effect of reducing power as impedance falls below a given threshold. Optionally, some embodiments may employ one or both of pulse width modulation of energy, and amplitude modulation of energy as a means of control.

In embodiments where energy is delivered to a plurality of electrodes at the same time, electrodes may be powered and controlled either by separate, independent circuits having their own control loops, or by firing these electrodes sequentially. Electrodes may be fired simultaneously, in subgroups fired in sequence, in combinations, or individually in any sequence. For instance, electrode combinations may be chosen so as to minimize the space between treatment zones, where treatment zones may be defined by the tissue volume between paired electrodes. For example, an in-stent restenosis may require energy delivery around the full circumference of a lumen but the open portion of the lumen may not be concentric with the natural center of the healthy vessel. In this circumstance, individual pairs of bipolar electrodes may be energized and controlled until a desired temperature is reached or until proximity to the implanted stent is reached. Electrode pairs may optionally be selected again, so as to fill in the gaps between the first tissue treatment zones, and the controlled delivery of energy may be repeated such that essentially the full circumference of the lumen receives treatment. In a preferred embodiment for treating in-stent restenosis, electrode pairs are energized sequentially to create a first pattern of treatment zones. Electrode pairs next to be energized are then indexed so as to create a second pattern of treatment zones, with at least some degree of overlap with the first treatment zones, and then energized sequentially to complete the energy treatment dosage to be used.

Tissue treatment may involve the application of energy, typically in the form of radiofrequency, microwave and/or ultrasound energy to electrodes. This energy will be controlled so as to limit a temperature of target and/or collateral tissues proximate to a luminal wall, for example, so as to limit the heating of an in-stent restenosis of the intimal layer of an artery structure. In some embodiments, the surface temperature range is from about 50° C. to about 90° C. For gentle heating, the surface temperature may range from about 50° C. to about 75° C., while for more aggressive heating, the surface temperature may range from about 75° C. to about 90° C. Limiting heating of a target tissue to less than a surface temperature in a range from about 50° C. to about 75° C., such that the bulk tissue temperature remains mostly below 50° C.-55° C., may inhibit an immune response that might otherwise lead to stenosis. For example, relatively mild surface temperatures between about 50° C. and about 75° C., and most preferably between about 50° C. and about 65° C., may be sufficient to denature and break protein bonds during treatment, immediately after treatment, and/or more than one hour, more than one day, more than one week, or even more than one month after the treatment through a healing response of the tissue to the treatment so as to provide a bigger vessel lumen and improved blood flow.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 14A-E are cross sectional side views through a body lumen showing additional aspects of treatment methods and devices described herein.

FIG. 16 is a perspective view of an exemplary catheter assembly.

FIGS. 31A-J graphically illustrate relationships between phase angles and impedance in a frequency range as can be used to electrically analyze and characterize materials engaging and disposed between electrodes of the system of FIG. 2.

FIG. 33 schematically illustrates an alternate embodiment of the system of FIG. 2, wherein the expanding structure comprises a balloon.

FIG. 34 is a sectional view of the balloon of FIG. 33.

FIG. 35C is a cross sectional view of the body lumen of FIGS. 35A-35B with the subsequent development of in-stent restenosis.

FIG. 35D-35F are cross sectional schematic representations of the system of FIG. 33 positioned for use in, and treatment of, the body lumen of FIG. 35C.

DETAILED DESCRIPTION OF THE INVENTION

Figure 1A:
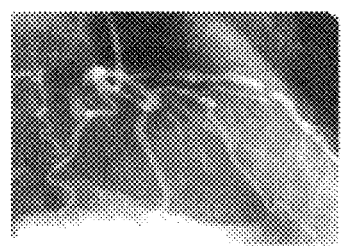
FIG. 1A illustrates diffuse atherosclerotic disease in which a substantial length of multiple blood vessels has limited effective diameters.

The present invention provides devices, systems, and methods to treat and/or analyze luminal tissue or tissues proximate to a lumen. The anatomical structure into which the catheter is placed may be, for example, the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the kidney, the liver, the ureter, the ejaculatory duct, the vas deferens, the urethra, the uterine cavity, the vaginal canal, and the cervical canal. The invention will be particularly useful for characterizing and treating materials along an artery, such as to open the artery lumen and increase blood flow, further including stenosis developed as a result of prior stent implantation. Remodeling may involve the application of electrosurgical energy, typically in the form of radiofrequency, laser, microwave, or ultrasound energy potentials to energy delivery surfaces such as electrodes, antennas, and other such energy delivery structures. This energy will preferably be controlled so as to limit a temperature of target and/or collateral tissues, for example, limiting the heating of healthy tissue collateral to the target tissue. In many embodiments, the energy will be controlled to limit the maximum temperature of an outer layer or adventitia of the blood vessel to no more than about 65° C. Inhibiting heating of non-target tissues (such as an intimal layer adjacent to an in-stent restenosis) may inhibit an immune response that might otherwise lead to further restenosis. Many embodiments may apply sufficient energy to target tissues to cause heating to as much as about 85° C. or more while inhibiting collateral damage through selective application of heating energy. Relatively mild heating energies may be sufficient to denature and shrink stenotic material during treatment, immediately after treatment, and/or more than one hour, or even more than one month after the treatment through a healing response to the treatment so as to provide a bigger vessel lumen and improved blood flow.

Smooth muscle contraction may be avoided, without actually killing or ablating it, by heating the smooth muscle to 47-48° C. The actin and myosin proteins become denatured but vital oxidative metabolic enzymes remain intact. This can promote luminal dilation or at minimum, prevent constriction (i.e. angioplasty balloon expansion vessel recoil or vasospasms often linked as a contributor to acute anginal attacks). Also, thermal energy must be low enough to prevent "thermal fixation", where tissue is "fixed" analogous to formalin fixation that prevents a desired immune-system-activated tissue debulking. As a general guide to tissue-temperature effects, below is a list of tissue temperature correlations that fall within the 2-10 second duration range at a given temperature:

42° C.=protein denaturation
41°-44° C.=DNA susceptibility
43° C.=spontaneous depolarizations
45° C.=mitochondrial breakdown
47.5° C.=contractile protein breakdown
48° C.=depolarization incapable
50° C.=blood cells become amorphous
50° C.=intracellular toxicity
50° C.=irreversible cell death
>50° C.=oncosis Inducing a therapeutic temperature with radiofrequency energy for even a second can result in a longer duration of elevated temperatures due to the built-up heat that continues to thermally diffuse into surrounding tissue. Irreversible cell death temperatures are suggested above but in reality comprise a wide range of temperatures capable of such effect. These temperatures can mathematically be described by a "line-fit" algorithm of $y=0.011x+55.01$, whereas the y-axis is temperature in (° C.) and the x-axis is in time in (sec). This demonstrates irreversible cell death as a relationship of temperature vs. time with the above described slope starting from 55° C. at 1 second to 45° C. at 1000 seconds. At temperatures higher than 55° C., time for cell death is too short to be effectively measured, and below 45° C. the time required is too long to be useful. Excessive or uncontrolled application of tissue temperatures above 60° C. become capable of immediate tissue debulking but may render healthy vessel tissue stenosed, charred, perforated or vaporized. Examples of these tissue-temperature effects are:

72°-86° C.=type 1 collagen breakdown
85° C.=blood coagulation/clumping
82-96° C.=type 3 collagen breakdown 100° C.=intracellular/interstitial fluid phase change—"popping">100° C.=tissue desiccation 100°-200° C.=tissue glucose sticks to electrode >200° C.=rapid vaporization/cell explosions (cutting), carbonization Thermal therapy may cause the activation of heat shock proteins that aid in tissue debulking Heat shock proteins exist in most living cells to ensure that a cell's normal functional proteins are in the right place at the right time. Their concentrations can increase in response to stress, such as heat, cold, or lack of oxygen. Their increased presence can be a signal to the immune system for the presence of sick or necrotic cells that require removal, and therefore play a role in tissue debulking after a thermal treatment. A controlled delivery of energy that activates heat shock proteins, but that avoids applying energy sufficient to cause undesirable tissue damage, may provide an effective means for delivering therapeutic effects for tissues proximate to a luminal wall. This biological response may be particularly advantageous for the treatment of in-stent restenosis where an acute response to thermal energy may be used to debulk hyperplastic stenotic tissue growth, that itself was the product of a chronic inflammatory response to dilation and or the presence of a stent, while avoiding thermal damage that may result in further restenosis. Hence, energy treatment of tissues proximate to a lumen may comprise gentle heating, removal, denaturing, shrinkage, melting, and the like, of the target tissues. Optionally, targeted material within the layers of an artery may be denatured so as to improve blood flow or to interrupt biological functioning while avoiding the generation of debris or lesions that may subsequently cause occlusion due to tissue damage. A bipolar electrode configuration is the most preferred method of implementation in order to better control the flow of energy to selectively treat tissues proximate to the luminal wall.

Embodiments of the present invention will often provide electrosurgical capabilities, sensing or imaging suitable for measuring stenosis, atheroma and/or vascular walls. As stenosis may be eccentric relative to an axis of the blood vessel over 50% of the time, possibly in as much as (or even more than) 75% of cases. The devices and methods of the present invention will often be particularly well suited for directing treatment eccentrically, often in response to circumferential detecting or imaging of the material proximate to the lumen. While the methods and devices described herein allow such eccentric treatments, the devices may also be used for treatment of radially symmetric lumens or tissues by selectively directing energy in a radially symmetric pattern.

While the present invention may be used in combination with stenting and/or balloon dilation, it is particularly well suited for increasing the open diameter of blood vessels in which stenting and balloon angioplasty are known to have limitations, such as treatment of in-stent restenosis, and diffuse disease, in which stenosis is spread along a significant length of an artery rather than being localized in one area. The present invention may also provide advantages in treatment of tissues proximate to, but, not located on the surface of a luminal wall, for example, tissue at a depth of as much as 5 mm or more. The invention may also find advantageous use for treatment of tortuous, sharply-curved vessels, as no stent need be advanced into or expanded within the sharp bends of such blood vessels; this may further include the arteries of the leg where prior stenting has been complicated by implant fracture, persistent diffuse disease, or vessel tortuosity. Still further advantageous applications include treatment along bifurcations (where side branch blockage may be an issue) and in the peripheral extremities such as the legs, feet, and arms where implants may not reach due to size limitations, or other factors that prevent use of stents.

Embodiments of the invention may measure impedance of a circuit, and particularly of a circuit that includes an electrode coupled with a luminal wall or other tissue. Such impedance measurements of alternating current (AC) circuits may often include a measurement of both a real portion or magnitude of the impedance, and an imaginary portion or phase angle of the impedance. The impedance magnitude and phase angle generated at an appropriate frequency by a tissue coupled to the electrode may provide a tissue signature. To enhance the accuracy of tissue signature measurements, a plurality of individual measurements (often three or more) may be taken and averaged. By measuring tissue signatures at a plurality of different frequencies within a frequency range, a signature profile for the tissue may be generated, with the signature profiles optionally comprising a curve or curve-fit of phase angles and magnitudes throughout a frequency range. For example, measurement may be taken at one frequency, or as few as 2 different frequencies, or as many as 100 or more different frequencies. In some embodiments, tissue signature measurements may be compared, and/or a smaller number (2-10 or 5-50) of such measurements may be included in a tissue signature profile. Tissue signature measurements may depend on the measurement conditions (including the configuration of the electrodes/tissue coupling), particularly when the measurements are performed by transmitting bipolar tissue sensing current between two electrodes that are supported by a radially expandable support structure. Nonetheless, the relative tissue signatures and/or signature profiles of different tissues of different patients, particularly the relative offsets and/or the relative slopes, will often be sufficiently consistent to allow the tissue signatures and signature profiles to be used to distinguish between one or more of implant surfaces, target tissue, tissue proximate to the electrodes.

The present invention may additionally take advantage of the differences in tissue properties. If one tissue has a better thermal conductivity (k) than another type of tissue, it will conduct heat away more rapidly. If one tissue has a lower specific heat capacity (cp) than another type of tissue, its temperature will increase more given the same amount of energy applied to the same mass (and volume, assuming relatively similar tissue density). If one type of tissue has denser vasculature, or is reliably in closer proximity to well-perfused areas, it will conduct heat away more rapidly.

Optionally, baseline measurements of tissues, which may be characterized via intravascular ultrasound, optical coherence tomography, etc., may be taken to help differentiate adjacent tissues, as the tissue signatures and/or signature profiles may differ from person to person. Additionally, the tissue signatures and/or signature profile curves may be normalized to facilitate identification of the relevant slopes, offsets, etc., between different tissues. Once sufficient frequency and profile correlations have been established between tissue signatures, and the profiles of different tissues for a number of different patients and measurement conditions, tissue characterization of at least some patients may be provided without having to resort to other baseline tissue characterization methodologies. Correlations may include any of impedance magnitude, phase angle, including the relative slopes and/or offsets thereof.

Figure 1B:
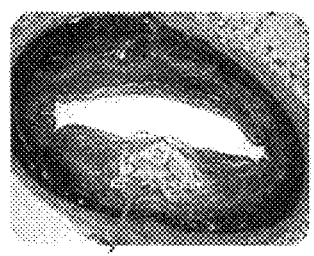
FIG. 1B illustrates vulnerable plaque within a blood vessel.
Figure 1C:
FIG. 1C illustrates the sharp bends or tortuosity of some blood vessels.
Figure 1D:
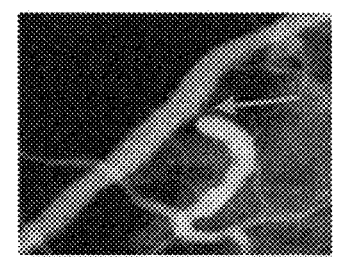
FIG. 1D illustrates atherosclerotic disease at a bifurcation.
Figure 1E:
FIG. 1E illustrates a lesion associated with atherosclerotic disease of the extremities.
Figure 1F:
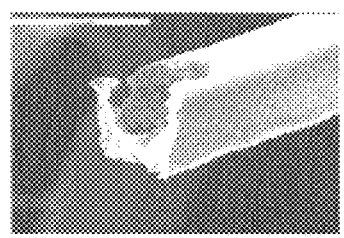
FIG. 1F is an illustration of a stent fracture or corrosion.

Diffuse disease and vulnerable plaque are illustrated in FIGS. 1A and 1B, respectively. FIG. 1C illustrates vascular that can result from atherosclerotic disease of the extremities. FIG. 1F illustrates a stent structural member fracture which may result in eventual restenosis of the artery.

Figure 1G:
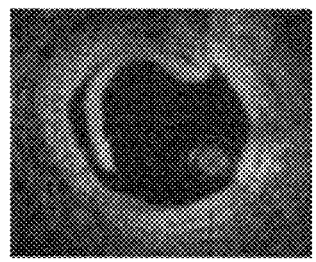
FIG. 1G illustrates a dissection within a blood vessel.
Figure 1H:
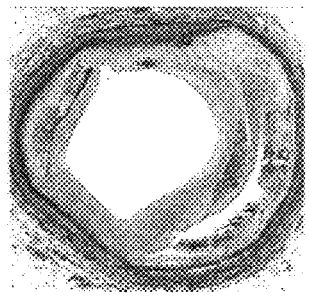
FIG. 1H illustrates a circumferential measurement of an artery wall around a healthy artery.
Figure 1I:
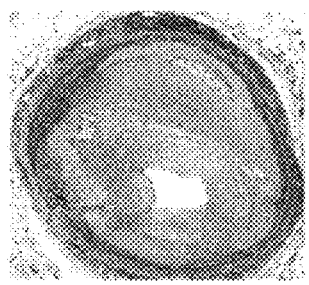
FIG. 1I illustrates circumferential distribution of atheroma about a restenosed artery.

Arterial dissection and restenosis may be understood with reference to FIGS. 1G through 1I. The artery comprises three layers: an endothelial layer, a medial layer, and an adventitial layer. During angioplasty, the inside layer may delaminate or detach partially from the wall so as to form a dissection as illustrated in FIG. 1G. Such dissections divert and may obstruct blood flow. As can be understood by comparing FIGS. 1H and 1I, angioplasty is a relatively aggressive procedure which may injure the tissue of the blood vessel. In response to this injury, the presence of a stent, and/or in the continuing progression of the original atherosclerotic disease, the opened artery may restenose or subsequently decrease in diameter as illustrated in FIG. 1 I.

In general, the present invention provides a catheter that is relatively quick and easy to use by the physician. The catheter system of the present invention may allow arteries to be opened to a significant percentage of their nominal or native artery diameter. In some embodiments, arteries may be opened to as much as about 85%, while acute openings may be less than 85%. Rapid stenosis reduction may be effected using sufficient power to heat tissues locally to temperatures ranging from about 50° C. to about 65° C. using gentle heating.

Alternatively, a milder treatment may be implemented, for example, providing a lumen of about 50% native diameter when treatment is complete, but that may still provide as much as 80% or more of native vessel open diameters after a subsequent healing process is complete (see Table 3). Resorption of treated luminal tissues is a preferred biological response by the targeted tissue treatment areas. Some embodiments may heat at least some stenotic tissue to a temperature in a range from about 55° C. to about 80° C. Higher temperatures up to about 100° C. could be used for the purpose of the tissue treatment.

In other embodiments, heating may be controlled so as to provide tissue temperatures in a range between about 50° C. and about 65° C., with some embodiments benefiting from maximum tissue temperatures of about 63° C. Advantageously, the systems and methods of the present invention may be used below the balloon dilation pressures typically associated with balloon angioplasty (6 atmospheres or less as opposed to 10 or more atmospheres), thereby avoiding dissections and dilation-based tissue injury known to chronically result in restenosis. Optionally, treatments of tissues may be repeated during a single surgical session, or after a month or more (even after a year or more) to provide or maintain a desired opening of the lumen.

To keep surface temperatures of the tissue in a range from about 50° C. to about 65° C., power is applied to treatment zones (tissue between electrode pairs) using combinations of power and time that are chosen to derive the desired tissue response. Table 1 shows sample results of experimental testing done on a cadaver aorta using various electrode energy settings and surface temperatures achieved versus time. By ranging the average power between 1 and 5 Watts for between 0.5 and 10 seconds, the surface temperature reached was between 50° C. and 65° C. Trial doses are shown below in Table 1.

TABLE 1

| Approx. Power | Average Time | Surface Temp |
| --- | --- | --- |
| 1 Watt | 8 sec | 50° C. |
| 2 Watt | 2 sec | 50° C. |

TABLE 1-continued

| Approx. Power | Average Time | Surface Temp |
| --- | --- | --- |
| 3 Watt | 1.3 sec | 50° C. |
| 4 Watt | 1 sec | 50° C. |
| 5 Watt | .5 sec | 50° C. |
| 2 Watt | 4 sec | 60° C. |
| 3 Watt | 2 sec | 60° C. |
| 4 Watt | 1.5 sec | 60° C. |
| 5 Watt | 1 sec | 60° C. |
| 3 Watt | 3 sec | 65° C. |
| 4 Watt | 2 sec | 65° C. |

Regarding the length and spacing of the electrodes within a particular pair, these factors are inter-related with power and impedance. As the length of the electrodes decreases, the impedance seen by the generator will go up, but the volume of tissue will go down, so that the power setting on the generator may be decreased. As the gap between the electrodes widens, the impedance seen by the generator will also go up, but the volume of tissue will go up as well, so that the power setting on the generator should be increased. Hence, there are roughly opposed effects on load impedance when decreasing electrode length and increasing electrode spacing.

Desired power, energy, and time of the treatment are likewise inter-related, and may also be at least related with electrode geometry. Speaking very generally, lower power treatments applied for long times tends to result in treatments with relatively higher total energies, while higher power treatments for shorter times tends to result in lower energy treatments. If the electrode spacing were doubled, power may increase by four times. The power transmitted into the tissue can be calibrated and scaled to the particular electrode configuration, often in order to keep the power and energy density in a desirable range.

Power settings may be scaled by varying the electrode configuration. If, for instance, the inner edge-to-edge spacing of the electrodes were doubled, roughly 4 times the power may be applied because the volume of tissue becomes roughly 4 times larger. As such, an electrode configuration that is somewhat different from the exemplary embodiments described herein could be used within a power range of roughly 4 to 20 Watts. Shortening the electrodes, and thus shortening and reducing the volume of the remodeling zones, would also affect the magnitude of the power that may be applied to the tissue volume.

Figure 3:
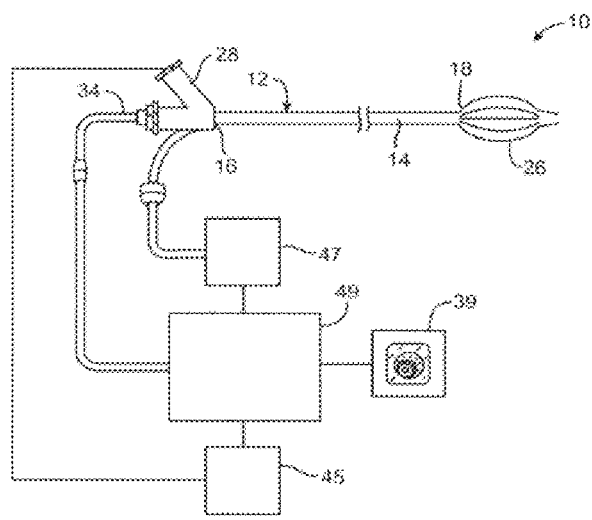
FIG. 3 schematically illustrates a catheter system for remodeling atherosclerotic material, the system including the catheter of FIG. 2.
Figure 36:
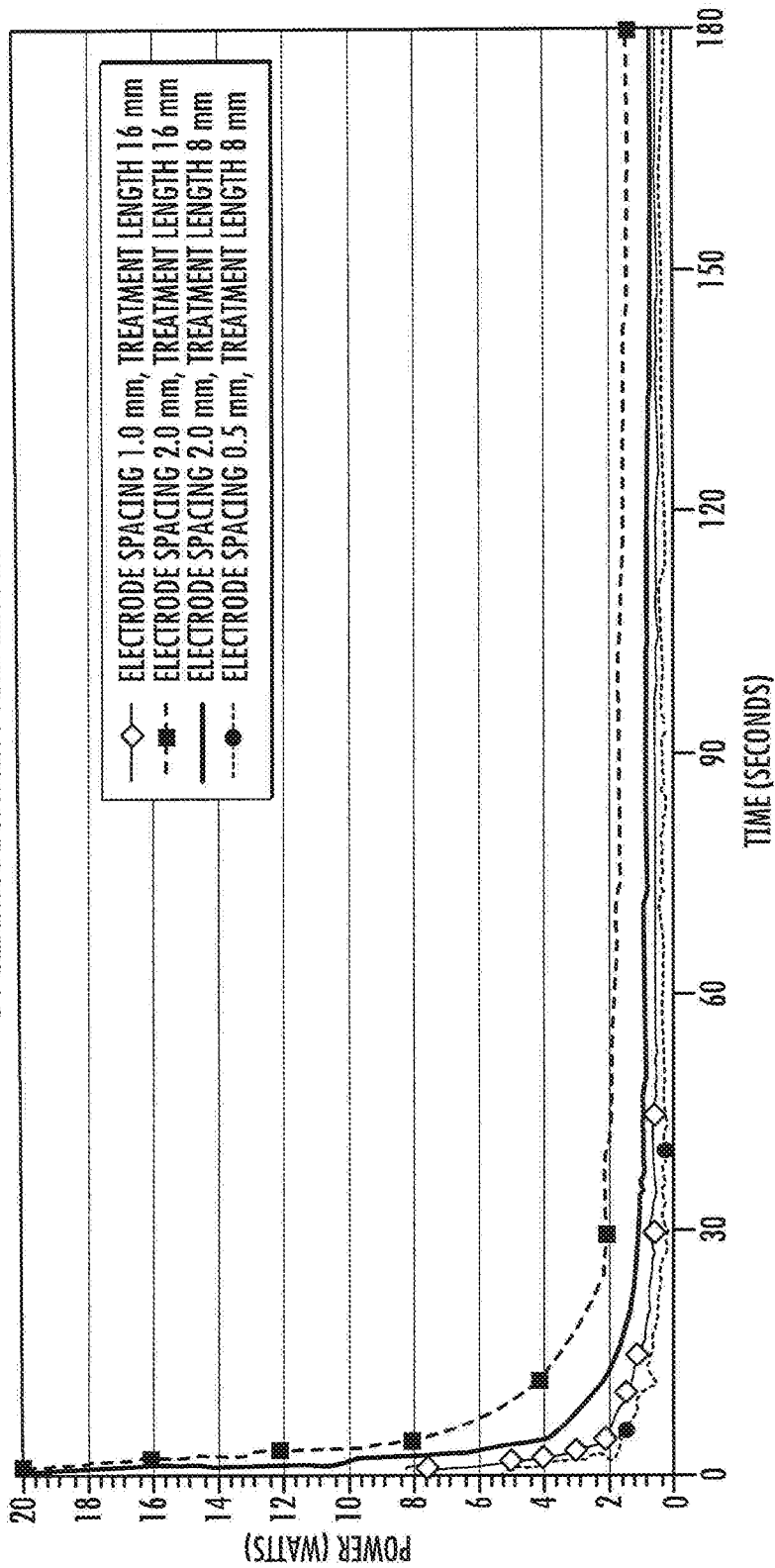
FIG. 36 illustrates relationships between energy delivery and electrode spacing for the systems of FIGS. 2 and 33.
Figure 37:
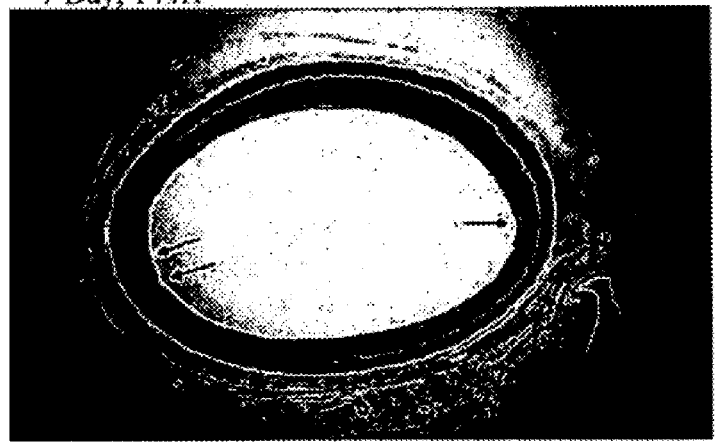
FIG. 37 shows histological results for the application of 1 Watt for 8 seconds at seven days.
Figure 38:
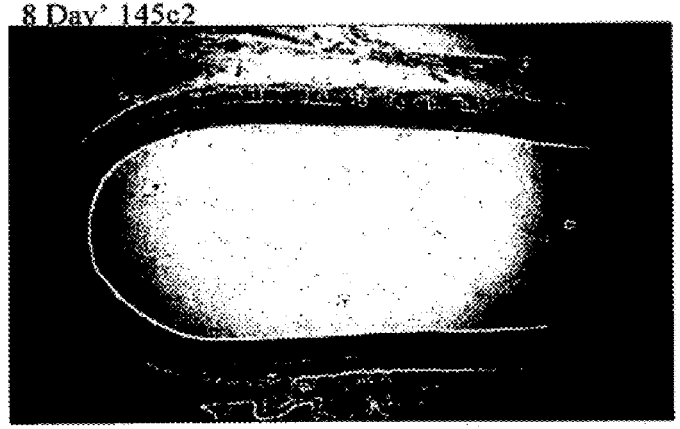
FIG. 38 shows histological results for the application of 2 Watts for 2 seconds at eight days.
Figure 39A:
FIGS. 39A and 39B show histological results for the application of 4 Watts for 1 second at seven days.
Figure 39B:
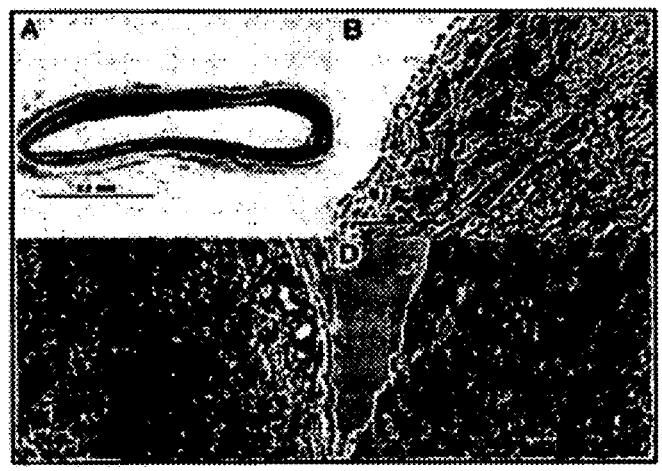
Figure 39C:
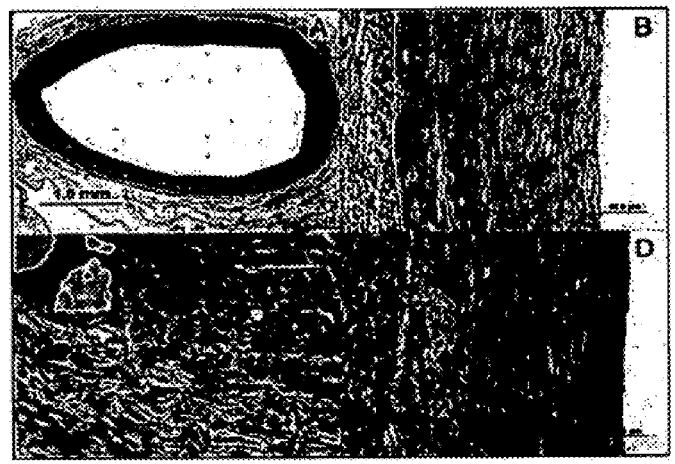
FIG. 39C shows histological results for the application of 4 Watts for 1 second at thirty days.
Figure 40A:
FIGS. 40A and 40B show histological results for the application of 2 Watts for 4 seconds at seven days.
Figure 40B:
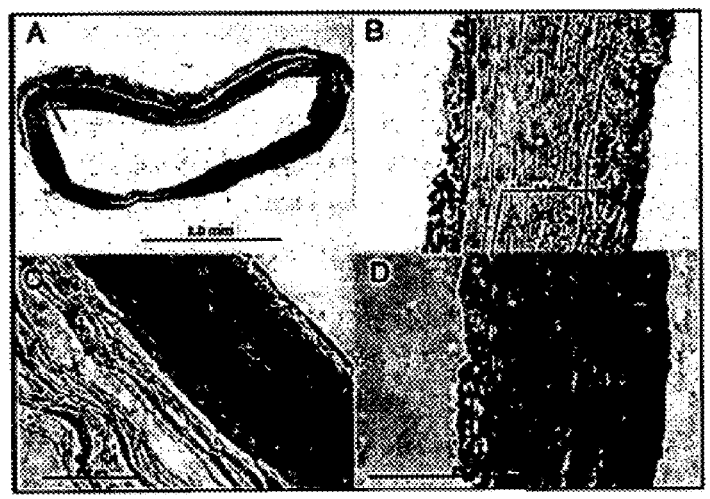
Figure 40C:
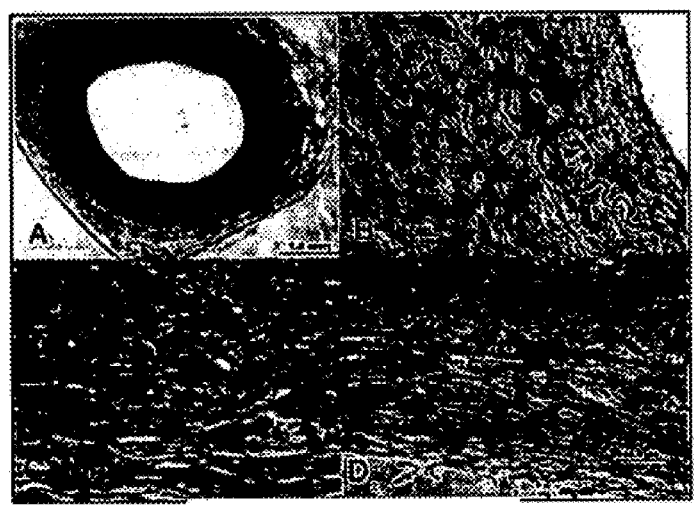
FIG. 40C shows histological results for the application of 2 Watts for 4 seconds at thirty days.
Figure 41A:
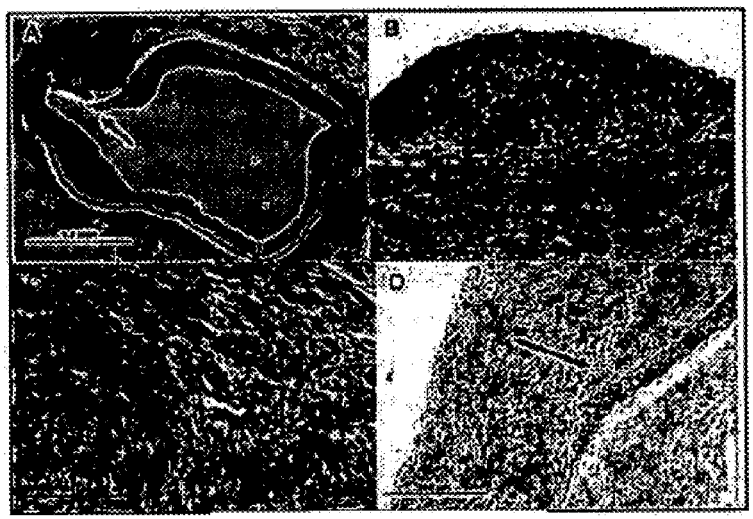
FIG. 41A shows histological results for the application of 3 Watts for 2 seconds at seven days.
Figure 41B:
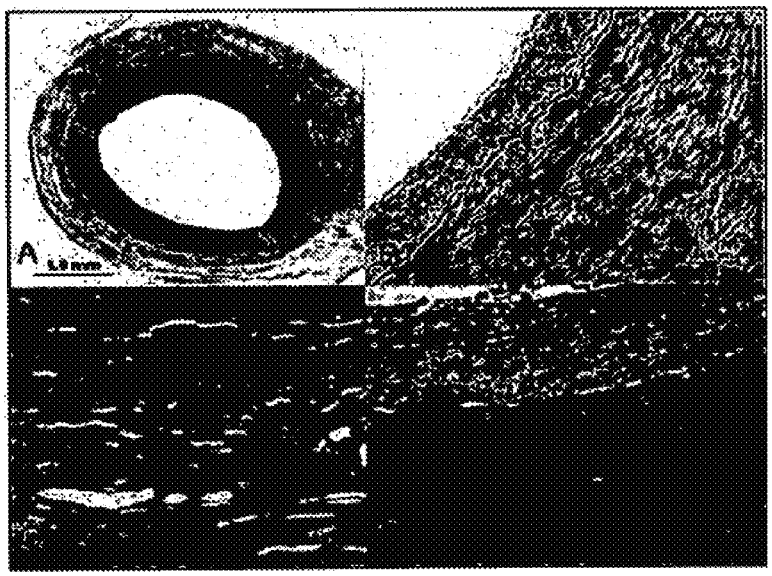
FIG. 41B shows histological results for the application of 3 Watts for 2 seconds at thirty days.

Referring to FIG. 36, in order to quantify this complex set of relationships, and bound the preferred space within which the exemplary treatment device operates, an empirical relationship between safe values of several of these parameters may be generated and provided graphically, in table form, or by a mathematical relationships. An exemplary equation describing a particularly advantageous relationship is: $power = b*x^2*L*(t^{-0.59})$, where b is a parameter in the range of 0.2 to 0.6, x is the inner edge-to-edge spacing of the electrodes in millimeters, L is the length of the electrodes in millimeters (and also the approximate length of the remodeling zone), the power is in Watts, and t is time in seconds, b has units of $Watts/(mm^3)*(seconds^{0.59})$. Exemplary treatments in the range described by this equation include treatments such as 4 Watts for 2 seconds, 3 Watts for 3 seconds, 2 Watts for 4 seconds, and 1 Watt for 12 seconds using the exemplary electrode geometries described herein. Additionally, very low power and long duration treatments such as 0.25 Watts for 180 seconds are included in this relationship. Alternative suitable treatment ranges fall within or near the set of curves shown in FIG. 36, which shows approximate numbers for maximum power and time by electrode dimensions. Still further alternative treatment parameter values can be understood with reference to Table 2, which shows total energies for different combinations of power and time for a few different electrode pair geometries.

or the like, ideally for introducing heparinized saline. Both first and second connectors 32, 44 may optionally comprise a standard connector such as a Luer-Loc™ connector. In FIG. 3 connector 44 is schematically shown coupled to an aspiration vacuum source/infusion fluid source 45.

Referring now to FIG. 16, an exemplary catheter system 280 is illustrated. In this embodiment, catheter body 282

TABLE 2

| Exemplary Peripheral Treatment Catheter | | | Alternative I Peripheral Treatment Catheter | | | Alternative II Peripheral Treatment Catheter | | | Exemplary Coronary Treatment Catheter | | |
|---|---|---|---|---|---|---|---|---|---|---|---|
| X = 1 mm, L = 16 mm | | Total | X = 2 mm, L = 16 mm | | Total | X = 2 mm, L = 8 mm | | Total | X = 0.5 mm, L = 8 mm | | Total |
| Time (s) | Power (W) | Energy (J) | Time (s) | Power (W) | Energy (J) | Time (s) | Power (W) | Energy (J) | Time (s) | Power (W) | Energy (J) |
| 1 | 5 | 5 | 1 | 20 | 20 | 1 | 10 | 10 | 1 | 0.625 | 0.625 |
| 2 | 4 | 8 | 2 | 16 | 32 | 2 | 8 | 16 | 2 | 0.5 | 1 |
| 3 | 3 | 9 | 3 | 12 | 36 | 3 | 6 | 18 | 3 | 0.375 | 1.125 |
| 4 | 2 | 8 | 4 | 8 | 32 | 4 | 4 | 16 | 4 | , 0.25 | 1 |
| 12 | 1 | 12 | 12 | 4 | 48 | 12 | 2 | 24 | 12 | 0.125 | 1.5 |
| 30 | 0.5 | 15 | 30 | 2 | 60 | 30 | 1 | 30 | 30 | 0.0625 | 1.875 |
| 180 | 0.25 | 45 | 180 | 1 | 180 | 180 | 0.5 | 90 | 180 | 0.03125 | 5.625 |

Figure 2:
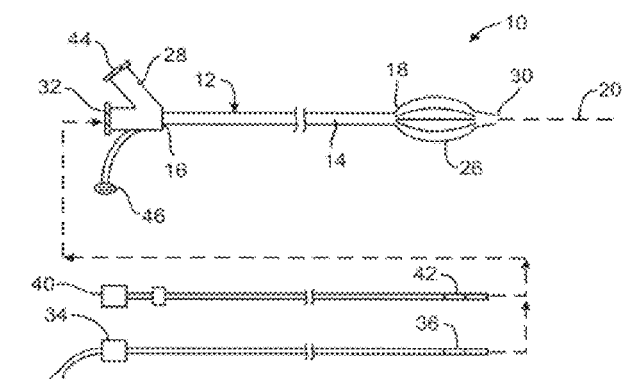
FIG. 2 schematically illustrates an energy delivery catheter system according to the present invention.

An exemplary catheter system 10 is schematically illustrated in FIGS. 2 and 3. An energy delivery catheter 12 includes a catheter body 14 having a proximal end 16 and a distal end 18. Catheter body 14 is flexible and defines a catheter axis 20, and includes an aspiration lumen 22 and an irrigation lumen 24 (see FIG. 3). Still further lumens may be provided for a guidewire, imaging system, or the like as described below. Lumen 22 may be used for sensing and/or imaging as well as aspiration.

Catheter 12 includes a radially expandable structure 26 adjacent distal end 18 and a housing 28 adjacent proximal end 16. A distal tip 30 may include an integral tip valve to seal aspiration lumen 22 and allow passage of guidewires, imaging, and the like.

Proximal housing 28 includes a first connector 32 in fluid communication with aspiration lumen 22. Aspiration lumen 22 may have an aspiration port within expandable structure 26 so as to allow aspiration or aspiration of debris and gasses from within the expandable structure. Aspiration lumen 22 may also be used as an access lumen for guidewires, intravascular imaging catheters, and/or distally advancing intravascular radiation treatment catheters or restenosis inhibiting drugs. Hence, connector 32 may selectively accommodate an imaging catheter 34 having an atherosclerotic material detector 36 advanceable within catheter body 14 adjacent to and/or beyond distal end 18, the detector often comprising an intravascular ultrasound transducer, an optical coherent tomography sensor, an MRI antenna, or the like. An imaging connector 38 of imaging catheter 34 transmits imaging signals allowing circumferential measurement of atherosclerotic thicknesses about axis 20 to a display 39.

Optionally, connector 32 also accommodates a restenosis inhibiting treatment catheter 40, the treatment catheter here comprising an intravascular radiation catheter. Such a radiation catheter may include a radiation source 42 which can again be advanced distally within catheter body 14 to or beyond expandable structure 26.

Figure 4:
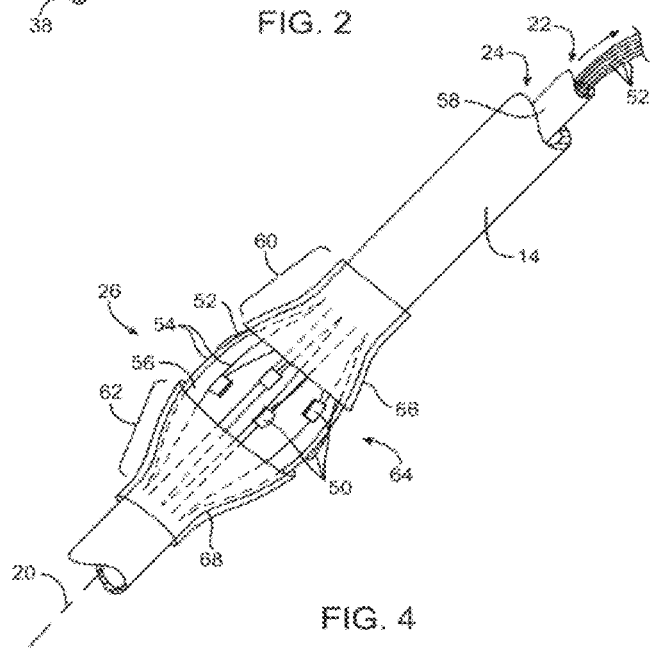
FIG. 4 illustrates an expandable basket and an associated electrode array of the catheter system of FIG. 2.

A second connector 44 of proximal housing 28 is in fluid communication with irrigation lumen 24 (see FIG. 4). Second connector 44 may be coupled to an irrigation fluid source for introducing conductive or non-conductive liquids, includes only a single lumen, which is large enough to accommodate an imaging catheter therein and also to be used as an irrigation lumen to bring irrigation fluid to irrigation ports 284. The lumen may decrease in diameter distally of irrigation ports 284, with the decreased diameter portion 286 fittingly receiving the imaging catheter within the lumen thereof so as to direct the irrigation fluid radially outward through the plurality of irrigation ports. This embodiment may be particularly useful when remodeling atherosclerotic materials using the methods illustrated in FIGS. 14A-14H, in which mild heating improves vessel size, optionally without requiring aspiration.

Catheter body 282 may include a braided shaft in which conductive wires (for example copper wires or beryllium-copper wires) are coated with a high temperature and/or high strength insulation material such as a layer of polyimide or the like. The braided wires may be sandwiched between layers of materials forming the shaft of catheter body 282. The shaft may, for example, comprise a plurality of layers of polyethylene, an inner Teflon™ PTFE layer, an outer nylon layer, and the like.

The wires of shaft 282 may be braided so as to inhibit capacitive losses between wires when electrical currents run through them. Capacitive losses may be decreased when a wire that carries a current from an energy source to an electrode of the catheter system and a wire that carries a current from an electrode back to the energy source are not parallel, but at an angle, ideally being perpendicular. This may be achieved by braiding the wires with appropriate pitch or a number of peaks per inch. The basket structure 170 of catheter system 280 may be included, with the basket structure being described in more detail with reference to FIGS. 12A-12H. Guide 286 may extend through basket 170 and may comprise a material transparent to the imaging catheter, optionally comprising HDPE, PET, or the like.

Referring now to FIGS. 2, 3, and 4, proximal housing 28 also accommodates an electrical connector 46. Connector 46 includes a plurality of electrical connections, each electrically coupled to an electrode 50 via a dedicated conductor 52. This allows a subset of electrodes 50 to be easily energized, the electrodes often being energized with bipolar or monopolar radiofrequency energy. Hence, electrical connector 46 will often be coupled to an radiofrequency generator via a controller 47, with the controller allowing energy to be selectively directed to an eccentric portion of an engaged luminal wall. When monopolar radiofrequency energy is employed, patient ground may (for example) be provided by an external electrode or an electrode on catheter body 14. A processor 49 may manipulate signals from imaging catheter 34 to generate an image on display 39, may coordinate aspiration, irrigation, and/or treatment, and may automatically register the treatment with the image.

Processor 49 will typically comprise computer hardware and/or software, often including one or more programmable processor unit running machine readable program instructions or code for implementing some or all of one or more of the methods described herein. The code will often be embodied in a tangible media such as a memory (optionally a read only memory, a random access memory, a non-volatile memory, etc.) and/or a recording media (such as a floppy disk, a hard drive, a CD, a DVD, a memory stick, etc.). The code and/or associated data and signals may also be transmitted to or from the processor via a network connection (such as a wireless network, an Ethernet, an internet, an intranet), and some or all of the code may also be transmitted between components of catheter system 10 and within processor 49 via one or more bus, and appropriate standard or proprietary communications cards, connectors, and cables, will often be included in the processor. Processor 49 will often be configured to perform the calculations and signal transmission steps described herein at least in part by programming the processor with the software code, which may be written as a single program, a series of separate subroutines or related programs. The processor may comprise standard or proprietary digital and/or analog signal processing hardware, software, and/or firmware, and will typically have sufficient processing power to perform the calculations described herein during treatment of the patient, the processor optionally comprising a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

In general, the present invention may make use of highly elastic, expandable structures, particularly of balloons or expandable structures formed from structural members separated by perforations so as to define a basket. Such structures can conform to an artery diameter before, during, and/or after atherosclerotic material removal. This expandability allows for direct contact of the electrodes against a targeted area, although the systems of the present invention may also make use of conductive fluid environments to complete a radiofrequency energy path, or conversely, use non-conductive fluid to enhance energy directed through tissue. Multiple electrodes can be distributed circumferentially around an intermediate portion of the expandable structure, and a subset of these electrodes can be activated to allow for eccentric tissue treatment.

Expandable structure 26 is illustrated in more detail in FIG. 4. Expandable structure 26 may expand resiliently when released from within a restraining sheath, or may expand by pulling tip 30 toward distal end 18 (see FIG. 2), optionally using a pullwire, an inner catheter body 58, or the like. Expandable structure 26 here comprises a perforate structure or basket having a series of structural struts or elements 54 with opening or perforations 56 therebetween. Perforations 56 may be formed, for example, by cutting elongate slits in a flexible tube material, or the basket may be formed by braiding elongate wires or ribbons, or other such suitable materials.

Expandable structure 26 generally includes a proximal portion 60, a distal portion 62, and an intermediate portion 64 therebetween. Each electrode 50 is mounted on an associated basket element 54 along intermediate portion 64, with an associated conductor 52 extending proximally from the electrode. Electrodes 50 are distributed circumferentially about axis 20 in an array, adjacent electrodes preferably being axially offset, ideally being staggered or alternating between proximal and distal axial locations. This allows bipolar energy to be directed between adjacent circumferential (sometimes axially offset) electrodes between adjacent distal electrodes, between adjacent proximal electrodes, and the like.

In some embodiments, proximal and distal barriers 66, 68 expand radially with proximal and distal portions 60, 62 of expandable structure 26. Barriers 66, 68 inhibit any debris and gases generated adjacent electrodes 50 from traveling within the body lumen beyond catheter 12. Barriers 66, 68 also allow an at least partially isolated environment to be established within the body lumen, for example, by replacing blood within a blood vessel with a more advantageous fluid environment for the electrodes. Alternative barriers may be provided instead of (or in combination with) barriers 66, 68, including one or more balloons axially offset from expandable member 26, elastic lips, or other such barrier structures. In other embodiments remodeling may be effected without generating significant debris, a desired treatment environment may be provided with localized irrigation and/or aspiration flows so that some systems may forego the use of barriers.

Figure 5:
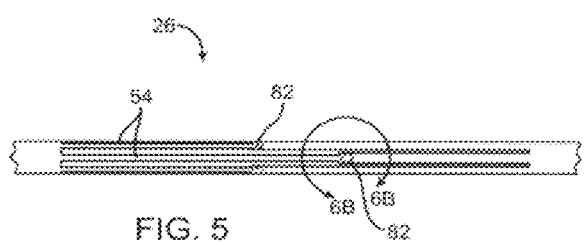
FIGS. 5 and 6 illustrate an exemplary basket structure having alternating axially offset electrodes in a circumferential array.
Figure 6:

An exemplary expandable structure 26 is formed by cutting slots in a superelastic alloy tube such as a nickel titanium alloy or Nitinol™ tube. As can be understood with reference to FIG. 6, expandable structures 54 may have circumferential widths 80 which are enhanced adjacent an electrode and/or electrode mounting location 82. As can be seen in FIG. 5, the localized enhancement of the width 80 adjacent electrode mounting pads 82 may be axially offset, as described above. The slots forming expandable members 54, and hence the expandable members themselves may, for example, be 0.8 inches in length, with the expandable members having a circumferential width of about 0.25 inches.

Figure 7A:
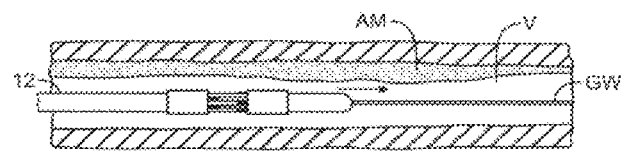
FIGS. 7A-E illustrate an exemplary atherosclerotic material remodeling and/or removal method using the catheter system of FIG. 2.
Figure 7B:
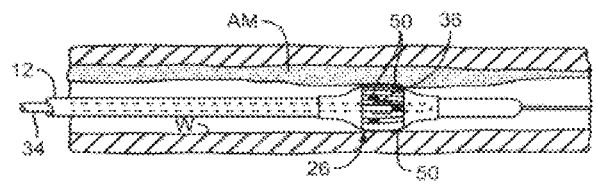
Figure 7C:

Referring now to FIGS. 7A and 7B, side and end views of an expandable barrier in the form of a collapsible cone can be seen. Barrier 66 here comprises a braided Nitinol™ wire 84 coated in silicone, for example, by dipping a braid of a superelastic alloy such as a Nitinol™ braid in liquid silicone and allowing it to harden. Such cones may then be mounted over the proximal and distal portions of the expandable structure. As noted above, a variety of alternative barrier membranes may be employed. FIG. 7C illustrates a basket 75 with an integral barrier 77 coated directly on the basket. Barrier 77 comprises a polyurethane, which may be quite tear resistant. Alternative barrier membranes may comprise other materials such as PT1-E, or the like.

Figure 8:
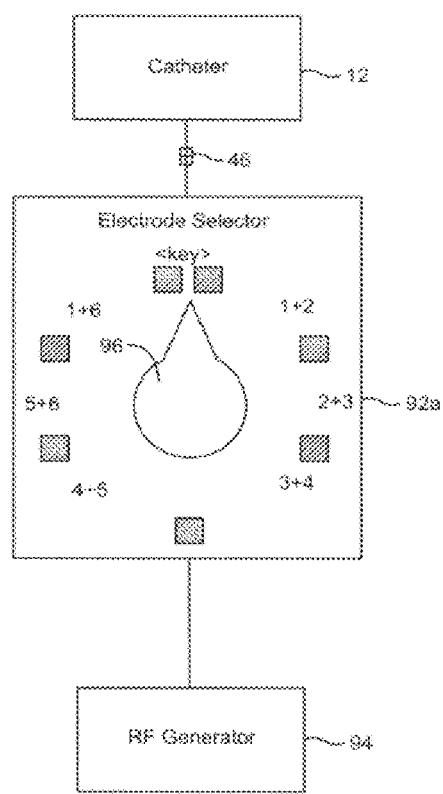
FIGS. 8-10 schematically illustrate controllers for selectively energizing electrodes in the system of FIG. 2.
Figure 9:
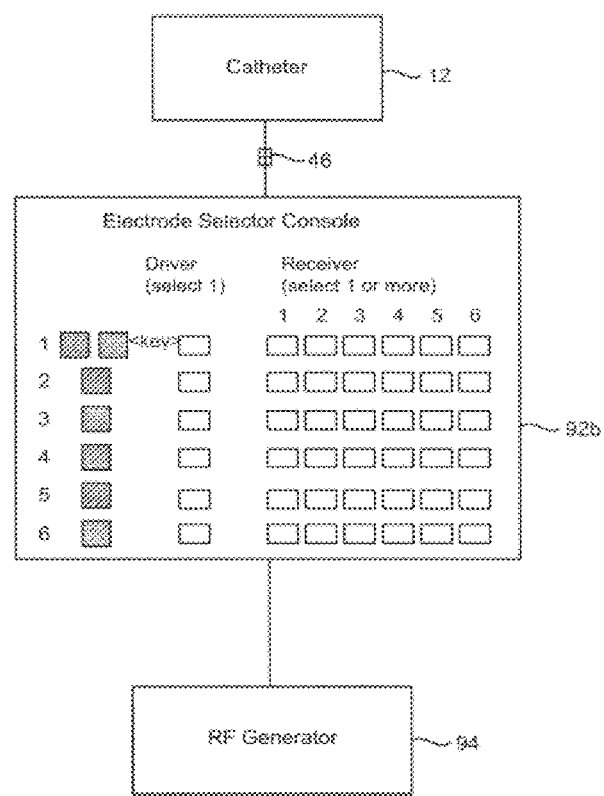

Referring now to FIGS. 8 and 9, exemplary electrodes 50 supported by polyimide alloy expandable members 54 may be coated with a high-temperature polymer. Conductors 52 extend proximally from electrodes 50 as described above.

High contrast radiopaque markers such as gold, platinum, or platinum/iridium alloy may be attached to or near these struts. The markers could also be used as the electrodes.

Referring now to FIGS. 33, 33A, 34, 35A-35F, the present invention discloses a method for remodeling artery tissue using a catheter system that uses mild heat to provide tissue surface temperatures in a range between about 50° C. and about 65° C. to gently remodel the tissue, such that arteries may be opened. The method includes expanding a catheter balloon within the artery lumen with a first pressure that brings the balloon in contact with the artery tissue. The plurality of electrodes 634 are coupled with the artery tissue 650 so as to define a plurality of remodeling zones in the artery tissue 650 when the balloon 620 is in contact with the artery tissue 650. The plurality of electrode pairs 634A-634 F are then energized with associated desired quantities of bipolar tissue remodeling energy so as to heat each of the plurality of remodeling zones with the associated desired tissue remodeling energy, the remodeling energy being configured to avoid muscular contraction and inhibit both acute and long-term occlusion of the lumen. In some instances, it may be desirable to obtain baseline measurements of the tissues to be treated (which may be characterized with means such as intravascular ultrasound, optical coherence tomography, etc.). Baseline measurements may be taken to help differentiate adjacent tissues, as the tissue signatures and/or signature profiles may differ from person to person. Additionally, the tissue signatures and/or signature profile curves may be normalized to facilitate identification of the relevant slopes, offsets, and the like between different tissues.

As shown in FIG. 33, one embodiment of a catheter system for use in the present invention includes an angioplasty catheter with a plurality of electrodes 634 mounted on the exterior of a angioplasty balloon 620. A radiofrequency controller 49, generator or power source 642, and connecting cable 46 provide energy to the catheter. Catheters may be approximately 135 cm in length and may be provided with balloon diameters ranging from about 2 mm to about 10 mm so as to accommodate common arterial sizes. The catheter uses mechanical and radiant energy intended to modify tissue proximate to a lumen 660, such as in-stent restenosis, or other diseased tissue, resulting in a larger artery lumen. The temperature that is generated is low and the total application time is shorter than most angioplasty procedures performed today. The catheter device is compatible with standard angioplasty equipment, thereby allowing access of vasculature via contralateral or ipsilateral common femoral approach using conventional angioplasty techniques. The catheter system 10 includes a balloon catheter 12 having a catheter body 14 with a proximal end 16 and a distal end 18. Catheter body 14 is flexible and defines a catheter axis 20, and may include one or more lumens, such as a guidewire lumen and an inflation lumen. Still further lumens may be provided if desired for other treatments or applications, such as perfusion, fluid delivery, imaging, or the like. Catheter 12 includes an inflatable balloon 620. Housing 629 includes a first connector 626 in communication with guidewire lumen 622 and a second connector 628 in fluid communication with inflation lumen 624. Inflation lumen 624 extends between balloon 620 and second connector 28. Both first and second connectors 626, 628 may optionally comprise a standard connector, such as a Luer-Loc™ connector. Housing 629 also accommodates an electrical connector 638 electrically coupled to electrodes 634 via conductors 636. This allows electrodes 634 to be easily energized, the electrodes often being energized by a controller 49 and power source 642, such as bipolar or monopolar radiofrequency energy, microwave energy, ultrasound energy, or other suitable energy sources. In one embodiment, electrical connector 46 is coupled to a radiofrequency generator via a controller 49, with controller 49 allowing energy to be selectively directed to electrodes 634. Electrodes 634 are mounted on a surface of balloon 620, with associated conductors 636 extending proximally from the electrodes. Electrodes 634 may be arranged in many different patterns or arrays on balloon 620. The system 10 may be used for monopolar or bipolar application of energy. For delivery of monopolar energy, a ground electrode is used, either on the catheter shaft 14, or on the patients skin, such as a ground electrode pad. For delivery of bipolar energy, adjacent electrodes are axially offset to allow bipolar energy to be directed between adjacent circumferential (axially offset) electrodes 634.

Referring to FIGS. 33, 33A, 34, and 35D, multiplexing between selected electrodes of an array or sub-array can be effected by selectively energizing a plurality of electrode pairs, such as those shown by 634A-634F, treatment zones for the sub-array being disposed between the electrodes of the pairs so that the energy passes therethrough. For example, a pair of electrodes selected from electrodes 634A, 634B, 634C, 634D, 634E, 634F distributed about balloon 620 (with the selected electrodes optionally being positioned opposite each other) may be energized and then turned off, with another pair then being energized, and so forth. An example of a firing order may be 634A and 634D, then 634B and 634E, then 634C and 634F. Bipolar potentials between the electrodes of the pair can induce energy paths 653 in the same general tissue region, with the power dissipated into the tissue optionally remaining substantially constant. The electrode combinations 634A-634F may be chosen so as to minimize the space between treatment zones as represented by energy path 653, where treatment zones may be defined by the tissue volume between paired electrodes. For example, an in-stent restenosis may require energy delivery around the full circumference of a lumen but the open portion of the lumen may not be concentric with the natural center of the healthy vessel (as shown, for example in FIG. 35A). In this circumstance, individual pairs of electrodes 634A-634F may be energized and controlled until a desired temperature is reached or until proximity to the implanted stent 652 is reached (FIG. 35E). Electrode pairs may optionally be selected again so as to fill in the gaps between the first tissue treatment zones 653 and the controlled delivery of energy may be repeated such that essentially the full circumference of the lumen receives treatment and is restored as shown in FIG. 35F. Most preferably for treating in-stent restenosis, a first plurality of electrode pairs selected from 634A-634F are energized sequentially to create a first pattern of treatment zones. Then, an indexed plurality of electrode pairs selected from 634A-634F are chosen so as to create a second pattern of treatment zones, with at least some degree of overlap with the first treatment zones, and then energized sequentially to complete the energy treatment dosage to be used. An exemplary energy dose for in-stent restenosis may be for the first plurality of electrodes to be provided 4 Watts of power for 2 seconds, and the second plurality of electrodes to be provided 4 Watts of power for 1 second.

Figure 13:
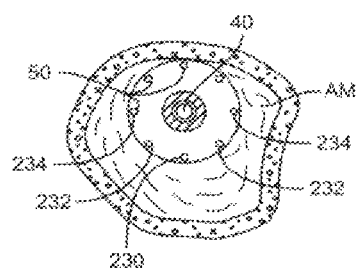
FIG. 13 is a schematic cross sectional view showing the application of different power levels through different electrodes so as to eccentrically remodel atherosclerotic materials.

Referring now to FIG. 13, controllers of the catheter systems described herein may allow distribution of differing power levels to differing pairs of electrodes. For example, in response to a circumferential distribution of atherosclerotic material AM such as that illustrated in FIG. 13, a controller may direct 50 watts of energy to a first electrode 230, 30 watts of energy to a pair of second electrodes 232 and only 10 watts of energy to a pair of third electrodes 234. Other electrodes may have no energy directed to them. In some embodiments, a differing power directed to the differing electrodes may be provided by controlling the duty cycle, for example, with 50 watts being provided by energizing one or more electrode for 50% of the time, 30 watts being provided by energizing an electrode 30% of the time, and the like. The power and the duration of the cycle may be of any value to achieve the desired treatment, which for example, may include powers and times computed within a temperature regulating closed-loop control algorithm.

Referring now to FIG. 34, balloon 620 generally includes a proximal portion 630 coupled to inflation lumen 624 and a distal portion 632 coupled to guidewire lumen 622. Balloon 620 expands radially when inflated with a fluid or a gas. In some embodiments, the fluid or gas may be non-conductive and/or cooled. In some embodiments, balloon 620 may be a low pressure balloon pressurized to 6 atmospheres or less to contact the artery tissue. In other embodiments, balloon 620 is a standard angioplasty balloon. Balloon 620 may comprise a compliant or non-compliant balloon having folds to facilitate reconfiguring the balloon from a radially expanded, inflated configuration to a low profile configuration, particularly for repositioning or removal after use. In a preferred embodiment, balloon 620 is comprised of a compliant material and is inflated to a pressure of 6 atmospheres or less.

Delivering radiofrequency energy directly to a specimen requires a monopolar or bipolar pathway. In a monopolar configuration there is a single pole or electrode from which the energy emanates and a grounding plate or pad to absorb the energy and complete the circuit. This configuration creates higher energy densities at the electrode than at the grounding pad, resulting in a single affected area or treatment zone at the electrode that is directly related to the geometry of the electrode and the power applied to the electrode. As the surface area of the monopolar electrode increases, so does the size of the treatment zone. The bipolar configuration uses two poles or electrodes to set up an electric field between the electrodes thus creating a conduction path for the current to flow. Unlike the monopolar electrode configuration where only surface area is deterministic to the treatment zone, the bipolar electrode configuration has three determining factors: electrode separation, parallel length, and width; each of which have a separate and distinct effect on the treatment zone.

Taking into consideration the effect each determining factor has on the affected treatment zone, and the overall impedance as seen by the generator, the separation or distance between electrodes has the greatest effect, followed by parallel length and lastly electrode width. Electrode separation is governed by Coulombs law, where, at very close distances the impedance as seen by a generator is very small and as separation of the electrodes increases the impedance increases at a rate that is proportional to the square of their separation. As this separation increases, a higher potential energy is generated due to the increase in impedance creating a greater flux density that results in a greater treatment depth. The effect of increasing the parallel length shared by the two electrodes causes the treatment zone to increase only as much as the parallel electrode length is increased. There are no additional depth effects only an increase due to added length. This additional length causes the impedance as seen by the generator to decrease due to the increase in potential parallel paths for the current to flow through. Electrode width has the least effect on the treatment zone and is governed by the same laws as electrode separation. As the width of the electrode is increased incrementally, the added effect is small due to the inverse square law for each incremental element placed on the outer edges of the existing electrode elements. Although this effect may be small it aides in reducing the surface heat generated by reducing the current density at the inside edge of the electrode pairs. This effect is amplified as the conductance of the electrode material approaches the conductance of the tissue being treated due to the path of least resistance becoming the tissue rather than the electrode itself.

Figure 33A:
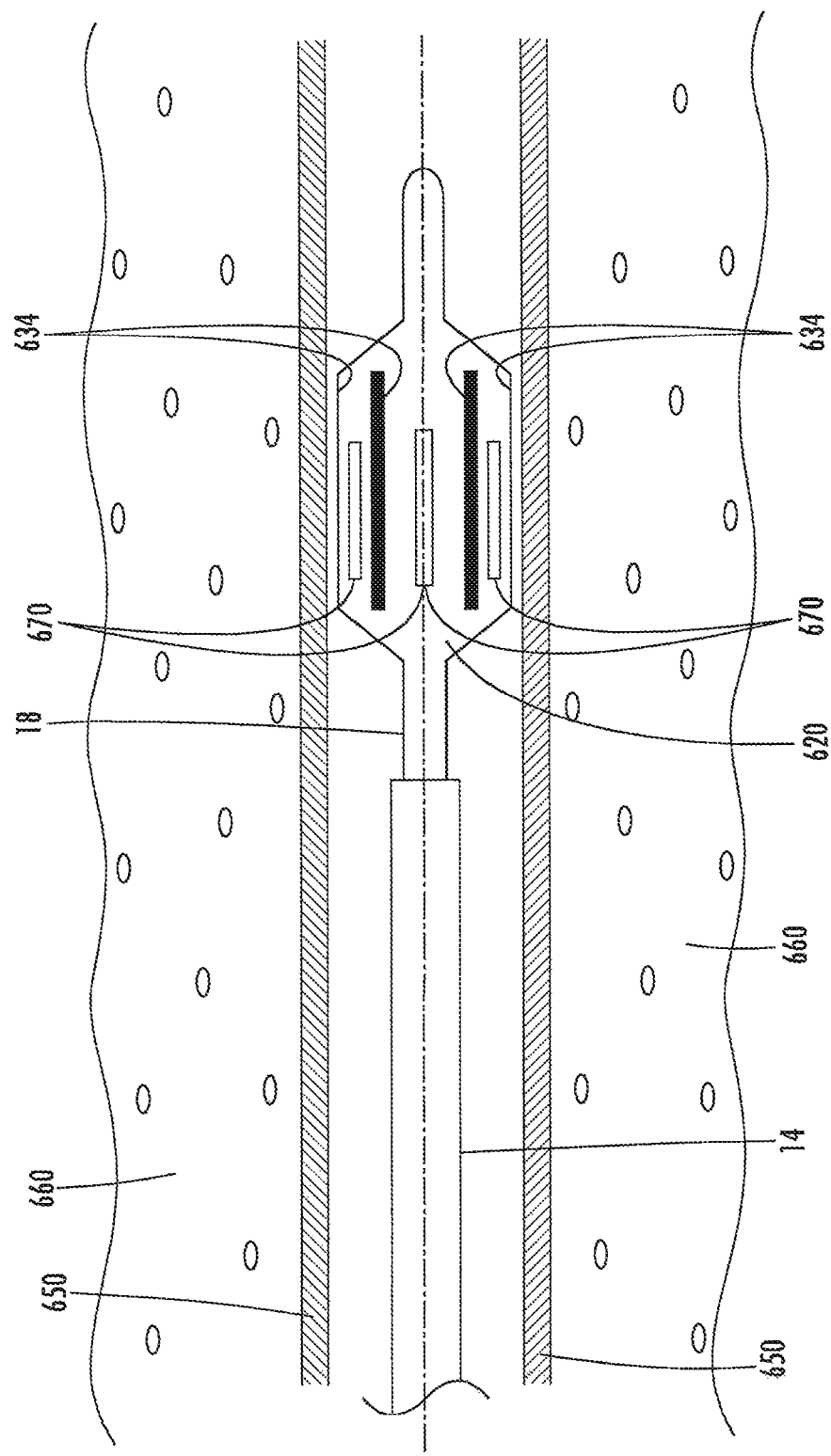
FIG. 33A schematically illustrates the system of FIG. 33 positioned to deliver energy to tissues proximate to a body lumen.

Referring to FIGS. 33 and 33A, catheter body 14, with distal end 18 and balloon 620, of catheter system 10 is positioned within a body lumen such that electrodes 634 may deliver energy to tissues proximate to electrodes 634 such as the tissues of the luminal wall 650 and tissues adjacent the luminal wall 660. The type and location of tissues 650 and 660 may be of any type found within proximity of a body lumen up to a distance of about 1 cm or more with the most preferred distances being approximately within about 5 mm or less.

Referring now to FIGS. 35A-35F, atherosclerosis (FIG. 35A) is a common form of tissue disease affecting the arterial luminal wall 650, resulting in a greatly reduced luminal diameter 651 or a completely occluded lumen (not shown). One of ordinary skill in the art will recognize that luminal wall 650 is comprised of the intimal, medial, and adventitial layers, and may be further comprised of many cellular and/or tissue states and types as it may relate to the specific anatomical location and/or biological process desired to be treated by the delivery of therapeutic energy.

Figure 35A:
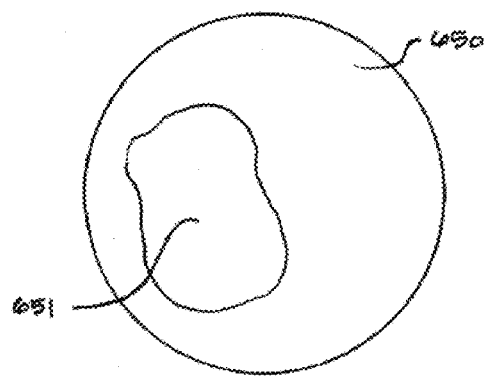
FIG. 35A is a cross sectional view of a body lumen with occlusion.
Figure 35B:
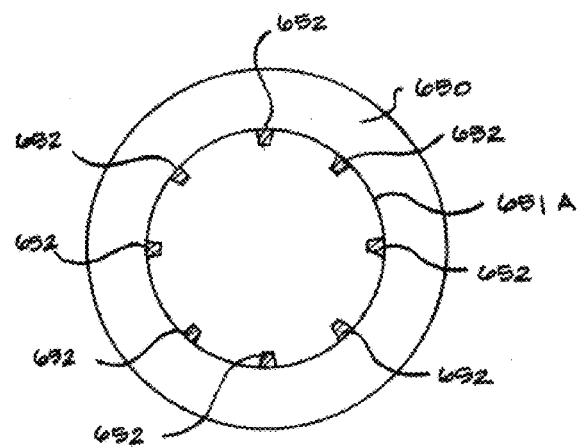
FIG. 35B is a cross sectional view of the body lumen of FIG. 35A following a dilation procedure and the implantation of a stent.

As illustrated in FIG. 35B, angioplasty and the implantation of a stent structure 652, results in the restoration of blood flow by acutely establishing an increased post-procedure lumen 651A. Angioplasty and stent implantation is a well-established means for treating arterial stenosis, however, restenosis of the treated lumen frequently occurs as a byproduct of a biological cascade that may develop in response to the angioplasty procedure.

Restenosis involves the growth of new tissue within the arterial wall caused by a biological cascade mechanism of platelets, polymorphonuclear leucocytes, and macrophage aggregation leading to the migration of smooth muscle cells from the media to the intima coupled with smooth muscle cell proliferation at the intimal layer. The acute onset of in-stent restenosis begins with relocation of plaque and reorganization of thrombus, in conjunction with an acute inflammatory response to injury of the endothelium that promotes fibrin and platelet deposition. Leucocytes gather in and around the injury caused by balloon dilation and stent implantation. As the biological cascade continues, leucocyte recruitment is further sustained. As the in-stent restenosis process continues, smooth muscle cells in the medial layer modify and migrate from the medial layer to the intimal layer before further proliferating as neointimal tissue. The volume of stenotic neointimal tissue is increased by smooth muscle cell synthesis of extracellular matrix predominantly comprised of proteoglycans and collagens.

FIGS. 35C, 49A, 50A, and 51A illustrate how in-stent restenosis may result in a subsequent reduction of the treated lumen. As a result of the biological process described above, the post-procedure lumen diameter 651A is reduced to lumen diameter 651B. Although stent structure 652 remains intact, the proliferation of cells in luminal wall 650 completely surrounds stent structure 652 rendering it ineffective in maintaining luminal patency. The combination of restenosis and the presence of an implanted stent provides several challenges to effective treatment. Reperforming angioplasty is unlikely to be effective because the restenosis may be the result of localized trauma caused by the original angioplasty procedure. Moreover, there is risk that the implanted stent structure 652 may be damaged during a second, in-stent angioplasty procedure. Mechanical ablation procedures are an alternative to angioplasty for treatment of in-stent restenosis, however, mechanical ablation may often result in further tissue trauma and also present the potential for causing damage to stent structure 652. Thermal ablation is an additional alternative to angioplasty, however, the high temperatures associated with ablative removal of tissue may also result in tissue damage and the eventual restenosis of the lumen as a result of the thermal trauma in tissue adjacent to the ablation site. Therefore, a means and procedure for thermally debulking the in-stent restenosis that avoids traumatic thermal damage to adjacent tissues in the luminal wall 650, and that avoids damage to stent structure 652, presents an advancement over the treatment means presently available.

Referring now to FIG. 35D, balloon 620 of the catheter system 10 in FIG. 33 is shown in a state of inflated contact with luminal wall 650 at a diameter approximate to restenosed diameter 651B (FIG. 35C). The balloon pressure is sufficient to provide electrical contact between electrodes 634A-634F and luminal wall 650 such that an energy path 653 may be established between the various electrodes 634A-634F, as may be desired. A first analysis of tissue may be made by applying energy through energy paths 653 using bursts of energy in a range of frequencies to measure impedance, by using other imaging modalities such as IVUS or the like as described herein, or by using impedance analysis and imaging in combination. For illustrative purposes, balloon 620 is shown with a plurality of electrodes 634A-634F, however, any number of electrodes may be distributed about the circumference of balloon 620. Additionally, energy paths 653 are for illustrative purposes shown between specific electrodes but may also be formed between any electrodes forming a pair using monopolar configurations, bipolar configurations, and bipolar configurations with electrode multiplexing. This arrangement creates an energy path 653 through the tissue that delivers energy or heat ("tissue remodeling energy") in particular treatment zones or segments of tissue between the electrode pairs 634A-634F ("remodeling zones" or "treatment zones") having a volume between the electrode pairs at a specific depth. Using different combinations of electrode pairs may reduce or eliminate gaps between the remodeling zones by using overlapping pairs.

By using pairs of electrodes 634A-634F in a bipolar system, tissue remodeling energy will go through one or more of non-target tissue, target tissue, or a combination of both non-target and target tissues between the electrode pairs in the remodeling zones. Any number of electrode pairs may be used in different patterns or arrays to create a number of remodeling zones. The controller 49 (FIGS. 2 and 33) may apply either constant power, constant current, constant voltage, or regulate to a constant temperature whichever has the most advantage. A therapeutic dose of energy may be applied to luminal wall 650 to cause shrinkage and remodeling of the in-stent restenosis using the heating and control methods described herein such that the target tissue may be debulked through the application of energy while the heating of a non-target tissue is avoided to a degree that may result in tissue trauma and further subsequent luminal stenosis.

Referring now to FIG. 35E, the thermal treatment of the in-stent restenosis is shown in-progress. Balloon 620 may be further increased in diameter to maintain tissue contact with luminal wall 650 but pressure in balloon 620 is not used as the means of luminal dilation. As the electrodes 634 of balloon 620 continue to deliver therapeutic energy along paths 653, the previously occlusive tissue of luminal wall 650 shrinks, resulting in a restoration of luminal patency. As patency is restored, the stent structure 652 may begin to be exposed. Because electrodes 634A-634F may be selectively energized, certain specific electrodes may either cease to be energized or may not be selected for energizing depending on the degree of proximity or actual contact between an electrode 634 and stent structure 652. As illustrated, electrode pair 634F and 634A, have ceased to be energized because of the point of CONTACT between electrode 634A and stent structure 652. As an alternate example, electrode 634E and 634F may be selected to be energized until actual contact between electrode 634F and stent structure 652 occurs, or may cease to be energized because electrode 634F is sufficiently proximate to stent structure 652. Electrode pair 634D and 634E and electrode pair 634B and 634C may continue to be energized until reaching actual contact or sufficient proximity to stent structure 652. The change in impedance in the electrical circuit formed by electrode pairs along energy paths 653 may be used to determine the proximity of stent structure 652 to an electrode 634 and may be used to selectively energize electrodes 634A-634F based on tissue characterization prior to and/or during treatment.

Referring now to FIG. 35F, the resultant luminal diameter 651C following the thermal treatment for the pervious in-stent restenosis by luminal wall 650 is increased from the previous diameter 651B (FIG. 35C). For the purposes of illustration, lumen 651C is shown to be roughly equivalent to the inner diameter of stent structure 652. The final diameter of the lumen may be any preferred diameter based on energy delivery, tissue temperature control, physician selected requirements, and the like.

The method for treatment of in-stent restenosis may further be comprised to include the treatment of lesions beyond the stented portions, or between stented portions, of a blood vessel using the same energy delivery and tissue treatment devices and methods described herein. This may be of particular advantage in the case of diffuse arterial disease where it may be common to have sections of an artery with in-stent stenosis, stenosis between stents, and/or stenosis along a significant portion of the arterial length.

In one preferred example of thermal treatment of in-stent restenosis using the physical embodiments of the present invention, a balloon is inflated to a pressure sufficient to cause electrical contact between luminal tissue and electrodes. Balloon pressure may be about 20 atmospheres or less, more preferably about 10 atmospheres or less, and most preferably about 6 atmospheres or less. Using the illustrative electrode arrangement of FIG. 35D, the electrode pairs 634F and 634A, 634B and 634C, 634D and 634E are energized with about 4 Watts of power for about 2 seconds. An alternate electrode paring of 634A and 634B, 634C and 634D, 634E and 634F are subsequently selected and energized at about 4 Watts of power for about 1 second. The target tissue is provided a therapeutic remodeling energy of about 65° C. or less.

The controller 49 (FIGS. 2 and 33) may energize the electrodes with about 0.25 to 5 Watts average power for 1 to 180 seconds. Higher energy treatments may be performed at lower powers and longer durations, such as 0.5 Watts for 90 seconds or 0.25 Watts for 180 seconds. Using a wider electrode spacing, it would be appropriate to scale up the power and duration of the treatment, in which case the average power could be higher than 5 Watts, and the total energy could exceed 45 Joules. Likewise, using a shorter or smaller electrode pair would require scaling the average power down, and the total energy could be less than 4 Joules. The power and duration are calibrated to be less than enough to cause severe damage, and particularly less than enough to ablate diseased tissue 48 within a blood vessel. Suitable methods and devices for adaptation and/or use in the present system may also be described in U.S. Pat. Nos. 5,098,431; 5,749,914; 5,454,809; 4,682,596; and 6,582,423, among other references; the full disclosure of each of these references is incorporated herein by reference.

Different tissue types have different characteristic electrical impedances that cause the tissue to absorb energy of certain frequencies or frequency ranges more readily than others. By applying energy at the specific frequency or range of frequencies that the tissue is more conductive, energy penetrates the tissue more readily. Frequency targeting seeks to deliver more energy to the targeted tissue by determining the frequency or range of frequencies at which the impedance of the targeted tissue is equal to or greater than that of non-target tissue, such as by operation at or below a threshold frequency. For example, energy delivered at a specified frequency or range of frequencies may cause more heat to be dissipated in a collateral tissue than energy delivered outside of those specific frequencies.

Figure 25:
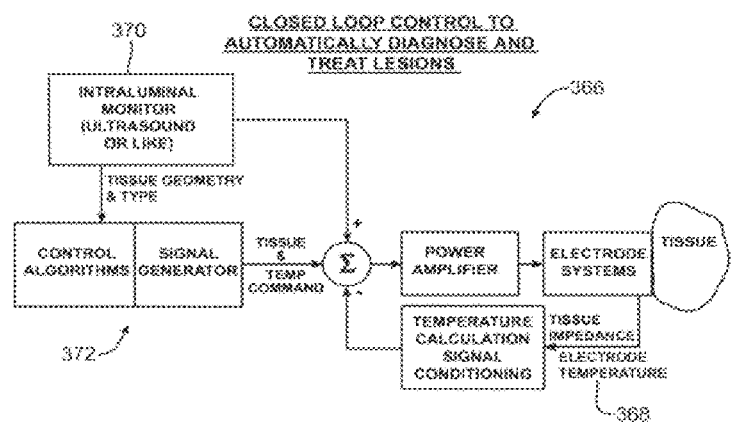
FIG. 25 illustrates one embodiment of a closed loop control system to automatically diagnose and treat lesions within a vessel utilizing tissue information from an external source such as IVUS.

Closed loop control can be understood with reference to FIG. 25. Impedance measurements over frequency ranges and across multiple electrodes may be utilized to verify electrode location relative to tissue landmarks, optionally by correlation to companion intraluminal measurement devices such as IVUS prior to and during therapy. Data about the condition of the tissue, optionally including temperature change, electrode to tissue interface impedance, tissue impedance, electrode to tissue or blood contact, and intraluminal geometry and tissue type from ultrasound or other sources, can be utilized by a controller as inputs to a closed loop control system 366.

Figure 42:
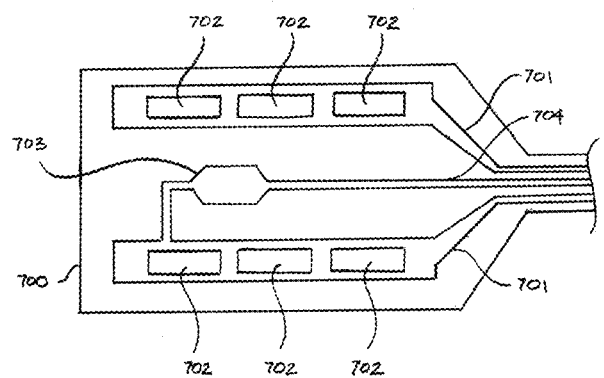
FIG. 42 is a schematic view of an electrode configuration with temperature sensing means.
Figure 43A:
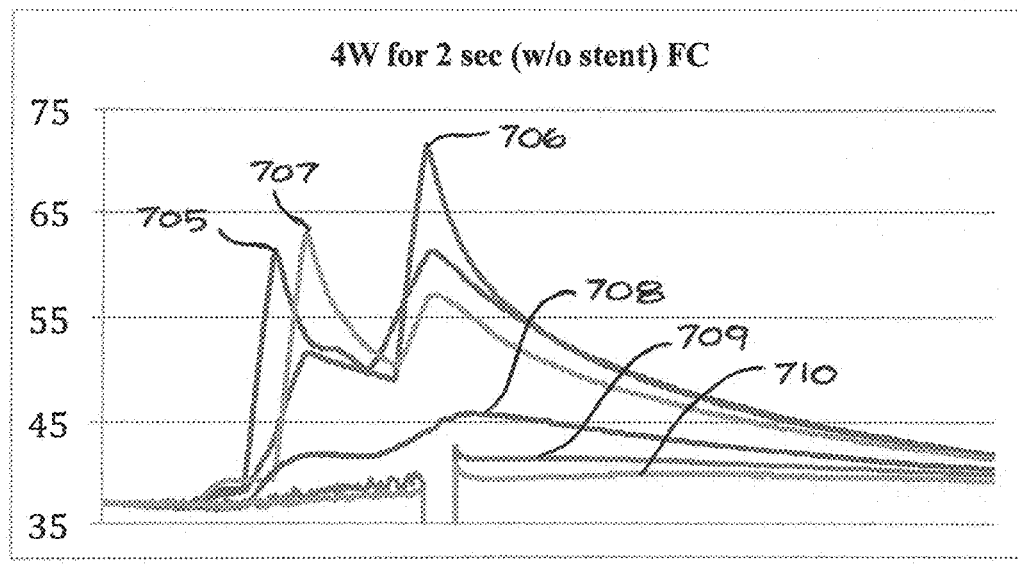
FIGS. 43A and 43B are temperature plots for full-circumferential energy delivery of 4 Watts for 2 seconds, without and with an implanted stent, respectively.
Figure 43B:
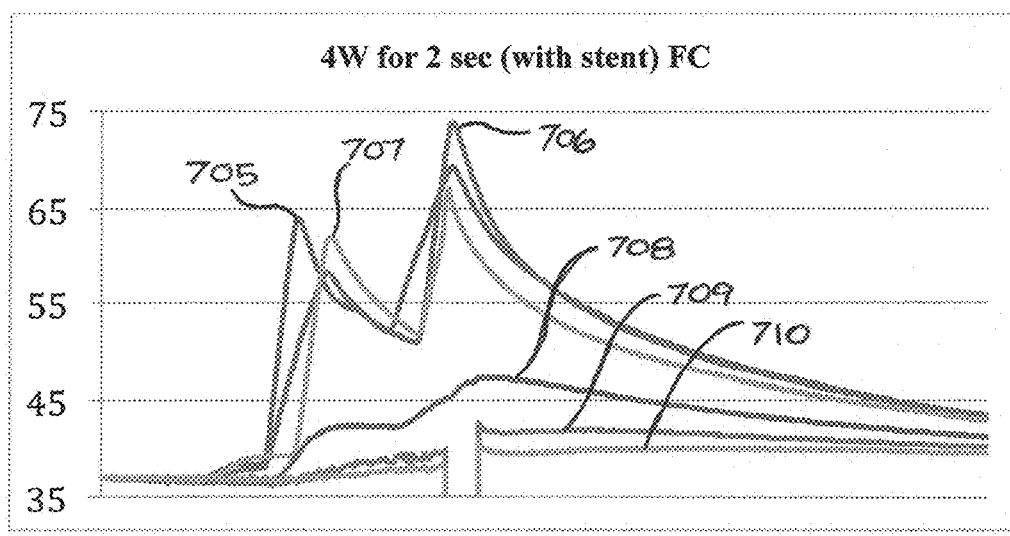
Figure 44A:
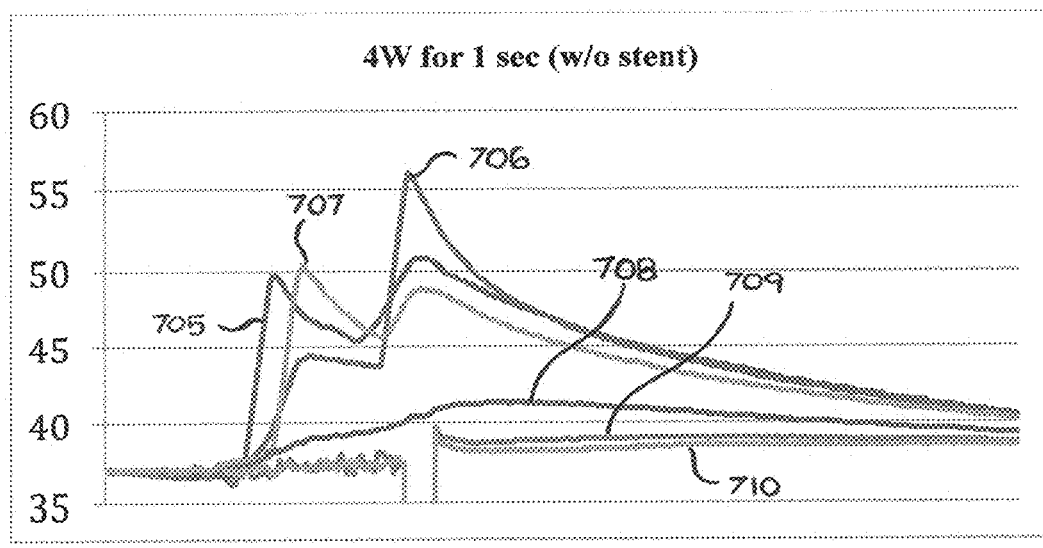
FIGS. 44A and 44B are temperature plots for full-circumferential energy delivery of 4 Watts for 1 second, without and with an implanted stent, respectively.
Figure 44B:
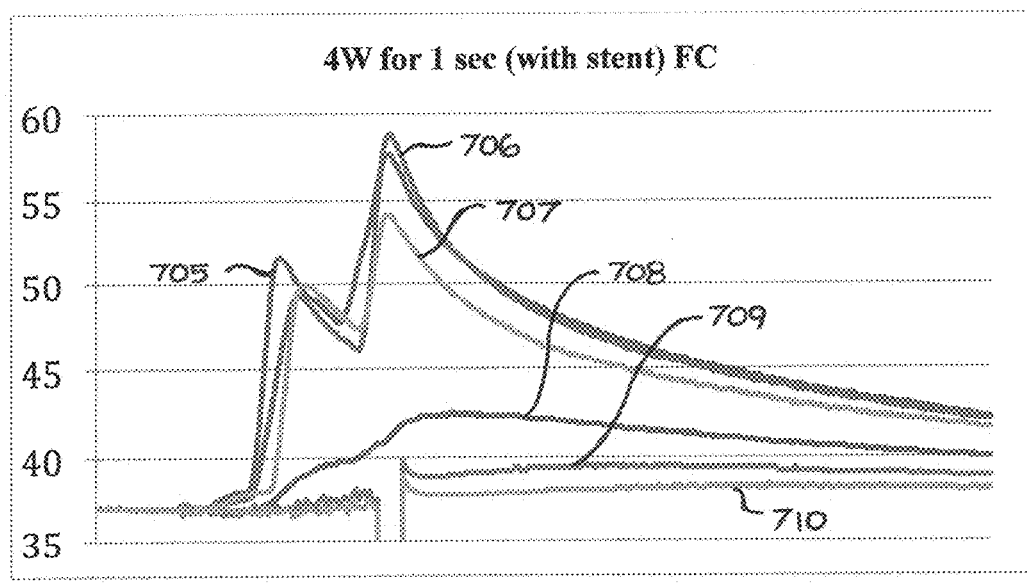
Figure 45A:
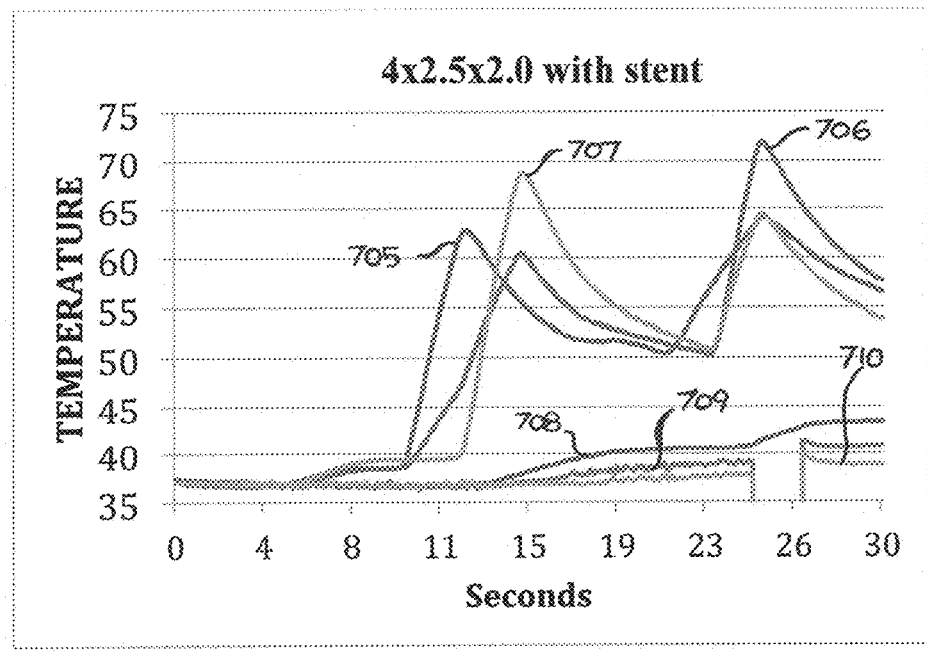
FIGS. 45A and 45B are time-temperature plots for energy delivery of 4 Watts for 2.5 seconds followed by 4 Watts for 1.5 seconds, without and with an implanted stent, respectively.
Figure 45B:
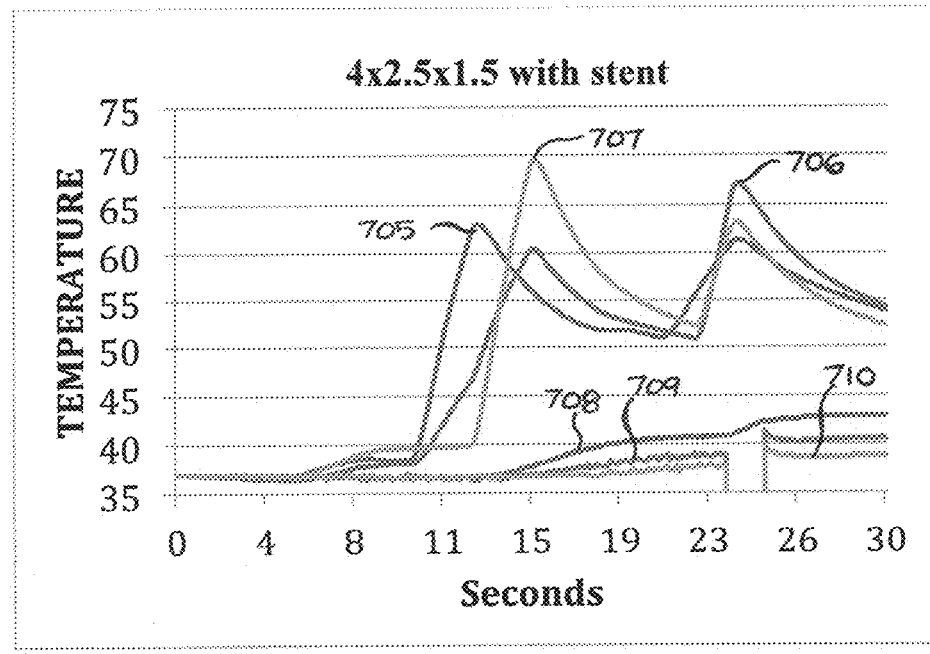
Figure 46:
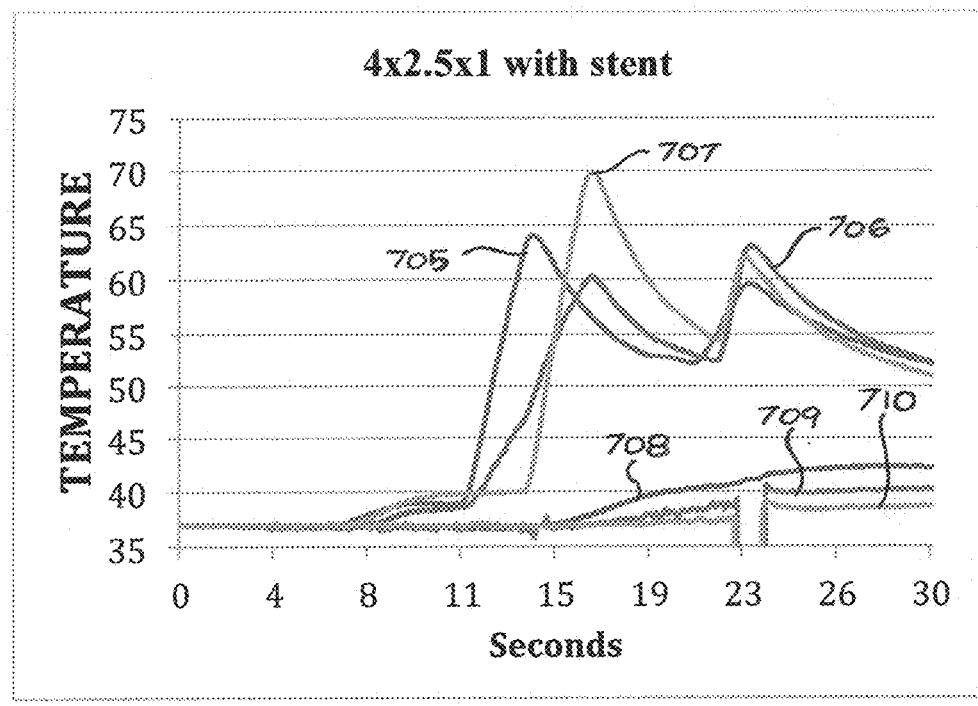
FIG. 46 is a time-temperature plot for energy delivery of 4 Watts for 2.5 seconds followed by 4 Watts for 1 second with an implanted stent.
Figure 47:
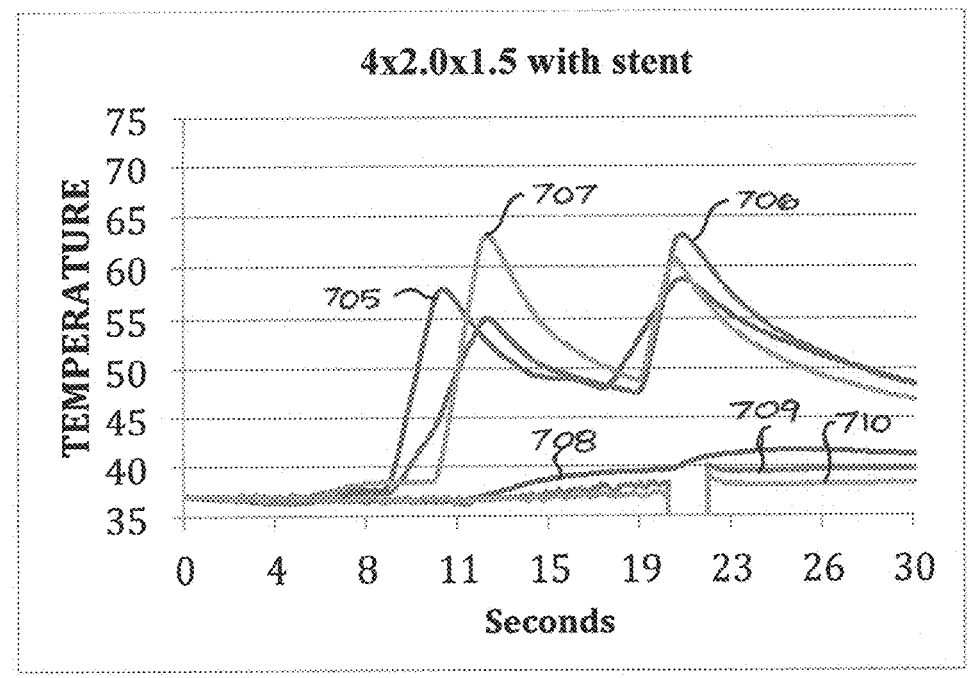
FIG. 47 is a time-temperature plot for energy delivery of 4 Watts for 2.5 seconds followed by 4 Watts for 1.5 seconds with an implanted stent.
Figure 48:
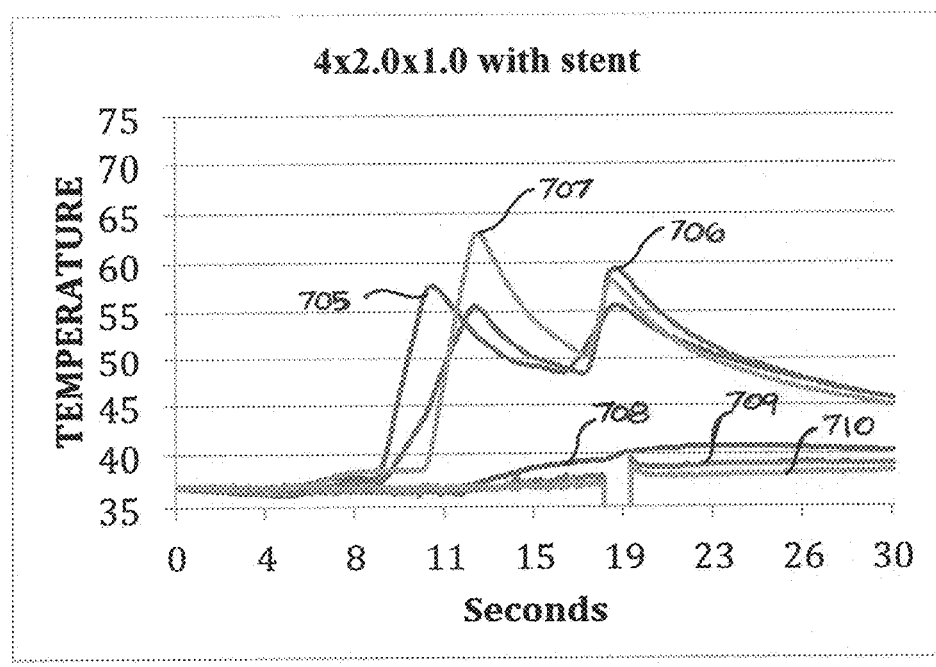
FIG. 48 is a time-temperature plot for energy delivery of 4 Watts for 2 seconds followed by 4 Watts for 1 second with an implanted stent.

Referring to FIGS. 33-35F, energy delivery may be controlled through the use of closed loop control by controller 49 (FIGS. 3, 33) used to regulate energizing of electrodes 634. Most typically the power generator 642 may be controlled to vary voltage such that constant power output is achieved; alternately current may be varied. Further, control loop variables may be selected from one or more of the variables power, impedance, impedance phase angle, and temperature.

Where power is used as a regulated parameter, voltage and current may be measured and voltage may be modulated to achieve a relatively constant power output within a tolerance according to a preset or defined power set point. Optionally the phase angle difference between voltage and current may be included in the power calculation to make power factor corrections based on the phase angle difference. Where impedance is used as a regulated parameter, measured changes in impedance based on changes in tissue temperature and/or tissue state may be used to define a threshold at which power may be halted or allowed to continue where power is modulated to maintain the defined impedance within a tolerance for a period of time.

Where temperature is used as a regulated parameter, an optional temperature sensor 670 or 703 (as shown by FIG. 33A and FIG. 42 respectively) comprised of a thermocouple, thermistor, infrared sensor, or the like, may be used to measure temperature where a defined temperature or temperature range may be used in conjunction with power modulation to maintain temperature in proximity to the sensor 670 or 703 within a temperature range. In one electrode embodiment of the present invention, shown in FIG. 42, one or more of electrode 700 may be mounted to a balloon, such as that of balloon 620 (FIG. 33A), wherein electrodes 700 are comprised of flex circuits further comprised to include electrode conductors 701, a plurality of energy delivery surfaces 702, and a temperature sensing means 703 with conductor 704. Temperature sensing means 703 may be comprised of a thermistor, thermocouple, infrared sensor or the like and may send measurement information to a power control loop through conductor 704. The electrode 700 may be comprised to include radiopaque material, with one preferred approach being a conductive radiopaque material such as gold, platinum, or the like being used to comprise one or more of the plurality of energy delivery surfaces 702. The number and pattern of distribution for electrodes 700 about balloon 620 may be any pattern that provides for a sufficiently uniform means to deliver energy to the tissue treatment zones while avoiding substantial thermal damage to collateral tissue. To aid in the flexibility of the circuit and to aid in minimizing the unexpanded balloon profile, conductors 701 and 704 may be comprised of a substrate that has a thickness as low as about 0.0005 inches with a conductive layer as thin as 0.5 ounces per square foot. One or more surfaces of electrode 700 may be comprised of a polymer for the purpose of adhesion to balloon 620 and/or to provide a barrier between conductors 701, 704 and tissue.

One or more of voltage, current, impedance, and temperature may be used as closed loop control parameters. For example, current may be a closed loop control parameter where power is delivered in the proximity of highly conductive materials, such as metallic stents. In this case it may be prudent to limit current, such as by stopping power delivery when the impedance is at or below a certain/predetermined/predefined level. Or, in the case of a power-limited control algorithm (which will increase current when impedance drops) one may additionally limit the maximum current that is delivered at or below a certain/preset impedance level. This method has the effect of reducing power as impedance falls below a certain/preset threshold. Optionally, one or both of pulse width modulation of energy, and amplitude modulation of energy may be comprised within the means of control. In some instances, the impedance of a stent may vary enough by the nature of its composition (e.g. cobalt chromium versus nickel titanium, polymer, polymer coating, etc.) so as to provide for a range of impedances that may indicate contact with, or proximity to a stent. In some embodiments, impedance may be used to identify the nature of the implanted stent and/or tailor energy delivery accordingly by comparing the known baseline electrical characteristics of unstented neointimal stenotic tissue and comparing those characteristics to that of in-stent stenotic tissue such that measured differences may be attributable to the nature of the implanted stent, whereby the processor and generator may apply control parameters accordingly by taking into account the presence of the stent. In some embodiments, a table of known electrical characteristics of known stent types may be incorporated into energy delivery control algorithms such that an energy delivery profile may either be automatically selected by tissue analysis, or by operator selection. In embodiments where energy delivery may expressly compensate for the nature of an implanted stent, energy delivery may be controlled to avoid thermal damage to stents having temperature-sensitive attributes such as materials of composition, coatings, and the like.

Referring to FIG. 25, impedance measurements using a closed loop treatment controller 366 making use of hardware and/or software of the system processor may facilitate treatment control. Such control over frequency ranges and across multiple electrodes may be utilized to monitor and to verify physical changes such as tissue shrinkage or denaturing of tissue in the application area. This data may be utilized to verify physical changes observed by other intraluminal observation techniques such as ultrasound. Data from impedance measurements 368 combined with inputs from intraluminal measurement devices 370 such as ultrasound can be used to determine electrode selection from a predetermined set of rules of a controller or processor module 372. This type of control system may also be utilized in an automatic mode to diagnose and treat diseased intraluminal tissue, in-stent restenosis, or other such targeted tissue, or to identify and direct energy to a target tissue proximate to a lumen.

Figure 26A:
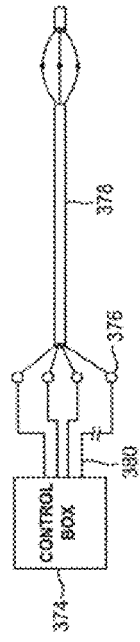
FIG. 26A illustrates the switching mechanism in an external control box.
Figure 26B:
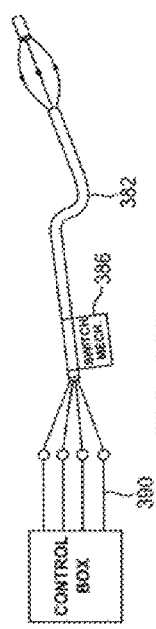
FIG. 26B illustrates the switching mechanism at the distal end of the catheter.
Figure 26C:
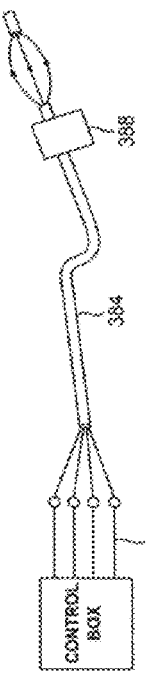
FIG. 26C illustrates the switching mechanism at the proximal end of the catheter.

Implementation of electrode switching may employ any of a wide variety of selective energizing electrode circuits, switch types, switch locations, and the like, some of which are schematically illustrated in FIGS. 26A-26C. Electrode switches can be located in an external instrument or external control box 374, so that one external connector point 376 is provided for each electrode of catheter 378, with one wire per electrode 380 extending to, in and/or along the body of the catheter. Alternatively, electrode switch mechanisms 386, 388 may be embedded in a catheter 382, 384, respectively, either near the proximal end of the catheter for external switching or near the distal end of the catheter for internal switching. A limited number (e.g., 4) wires 390 may run proximally of the switching mechanism, while one wire per electrode may extend distally of the switching mechanism. Connection of discrete electrodes to radiofrequency generator or impedance measuring device can be accomplished by either electromechanical or solid state means.

Switching mechanisms disposed at distal end of catheter may have advantages. If located on the catheter, the switching mechanism can be located at the distal end to decrease the number of wires in the body of the catheter or at the proximal end. In embodiments of switching mechanism located at distal end of catheter the external control circuit optionally communicates with the switching mechanism via the same wires used for impedance measurements. Switching mechanism at the proximal end or other location on catheter may also be employed. The switching mechanism can be located at proximal end or any other location on the catheter if it provides advantage in performance or cost.

Where energy is delivered to a plurality of electrodes 634 (FIGS. 34, 35D) at the same time, electrodes 634 may be powered and controlled either by separate, independent circuits having their own control loops, or by firing one or more electrodes 634 sequentially in time, using the same circuit, in which case the control loop is also closed sequentially.

FIGS. 13-17B show histological results of testing done in animal studies. FIG. 13 shows the application of 1 Watt for 8 seconds post-operatively at seven days, which had a maximum surface temperature of 50° C. in bench top testing, showing mild shortening of smooth muscle at the sites of inserted arrows. FIG. 14 shows the application of 2 Watts for 2 seconds post-operatively at eight days, which also had a maximum surface temperature of 50° C. in bench top testing. FIGS. 15A, 15B show the application of 4 Watts for 1 second at seven days and FIG. 15C post-operatively at thirty days. There are obvious thermal applications corresponding to each electrode (black arrows). There also appears to be thermal alterations to some of the collagenous areas of the vessel wall. This suggests bulk tissue temperatures just slightly over 60° C. FIGS. 16A, 16B show the application of 2 Watts for 4 seconds post-operatively at seven days, and FIG. 16C at thirty days. The slide shows heat therapy at each electrode-tissue interface (black arrows show edges of treatment zones). There is also a corresponding thermal effect deep into the collagenous areas, and gross observations of tissue shrinkage. The figures also show some thermal diffusion into the tissue in between treatment zones that also resulted in collagen denaturing. This indicates that the local areas of heat deposition under the electrodes may have reached 70° C. or higher. Of course, there is a temperature gradient that slopes off in between electrodes and radially away from the electrodes, and deeper into the vessel and surrounding tissue. FIG. 17A shows the application of 3 Watts for 2 seconds post-operatively at seven days and FIG. 17B at thirty days.

In one aspect of the present invention, catheter system 10 may be used to treat luminal target tissues additional to or different than in-stent restenosis as may be understood by referring to FIGS. 7A through 7E. For the purposes of description, the target tissue in the following discussion will be atherosclerosis not located in the stented portion of a body lumen, however, the method of treatment can be understood to represent the method for delivering a therapeutic dose of energy to any target tissue proximate to a luminal wall. In some instances it may be desirable to treat stenotic locations along a lumen where some are in-stent and others are external to the stent, as it is common for diffuse artery disease to not be localized to a stented location. Additionally, the FIGS. 7A-7E show a basket for illustrative purposes; however, the expandable structure may be any of those encompassed by the present invention. As seen in FIG. 7A, accessing of a treatment site will often involve advancing a guidewire GW within a blood vessel V at, and more often distally beyond a target region of atherosclerotic material AM. A wide variety of guidewires may be used. For accessing a vessel having a total occlusion, guidewire GW may comprise any commercially available guidewire suitable for crossing such a total occlusion, including the Safe-Cross™ radiofrequency system guidewire having forward-looking optical coherence reflectometry and radiofrequency ablation. Where atherosclerotic material AM does not result in total occlusion of the lumen, such capabilities need not be provided in guidewire GW, although other advantageous features may be provided. For example, guidewire GW may include a distal balloon to hold the guidewire in place and further inhibit movement of ablation debris and the like. Guidewire GW may be positioned under fluoroscopic (or other) imaging.

Catheter 12 is advanced distally over guidewire GW and positioned adjacent to atherosclerotic material AM, often toward a distal portion of the occlusion as can be understood with reference to FIGS. 7A and 7B. Expandable structure 26 expands radially within the lumen of the blood vessel so that electrodes 50 radially engage atherosclerotic material AM. Expandable structure 26 may be expanded by, for example, pulling a pullwire extending through catheter body 14 to the coupled (directly or indirectly) to distal portion 62 of expandable body 26 (see FIG. 4). Alternatively, an inner catheter body 58 may be moved proximally relative to outer catheter body 14, with the inner catheter again being coupled to the distal portion of the expandable body. Still further alternatives are possible, including withdrawing a sheath from around the expandable body and allowing the expandable body, basket 26 (FIG. 2) to flex radially outwardly, or, by inflating balloon 620 (FIG. 33). In at least some embodiments, whether actuated from the proximal end of catheter 12 or simply by releasing the expandable body, the structural members defining the expandable body may comprise elastic or superelastic materials treated to expand radially outwardly, such as by heat-setting a superelastic Nitinol™ metal, polyimide, or the like. In some embodiments, guidewire GW may be removed after the ablation catheter is positioned and/or the expandable body is expanded. As atherosclerotic material AM is distributed eccentrically about catheter 12, some of electrodes 50 directly engage a luminal wall W, as can be understood with reference to FIGS. 7B and 7C.

Imaging catheter 34 is positioned within a lumen of catheter 12 so that detector 42 extends to adjacent atherosclerotic material AM. The imaging catheter operates within and/or through catheter 12 so as to measure a thickness of atherosclerotic material concentrically about catheter 12 as illustrated in FIG. 7C with measurements often being taken at a plurality of axial locations so as to measure axial variation of the atherosclerotic material AM within the blood vessel, such measurements often progressing proximally. In many cases, atherosclerotic material AM will be distributed eccentrically within the vessel wall as shown in FIG. 7C. It should be noted that no portion of the vessel wall need be completely uncovered by atherosclerotic material for the measurement distribution to indicate that the obstruction is eccentric, as a relatively thin layer of atheroma along one portion or side of the blood vessel may be much different in thickness than a very thick layer of atherosclerotic material on an opposite side of the blood vessel V. In some methods, remodeling and/or ablation of all atheroma along one side may result in electrode/vessel wall engagement only after treatment begins.

In some cases, imaging catheter 34 may allow identification and/or characterization of in-stent restenosis, atherosclerotic materials, plaques, tissues, lesions, and the like from within a blood vessel. For example, imaging catheter 34 may determine an axial and/or circumferential localization of a stenosis for treatment. Where treatments are intended for full or partial stenosis of the lumen, so as to enhance blood flow through the lumen, the treatment may be tailored to provide short term and/or long-term increases in lumen diameter and blood flow. Catheter 34 may be used to provide information similar to that available through histology so as to indicate a composition of a target tissue (by identifying and location of, for example, a stent, smooth muscle cells, a lipid pool, calcifications, etc.) Intravascular ultrasound, optical coherence tomography, intravascular MRI antennas, and other catheter-based imaging systems, or non-invasive imaging modalities such as MRI systems, may be used.

Suitable imaging catheters for use in the present catheter system are commercially available from a wide variety of manufacturers. Suitable technology and/or catheters may, for example, be commercially available from SciMed Life Systems and Jomed-Volcano Therapeutics (providers of intravascular ultrasound catheters), Light Lab™ Imaging (developing and commercializing optical coherence tomography catheters for intravascular imaging), Medtronic CardioRhythm, and the like. Still further alternative technologies may be used, including ultra fast magnetic resonance imaging (MRI), and electrical impedance atheroma depth measurements, optical coherence reflectometry.

The systems, devices, and methods described herein may optionally make use of imaging techniques and/or tissue detector devices which are at least in part (optionally being entirely) disposed outside of the body lumen, optionally being disposed outside of the patient body. Non-invasive imaging modalities which may be employed include X-ray or fluoroscopy systems, MRI systems, external ultrasound transducers, and the like. Optionally, external and/or intravascular tissue detectors may also be used to provide temperature information. For example, a system having an MRI antenna may detect tissue temperatures such that a graphical indication of treatment penetration may be presented on the system display. Tissue temperature information may also be available from ultrasound and/or optical coherence tomography systems, and the temperature information may be used as feedback for directing ongoing treatments, for selecting tissues for treatment (for example, by identifying a hot or vulnerable plaque). Additionally, as shown in FIG. 33A and FIG. 42, one or more temperature sensors 670 or 703 may be mounted on the expandable structure 620 proximate to energy delivery surfaces 634 or 702 to provide tissue temperature sensing during the delivery of therapeutic energy dosages to the targeted tissue area proximate to a lumen.

As with positioning of guidewire GW and advancement of catheter 12, positioning of sensor 30 of imaging catheter 34 may be facilitated by fluoroscopic or other imaging modalities. Location of sensor 36 relative to expandable structure 26 may be facilitated by radiopaque markers of catheter 34 adjacent sensor 36, and by the radiopaque structure (or corresponding radiopaque markers placed on or near) expandable structure 26, and/or by the use of electrodes comprised to include radiopaque material. By way of example gold and platinum are two common radiopaque materials that may be desirable choices because they are also conductive, however, any biocompatible radiopaque material may be used.

By expanding expandable structure 26 within blood vessel V, optional proximal and distal barriers 66, 68 (see FIG. 4) may form an at least partially, and preferably a substantially isolated environment within the blood vessel. That environment may be adapted to improve subsequent remodeling and/or ablation by aspirating blood from a port of aspiration lumen 22 disposed between proximal and distal barriers 66, 68, and by irrigating the isolated environment with a desired fluid, as described above. When provided, aspiration and/or irrigation may be performed, optionally simultaneously, so as to generate a flow within the controlled environment for removal of any vaporization gases, ablation debris, and the like.

Figure 7D:
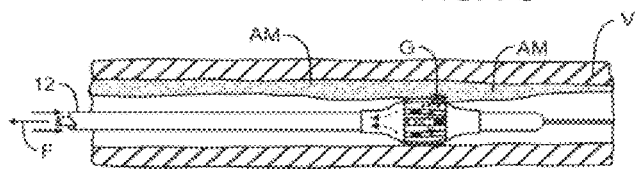

Referring now to FIGS. 7C and 7D, circumferential imaging often indicates that treatment energy should be targeted to an eccentric portion or region R of the vessel wall W. To aid in registering the electrodes with the circumferential target tissue distribution, one strut of expandable structure 26 has an identifiable image, allowing the strut to serve as a rotational alignment key. Alternately, a radiopaque marker may be used for an expandable structure comprising a balloon. Registering the electrodes may be achieved using intravascular imaging such as intravascular ultrasound (IVUS), optical coherence tomography ("OCT"), or intravascular MRI, optionally using external imaging such as fluoroscopy, magnetic resonance imaging ("MRI"), etc. Electronic registration may also be used. In response to this information, radiofrequency energy is directed to electrodes within region R. These actively energized electrodes define a subset of the overall array of electrodes, and selection of this subset of electrodes may be implemented using a controller as described herein.

Figure 7E:
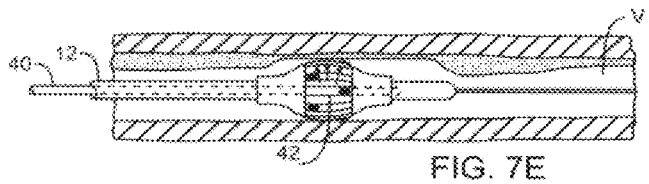

Referring now to FIG. 7E, as described above, it may not be necessary to completely remove all stenotic material from within the blood vessel. Providing an open lumen having an effective diameter of as much as 80% or more of a nominal native lumen diameter may be sufficient. Remodeling treatments may provide acute effective open diameters in a range from about 30% to about 50%. In some embodiments, thermal treatment caused to the target tissue with the energized electrodes or other energy directing surfaces may result in subsequent resorption of the target tissue so as to provide further opening of the vessel after termination of treatment through the healing process, as the data in Table 3 indicates.

In some embodiments, the expandable structure may remain expanded against the lumen wall W while the catheter 12 moves within the lumen (a blood vessel for example), the catheter often being drawn proximally during or between energy treatments. Alternatively, the expandable structure may be repeatedly contracted, axial movement of the catheter 12 employed to reposition the expandable structure, with subsequent expansion of the structure at each of a plurality of treatment locations along the targeted area proximate to the luminal wall. Repeated intravascular imaging or other measurements circumferentially about catheter 12 may be employed, with the energy often being halted temporarily so as to allow an image to be acquired intermittently during a procedure. A final image may be taken to verify energy treatment has been successful.

Figure 10:
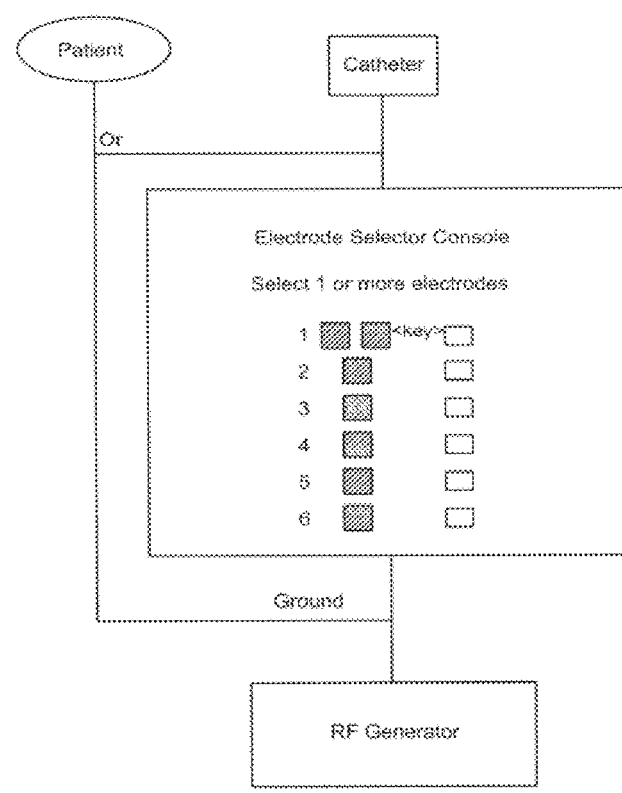
Figure 11:
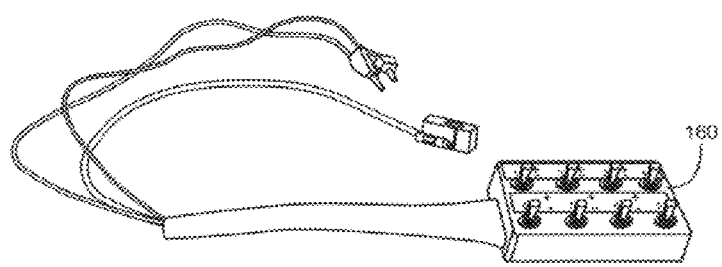
FIG. 11 illustrates an alternative controller for selectively energizing electrodes in the system of FIG. 2.

Referring now to FIGS. 8 and 9, alternative controllers 92a, 92b selectively energize electrodes of catheter 12 with radiofrequency power supplied from a radiofrequency generator 94. A wide range of radiofrequency energy types may be employed, including burst of 500 Khz, different types of waveforms, and the like. In controller 92a, a simple dial 96 is turned to point to a desired electrode pair to be energized. Optionally, a "key" electrode may be registered with the intravascular imaging system, either electronically or by providing an electrode, electrode support member, or attached marker that presents a distinct image on the intravascular imaging display. This simplifies selection of one or more eccentric electrode pair along a targeted area. Advantageously, catheter 12 need not be rotated into a proper orientation to accurately deliver therapeutic energy eccentrically to tissues proximate to the circumference of a lumen wall. Controller 92b includes similar capabilities, but allows the operator to select multiple electrodes for driving bipolar radiofrequency energy therebetween, providing greater flexibility in allowing multiple electrodes to be simultaneously energized. Monopole control arrangements similar to those of FIGS. 8 and 9 may also be employed, as can be understood with reference to FIG. 10. Patient grounding may be effected by a patient grounding plate, a ring electrode 2 to 5 cm proximal to basket 26, or the like. Once again, no catheter rotation is required to orient an active side of the catheter adjacent to the targeted tissue since various eccentric orientations can be selected through the electrode selection controller.

Figure 12A:
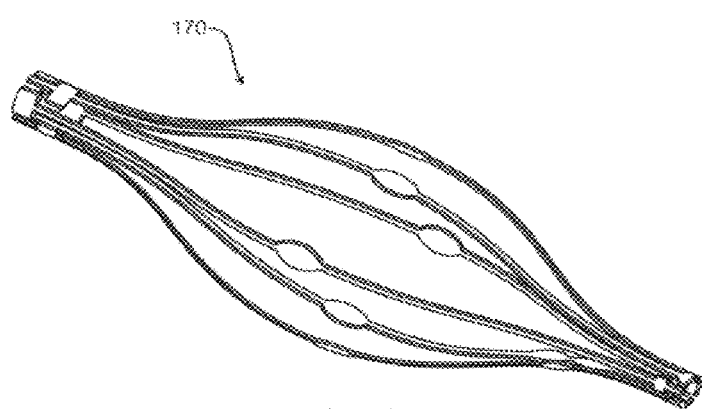
FIGS. 12A-H illustrate an alternative basket structure formed with independent struts having a localized enhanced width for use as an electrode surface, along with components thereof.
Figure 12B:
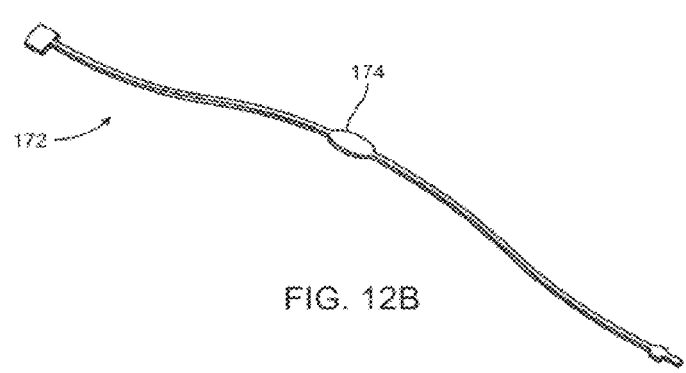
Figure 12C:
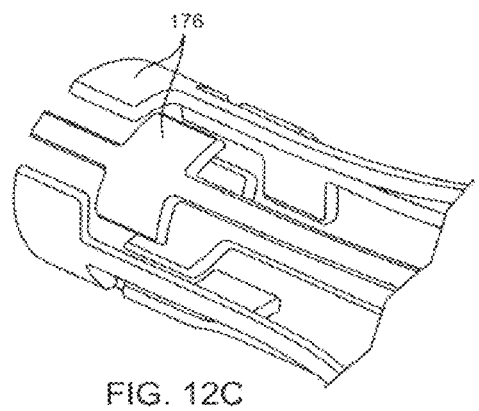
Figure 12D:
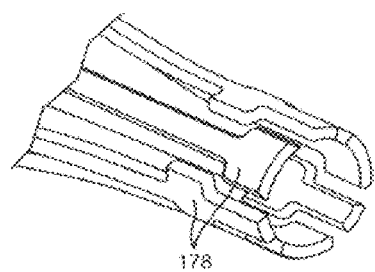
Figure 12E:
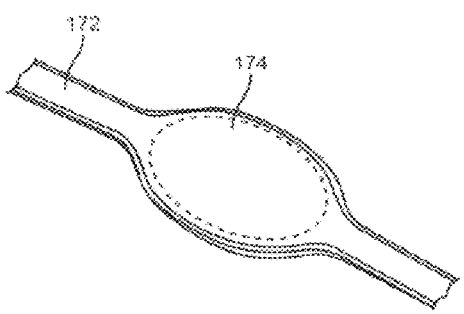

An exemplary self-expandable basket is illustrated in FIGS. 12A-12H. As can be understood from these drawings, electrodes may be fabricated as part of the struts 172 from which the basket is formed, for example, using a radially outwardly oriented surface of a localized widening 174 of each strut disposed in axially central portion of the strut, as can be seen in FIGS. 12B and 12E. Each arm may be formed from one piece of material, optionally comprising a Nitinol™ nickel-titanium shaped memory alloy, with the struts optionally being laser cut from a Nitinol™ tube. The electrode/basket may be, for example, coated with a high temperature polymer such as a polyimide. Electrodes 174 may be formed by inhibiting coating or removing coating from the desired portion of the associated strut 172 (as illustrated in FIG. 12E) so that the electrode surface is exposed for contact with tissue. At least the active electrode surfaces may be coated with a highly conductive metal such as gold, silver, an alloy of copper, or the like, and the coating will preferably maintain and withstand flexibility of the basket structure, with coating materials optionally being rolled or the like. By limiting the conductive electrode to a properly configured (often radially outwardly oriented), electrical coupling between the electrode and blood or other conductive fluids within the lumen may be limited. The struts may be separated from each other and structurally supported with an insulated material such as ultraviolet ("UV") cure or heat shrink sleeve, a polyethylene, Nylon™ to form basket 170. Many imaging modalities (including intravascular ultrasound, optical coherence tomography, intravascular MRI, and the like) may be at least in part blocked or degraded by positioning the image detecting structure within a metallic structure such as a basket formed of Nitinol™. Hence, there may be advantages in producing alternative expandable structures such as baskets comprising plastics or a polymer. Further, in light of the heat generated by the electrodes of the systems described herein, it may be advantageous for such polymer basket structures to comprise a high temperature polymer such as a polyimide. Alternative basket structures may comprise HDPE, PET, Nylon™, PEBAX™, and the like; the basket may be formed by cutting struts from a tube of the polymer material.

Figure 14B:
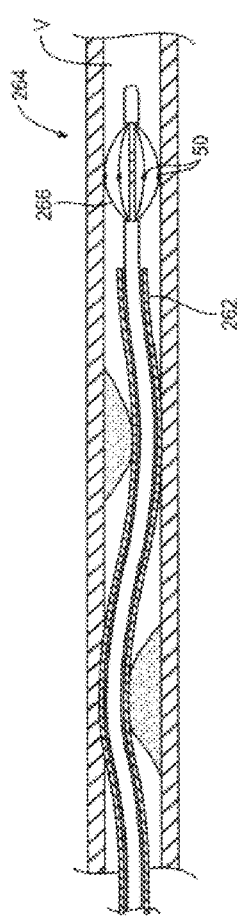

Exemplary treatment methods are illustrated in FIGS. 14A-14H. In FIG. 14A, the catheter system 260 includes a basket covering sheath 262 over an atherosclerotic material detecting and treating catheter 264 as described above. In this embodiment, outer basket sheath 262 radially restrains the basket 266, which is biased to expand radially when released from the outer sheath, as illustrated in FIG. 14B. In some embodiments, the basket may be expanded after the outer sleeve is retracted, such as by pulling pullwires, rotating one portion of the catheter relative to the other, or the like. Regardless, as the basket expands within the vessel V, electrodes 50 of the basket engage the surrounding vessel wall. An imaging transducer near basket 266 of an imaging catheter disposed in a lumen of the treatment catheter evaluates the vessel V, and the detection/treatment catheter system 264 is pulled proximally along the artery or vessel V.

Figure 12F:
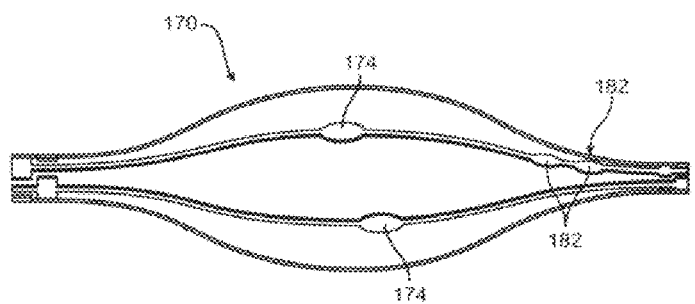
Figure 12G:
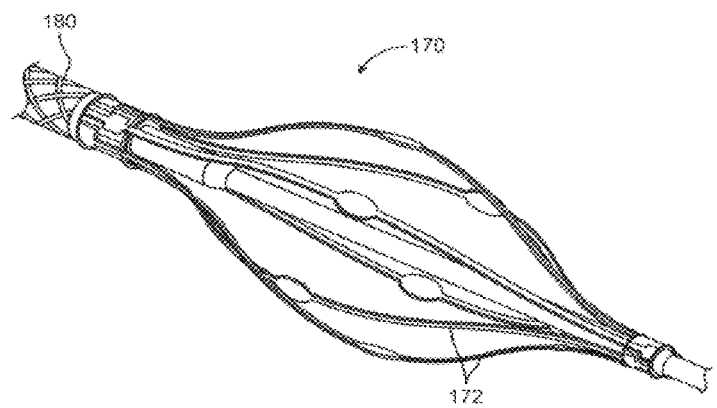

Each strut 172 may be used to conduct energy between electrode surface 174 and an electrical conductor extending proximally from the strut toward a controller. Proximal pads for connecting such conductors are illustrated in FIG. 12C, while distal structural pads 178 are illustrated in FIG. 12D. Adjacent electrodes 174 may be axially offset or staggered as can be seen in FIG. 12F. Insulating coating along each strut 172 may be inhibited or removed from an inner surface of proximal pads 176 so as to facilitate connecting of an associated conductive wire, such as by spot welding or other attaching means. Alternative polymer or non-polymer insulating materials may also be used, including parylene coatings, while alternative methods or attaching struts 172 to a catheter body may be employed, including adhesive bonding using insulating UV cure, embedding the pad structures in polyethylene or other polymers. Exemplary structures for fixing struts 172 of basket 170 to a catheter body 180 are illustrated in FIG. 12G.

Figure 12H:
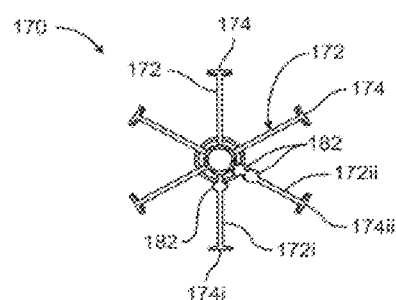

Referring now to FIGS. 12F and 12H, an alternative indicia providing a distinguishable image for rotationally registering selected electrodes 174 of basket 170 to images or other tissue material measurements can be understood. In this embodiment, an electrode 174i referenced as electrode 1 may have a radiopaque marker 182 disposed on the associated strut 172i. A strut 172ii supporting an associated second electrode 174ii may have two radiopaque markers 182 provide a circumferentially asymmetric count indicator allowing all electrodes to be referenced without ambiguity. The shape of electrodes 50 may vary, for example, electrodes 174 may be wider than other portions of struts 172 as illustrated in FIGS. 12A-G.

In some embodiments, remodeling may be performed using irrigation and/or aspiration flows. In many such embodiments, an irrigation port directs fluid, such as a saline solution, from an irrigation lumen to an interior of the basket. An aspiration port may provide fluid communication between an aspiration lumen and an interior of the basket. One or both of these fluid flows may be driven continuously, or may alternatively pulsate before, during, and/or after treatment. In some embodiments, aspiration and/or irrigation flow may occur acutely or concurrently so as to circulate between the irrigation port and the aspiration port. Optionally, the flow may carry debris to the aspiration port, where the debris may be evacuated through the aspiration lumen. There may be coordination between the irrigation system and the aspiration system such that the irrigation fluid may remain confined in an area closely adjacent the basket so as to inhibit embolization of debris when the basket is expanded within the blood vessel. Such coordination, for example, may inhibit distal movement of debris, and/or may obviate any need for a distal and/or proximal barrier or membrane. In some embodiments, the circulation of fluid between an irrigation port and an aspiration port may create an effectively bloodless environment adjacent the electrodes to facilitate treatment, imaging of tissue, or other aspects of therapy.

Figure 14F:
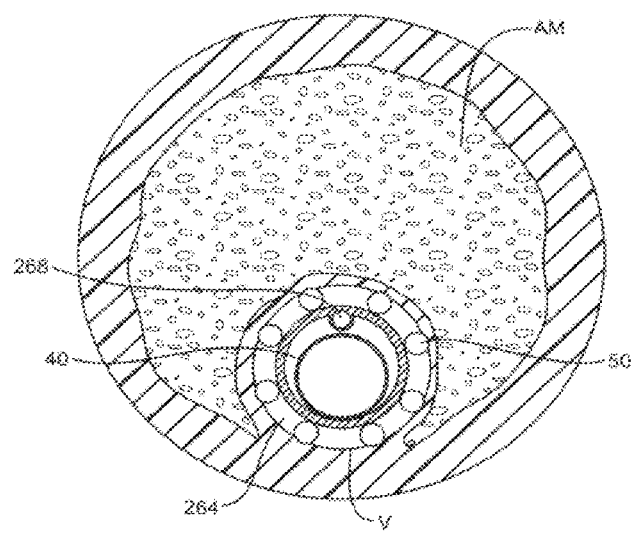
FIGS. 14F-H are cross sectional views taken across a body lumen and treatment device to show additional aspects of the eccentric treatment methods and devices.
Figure 14G:
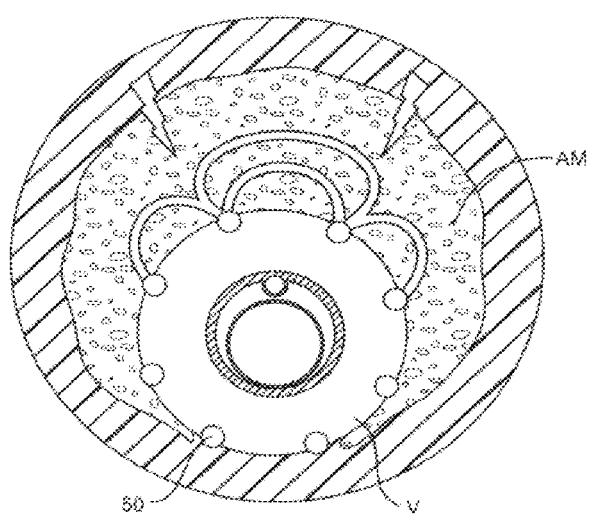
Figure 14H:
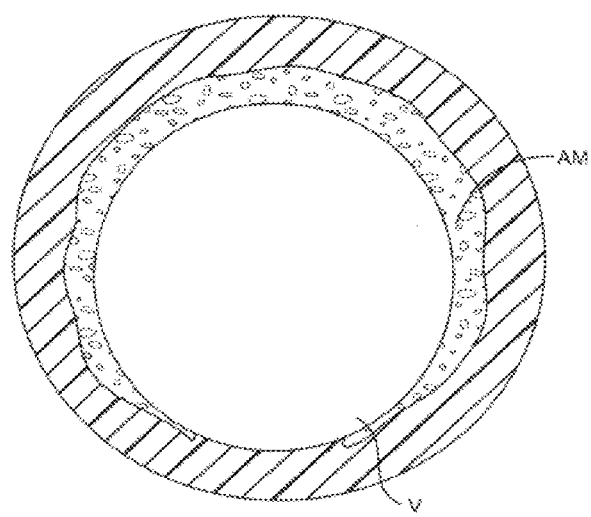

When the imaging catheter detects atherosclerotic material AM as illustrated in FIG. 14C, an appropriate subset (possibly including only a single electrode 50) is activated to remodel the atherosclerotic material AM, as illustrated in FIG. 14D, and the open vessel lumen size increases moderately during treatment. The catheter is pulled proximally to the next atheroma, which is again detected and treated. A cross section of the limited open lumen prior to treatment is schematically illustrated in FIG. 14F, which also illustrates a saline flush or irrigation lumen 268 of the catheter 264. Treatment energy and the moderate increase in the open lumen diameter of the vessel V are schematically illustrated in the cross section of FIG. 14G. After a healing response gradually increases the open lumen diameter, the longer term open lumen results schematically illustrated in FIG. 14H may then be provided.

Figure 15A:
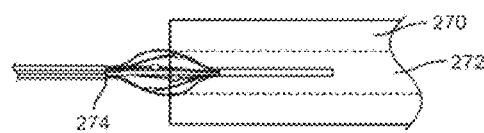
FIGS. 15A and 15B illustrate an eccentric treatment device and method in a gelatin artery model.
Figure 15B:
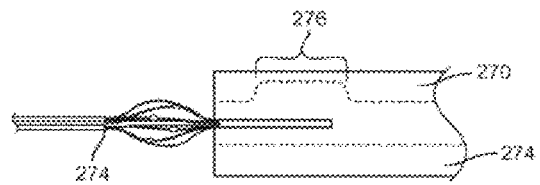

Referring now to FIGS. 15A and B, eccentric material removal in a gelatin artery model 270 are presented. Prior to the test, the artery model includes a consistent lumen 272 as seen in FIG. 15A. A test eccentric treatment catheter 274 having an expandable basket supporting a circumferential array of electrodes is introduced into lumen 272, with the expandable basket supporting the electrodes in engagement with the luminal wall. Selected electrodes of test catheter 274 were energized so as to eccentrically treat the gelatin artery model 274, thereby effecting eccentric remodeling of the gelatin model, in this case by removing an eccentric volume 276 from along one side of lumen 272. The orientation and amount of the material removed was controlled by selectively energizing electrodes of test catheter 274.

Still further alternatives are available. For example, another way to employ radiofrequency energy to tissue proximate to a lumen may be to energize a plurality of the adjacent electrodes with differing radiofrequency signals so as to employ the adjacent electrodes as a phase array. A phase array may direct or steer an electromagnetic signal in a desired direction using constructive and destructive interferences between signals of adjacent elements of the array. By controlling phases of the adjacent signals, a phase array of electrodes may provide a focused and/or steerable radiofrequency signal.

Along with controlling steering and directionality, adjusting phases of adjacent radiofrequency electrodes may allow focusing of some or most of the radiofrequency energy at a desired depth D inside the treatment zone while inhibiting radiofrequency energy delivery between the electrode surfaces and depth D using constructive and destructive interference between the signals. For example, such a system may be employed to preserve the cap of a plaque so as to reduce restenosis. Inhibiting heating of the cap while focusing energy toward an internal portion of the plaque may lower an immune response to heat that could otherwise lead to restenosis. Hence, inhibiting heating of the cap may reduce restenosis. Alternately, an effective dose of energy may be directed to tissues at a depth D that is targeted at a distance from the luminal wall.

Figure 17A:
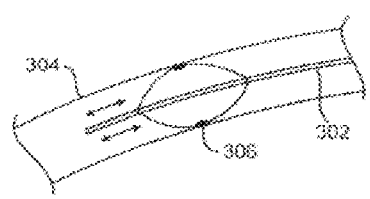
FIG. 17A illustrates physical targeting within vessel by longitudinal movement.
Figure 17B:
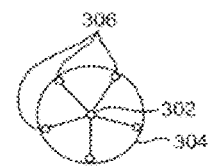
FIG. 17B illustrates physical targeting within vessel by radial electrode activation.
Figure 17C:
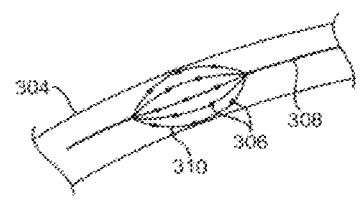
FIG. 17C illustrates physical targeting by activation of radial and longitudinal electrode combinations.

As can be understood with reference to FIG. 17A-17C, physical targeting of tissue can be accomplished by positioning of electrodes by moving longitudinally in vessel until positioned in the vicinity of targeted tissue. As schematically illustrated in FIG. 17A, axial movement of a distal end of probe in the form of a catheter 302 within a body lumen 304 allows different axial portions of the lumen wall to be targeted for analysis and treatment. An additional method to physically target eccentric disease in a radial manner is to apply bipolar energy selectively to specific electrodes 306 so as to direct energy through the targeted tissue, as can be understood with reference to FIG. 17B. In some embodiments, radial and longitudinal physical targeting may be effected by selective activation of electrodes distributed both radially and longitudinally on an expandable body 310, as illustrated in FIG. 17C.

Figure 18:
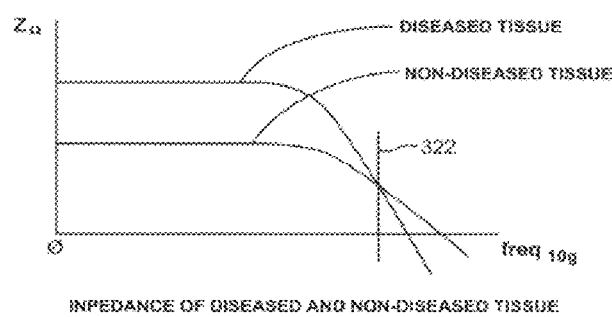
FIG. 18 illustrates electrical impedance versus frequency characteristic of diseased and non-diseased tissue.
Figure 19:
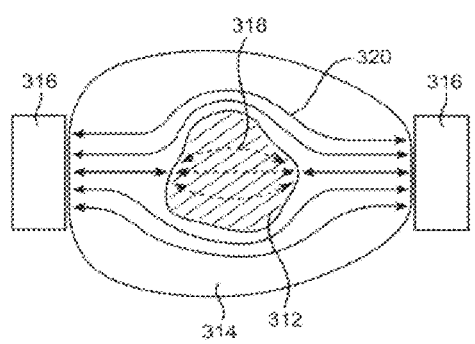
FIG. 19 illustrates shielding of high impedance tissue from electrical current by surrounding lower impedance tissue.

Frequency targeting of tissues is illustrated in FIGS. 18 and 19. As graphically illustrated in FIG. 18, different tissue types have different characteristic electrical impedances that cause the tissue to absorb energy of certain frequencies or frequency ranges more readily than others. By applying energy at the specific frequency or range of frequencies that the tissue is more conductive, energy penetrates the tissue more readily. In general, it has been shown that samples of diseased tissue exhibit higher impedance characteristics than samples of healthy tissue. As illustrated in FIG. 19, in the case where a diseased area of tissue 312 is surrounded by relatively healthy tissue 314, the healthy tissue is likely to shield the diseased tissue from electrical current flow due to the lower impedance of the healthy tissue. Hence, minimal (or less than the desired) current flow 318 may pass through diseased tissue 312, and heavier current flow 320 may be seen in low impedance healthy tissue 314 when bipolar current is transmitted between electrodes 316. Typically, the frequency ranges in which tissue impedance varies to a useful degree occur between 100 kilohertz and 10 Megahertz.

Frequency targeting seeks to deliver more energy to the diseased tissue by determining the frequency or range of frequencies at which the impedance of the diseased tissue is equal to or less than that of the healthy tissue, such as by operation at or above a threshold frequency 322 as illustrated in FIG. 18. Energy delivered at the specified frequency or range of frequencies may cause more heat to be dissipated in the diseased tissue than energy delivered outside of those specific frequencies.

Figure 20:
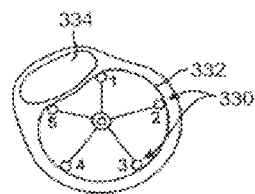
FIG. 20 illustrates electrical impedance measurement utilizing multiple radially spaced electrodes.

The use of impedance measurements to determine a location and/or state of tissue may be generally understood with reference to FIG. 20. First, impedance measurements utilizing an array of radially spaced electrodes 330 within lumen 332 may be used to analyze diseased tissue 334. Impedance measurements between the electrodes of the array, and particularly impedance measurements between pairs of adjacent electrodes (and/or between pairs of separated electrodes), may differ when the current path passes through diseased tissue 334, and when it passes through healthy tissues of the luminal wall. Hence, impedance measurements between the electrodes on either side of diseased tissue 334 may indicate a lesion, while measurements between other pairs of adjacent electrodes may indicate healthy tissue.

The state of a tissue can be affected/changed by temperature: for instance, lipids start denaturing at 85° C. and turn into a new state, fatty acids, which may be 90% more compact in volume than the original lipids. Alternately, impedance may be used to identify and target amongst tissue types with or without disease; for example, a target tissue may be identified and treated based on differing characteristics from adjacent tissues. If one knows the temperatures of state change for a tissue, and the impedance of the different states of the tissue, then by measuring the tissue impedance, it is possible to detect a state change, and/or to estimate what the temperature is, thereby allowing one to monitor the progress of the therapy. E.g.: if impedance of lipids were 100 Ohms, and impedance of fatty acids were 90 Ohms (here using hypothetical values), and knowing that lipids turn into fatty acids at around 85° C., then detecting a change in impedance from 100 Ohms to 90 Ohms indicates that the lipids turned into fatty acids and therefore that the temperature should be around 85° C. Analysis of tissues proximate to a lumen may use specific frequencies to verify a type and condition of tissue based on electrical impedance measurement. Normal use will include the discovery and characterization of diseased tissue using intraluminal ultrasound or other methods. Measurement of tissue electrical impedances over radially spaced electrodes may allow for verification of the existence of tissue states or types and provide knowledge of the location of the electrodes relative to specific tissue. As a further alternate, FIGS. 35D, 35E depict how the location and relative proximity of an implant structure 652 as it relates to an electrode 634A-634F may be sensed and used to aide in controlling the delivery 653. As is shown in FIG. 35E at the point of CONTACT or near CONTACT, energy 653 may cease to be delivered as electrodes 634F and 634A come into contact or near contact with implant structure 652 as system 10 (FIG. 33) is used to treat in-stent restenosis.

Figure 21:
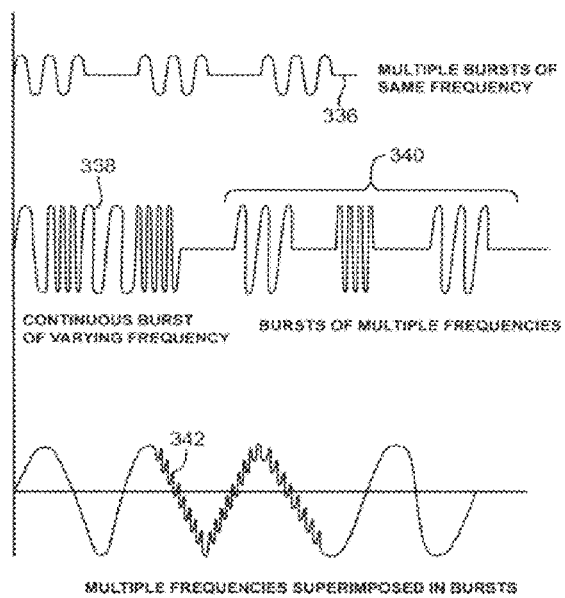
FIG. 21 illustrates variations of multiple frequency therapy.

Multiple frequency therapies and signals are schematically illustrated in FIG. 21. Therapy may consist of the application of electrical energy at a single frequency or at multiple frequencies. Depending on the composition of the target tissue and surrounding tissue, the optimum treatment may consist of a single frequency to target a single tissue type, multiple frequencies to target multiple tissue types, or multiple frequencies applied to a single tissue type. Multiple bursts of the same frequency 336, varying frequencies, such as a continuous burst of varying frequency 338, bursts of multiple frequencies 340, and multiple frequencies superimposed (optionally in bursts 342) may be employed.

Multiple frequencies can be applied in any sequence from any combination of electrodes in contact with the target tissue or surrounding tissue. Multiple frequencies can be applied as discrete frequencies or can be applied as a frequency sweep across a range in a linear, logarithmic, or other manner.

Figure 22:
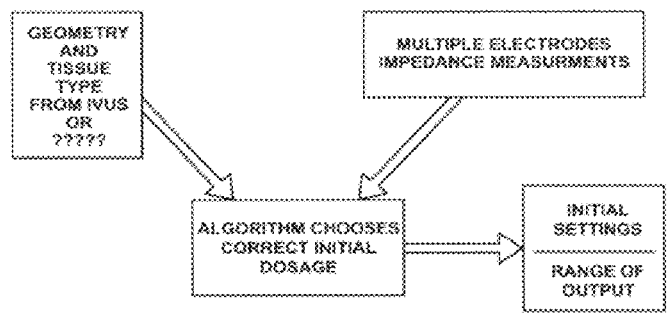
FIG. 22 illustrates use of physical tissue characteristics from external sources combined with electrical impedance measurements to determine a desired or optimum energy setting.

An energy control arrangement is schematically illustrated in FIG. 22. In general, impedance and physical tissue characteristics may be utilized to set the output or treatment parameters. Geometry and tissue type may be determined as described herein using IVUS or other similar detector techniques. Electrode impedance measurements from multiple electrodes may be taken. An algorithm of the system processor may choose a correct initial dosage, and initial settings and/or range output.

Regarding setting up the correct initial dosage, the location and type of target tissue to be treated may also be generally diagnosed and characterized by ultrasonic, optical, or other types of intraluminal sensing devices. Using the multi-electrode approach, electrical impedance measurements may be used to understand the electrical characteristics of target tissue of varying geometries and types previously diagnosed. Using that data, the initial therapy dosage setting can be optimized.

Regarding determination of proper dosage during therapy, the pattern of energy delivery can be a single pulse or multiple pulses of varying duration separated by resting periods of varying duration. The measurement of electrical impedance of the tissue, and of the electrode to tissue interface during energy delivery, and between energy pulses may be used to determine the optimum durations of energy delivery and resting periods. Pre-treatment bursts of radiofrequency energy can be applied to condition the target tissue. Conditioning may be utilized to activate HSP's in healthy tissue or non-target tissue prior to treatment to get better protection of such tissue. Post-treatment bursts of radiofrequency energy can be applied to control the cool down time of the tissue. Interim treatment bursts of radiofrequency energy can be applied to control the temperature of the target and surrounding tissue between multiple therapy bursts. Energy can be delivered in any combination of amplitude and frequency from any combination of electrodes. Some examples of energy bursts and pulse width modulations are shown in FIG. 21.

Impedance and/or impedance phase angle measurement on multiple electrodes may also be employed. When a multi-electrode design is used it is possible that some of the electrodes will be in contact with the lumen wall and others will be suspended in the blood or other existing fluid or thrombus, or existing stents, or foreign materials of the like. The measurement of impedance at various radial locations allows the determination of which electrodes are in contact with the lumen wall and which ones are in contact with fluid such as blood. Phase angle may be indicative of increased capacitance and decreased conductance as electrodes come into sufficient contact with tissue, as blood may have less capacitance and greater conductance than tissue where a greater impedance phase angle may be an indicator of an increase of capacitance relative to conductance. By way of example, this information may be displayed to the user, such as on a screen of a power generator or user interface, to communicate whether sufficient contact is present to enable tissue treatment. This contact determination may be further used in combination with an intraluminal viewing device such as ultrasound to determine the physical orientation of electrodes.

Utilizing the impedance measurements between multiple electrodes, the determination of the contact status of each electrode with tissue or blood may be utilized to determine if the electrode carrying mechanism (catheter) is in the proper location for therapy. Impedance measurements between multiple electrodes may be used to determine contact quality of electrodes to tissue. Poor contact quality can cause excessive or unwanted localized heating or can otherwise prevent optimum treatment. Determination of contact quality may be utilized to minimize this type of problem.

In some situations the choice of electrode may be determined by a combination of position and quality of contact. Impedance measurements between multiple electrodes may be utilized to better understand which electrodes are in better contact or a better position to treat a specific area or lesion. The determination of energy level and frequency to be applied to the target may be based on quality of contact. Impedance measurements between multiple electrodes may be utilized to determine the optimum energy level and frequency. Energy may be applied to a single pair of electrodes, between multiple pairs of electrodes, or from a single electrode to multiple electrodes, or any combination thereof. Impedance measurements between multiple electrodes may be utilized to determine the optimum pattern.

Figure 23:
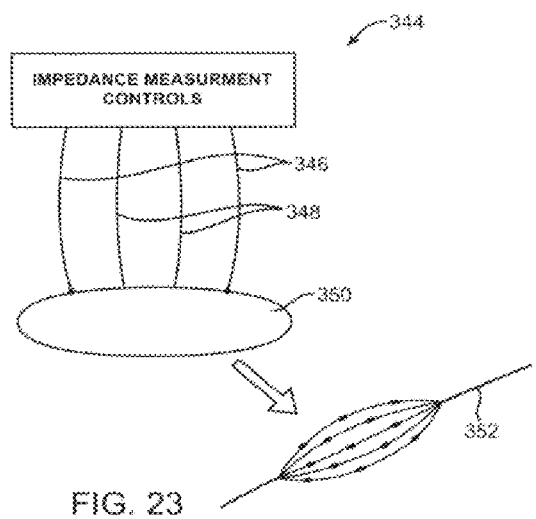
FIG. 23 illustrates four-electrode measurement system distributed across multiple electrodes to measure contact and tissue impedance.

Different embodiments may employ impedance measurement using two vs four electrodes, as can be understood with reference to FIG. 23. Four-electrode systems have been used for the measurement of electrical impedance in many applications. Four-electrode systems are inherently more accurate than two electrode systems due to inaccuracies created in the two-electrode systems by excessive contact impedance and electrical polarization reactions created in the contact area, however, electrode arrays of any suitable number may be used for a specific sensing and energy delivery application. In the four-electrode system 344, energy is delivered to the target by two energy delivery electrodes 346 and an impedance measurement is taken between the other two high impedance electrodes 348 shown schematically in contact with the tissue 350 in the energy path. In this multiple-electrode application any two electrodes can be utilized to deliver energy while any other two electrodes can be utilized for impedance measurement, thus forming a four-electrode measurement system. A probe or catheter 35 may include a circumferential and/or longitudinally distributed array of electrodes may be used to contact the tissue, and any four electrodes of the catheter can be configured for energy delivery or impedance measurement. Thus, the electrode array can be utilized as a two or four electrode system.

In many applications it is helpful to know how much energy is being delivered to the target tissue and how much is being dissipated in the interface between the electrodes and tissue. By taking measurements as a two-electrode system and then as a four-electrode system the electrode to tissue interface may be characterized and that data may be utilized to determine how much energy is being dissipated in the electrode to tissue interface and how much is actually delivered to the target tissue. Measurement of the electrical impedance in a plurality of electrode configurations, including the two or four electrode configurations, may be performed statically utilizing small excitation signals or can be measured dynamically during the application of energy at the normal therapy levels. Using this technique, tissue electrical impedance may be measured dynamically during the application of energy to determine the state of the treated tissue and surrounding tissue. For controlling the energy delivery dosage, the electrical impedance characteristics of tissues vary due to temperature variations and the molecular state of a tissue. Dynamic measurement of electrical impedance of the tissue during application of energy can be used to monitor the changes in the tissue and the progress of the therapy. A four-electrode implementation of the electrode system would allow for measurement of the electrical impedance of the electrode to tissue interface and therefore, measurement of the change in temperature of the tissue at the contact surface and that of the contact tissue.

Impedance measurement may optionally be performed in monopolar configuration. It is possible to utilize multiple electrode systems in a monopolar configuration where the return electrode is an electrically conductive pad applied to the external surface of the patient or the like. In this configuration impedance measurements can be performed between any one of the internally applied electrodes and the external return pad in the two-electrode mode or any one of the internally applied electrodes can apply energy that flows to the external return pad while any other two internally applied electrodes is used to measure impedance.

Regarding temperature measurements, impedance measurements taken prior to therapy may optionally be utilized to calculate a normalized value to be used in further calculations to determine the change in temperature from that initial value. Dynamic monitoring of the electrical impedance of target and surrounding tissue during therapy may be utilized to calculate the change in temperature of tissue. In some embodiments, dynamic monitoring or the electrical impedance of the interface between electrodes and tissue may be utilized, for example, to prevent tissue charring or coagulation of blood at the interface.

Temperature change during therapy may be utilized to determine the effectiveness of energy delivery settings and to determine the condition of the tissue being treated. In addition to direct temperature measurement by using sensors, measurement may be performed by intraluminal ultrasound or other mechanism and verified by data derived from impedance measurements.

Figure 24:
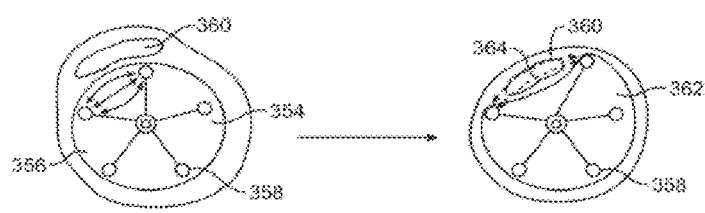
FIG. 24 illustrates flooding of vessel with non-ionic fluid to direct energy to vessel wall and surrounding tissue, reducing losses in native fluid.

Use of the systems described herein with ionic and non-ionic fluid can be understood with reference to FIG. 24. When electrical current flows in an ionic fluid such as blood filling a lumen 356, at least a portion of the current may pass through the blood when electrodes 358 are energized. Even with electrodes on either side of a target tissue 360, heating of the target tissue may be reduced by the current flow within the blood. When used in a fluid-filled lumen such as an artery, the catheter device can be used in combination with a non-ionic fluid flooding the area 362 to displace or partially displace the native fluid to modify the conductivity of the environment around the electrodes. This action can be desirable in order to direct the energy, in the form of electrical current 364, into lumen walls instead of through the native fluid, thereby delivering energy to the tissue of the surrounding walls with minimal dissipation into the fluid filling the lumen. A second purpose of the non-ionic fluid or an ionic fluid may be to provide cooling to the electrodes and to the tissue on the surface and just below the surface of the lumen wall.

Electrical impedance measurements at the electrodes may be utilized to determine the conductivity of the surrounding fluid, thus measuring the concentration of non-ionic fluid in the native fluid. This data may be fed to the control system to allow for adjustment of ionic fluid concentration to optimize delivery of energy to the target tissue and minimize undesired effects to surrounding tissue. Use of blood as contact interface is also an option. Blood is a conductive ionic fluid that may be used as an interface between electrodes and tissue to ensure a good electrode-tissue contact and low contact impedance.

Figure 27:
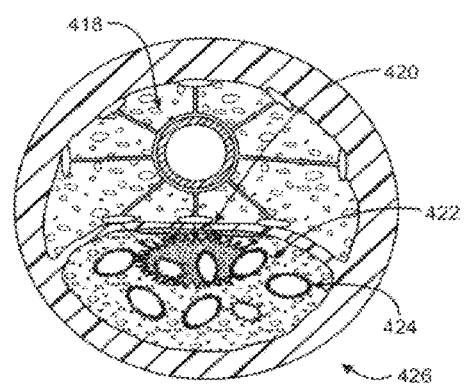
FIG. 27 illustrates selective treatment of plaque.
Figures 27A, 27B, 27C:
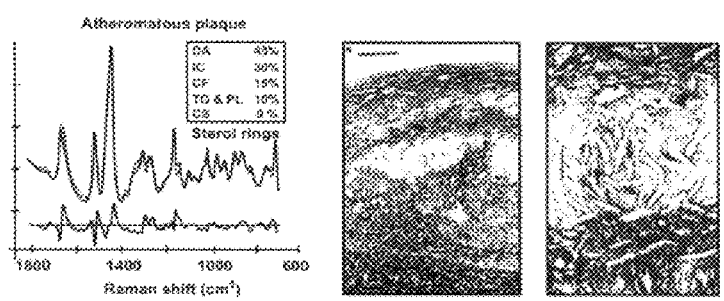
FIGS. 27A-C illustrate spectral correlations of tissues, as may be used to analyze or characterize plaques.

Referring now to FIG. 27, the catheter devices 418, systems and methods described herein will often be used to treat plaques having fibrous tissue 420. Fibrous tissue 420 may be heated to a target tissue to a temperature in a range from about 90 to about 95 C, which may provide shrinkage of up to about 50%. Lipids 424 may be heated to target temperatures in a range from about 80-85 C, providing up to about 90% shrinkage. Damage to adventitial layer 426 may be inhibited or the layer protected by limiting heating to below about 62° C. These and other temperatures and shrinkage estimates are further determined by empirical testing or the like, from unpublished and/or published work, or form other sources such as numerical methods. Referring to FIGS. 27A-27C, spectral correlations to diseased tissue may allow tissue characterization using techniques such as those described in an article by Tjeerd J. Romer et al. entitled "Histopathology of Human Coronary Atherosclerosis by Quantifying Its Chemical Composition with Raman Spectroscopy," Circulation 97:878-885 (1998), the entire contents of which are incorporated herein by reference.

Figure 28A:
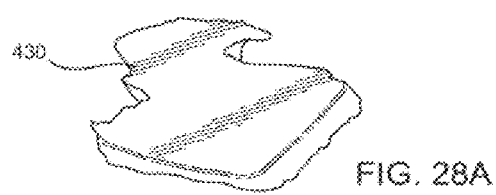
FIGS. 28A-D illustrate bench top remodeling of tissue using an animal fat model treated with an exemplary embodiment of the catheter system.
Figure 28B:
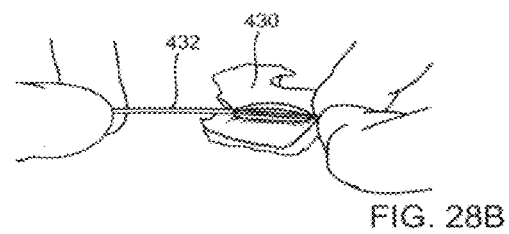
Figure 28C:
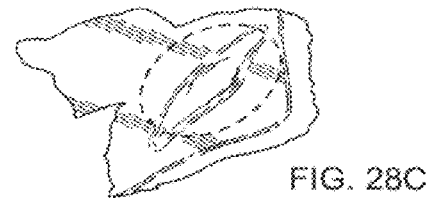
Figure 28D:
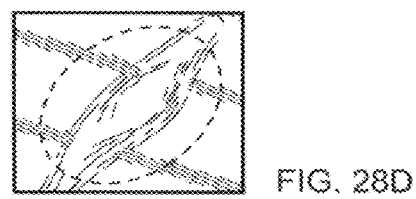
Figure 29A:
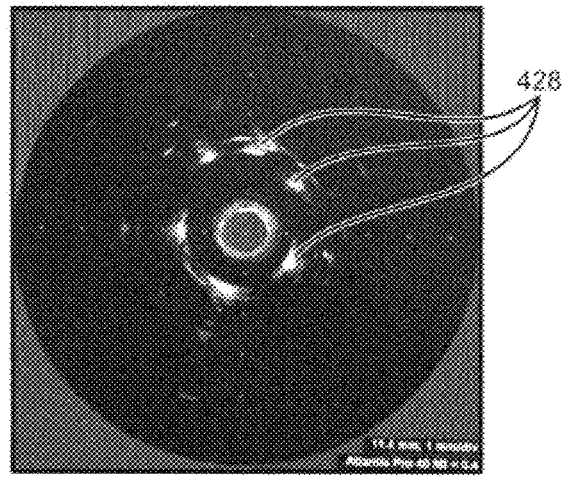
FIGS. 29A and 29B illustrate intravascular imaging and eccentric remodeling with an exemplary embodiment of the catheter system.
Figure 29B:
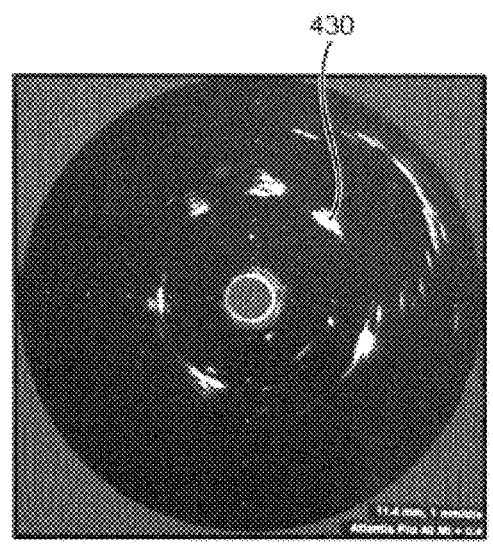

Referring now to FIGS. 28A-28D, feasibility of tissue shrinkage may be seen in a bench top experiment using a catheter system such as those described herein. An animal fat tissue model 430 (shown before the treatment in FIG. 28A) can be treated by manually holding the expandable structure and associated electrodes of the catheter in contact with a surface of the tissue during treatment with tissue remodeling electrosurgical energy (see FIG. 28B). After treatment, as seen in FIG. 28C and the close up of FIG. 28D, visible shrinkage of the tissue can be verified. Feasibility of the use of intravascular imaging with the methods and systems described herein can be verified by images of the six individual electrode-supporting struts 428 of the expandable structure of the catheter in FIG. 29A, as well as by viewing an eccentric void 430 that is created using a benign guided reshaping energy delivery targeted so as to increase effective artery diameter for better blood flow, as seen in FIG. 29B.

Figure 30:
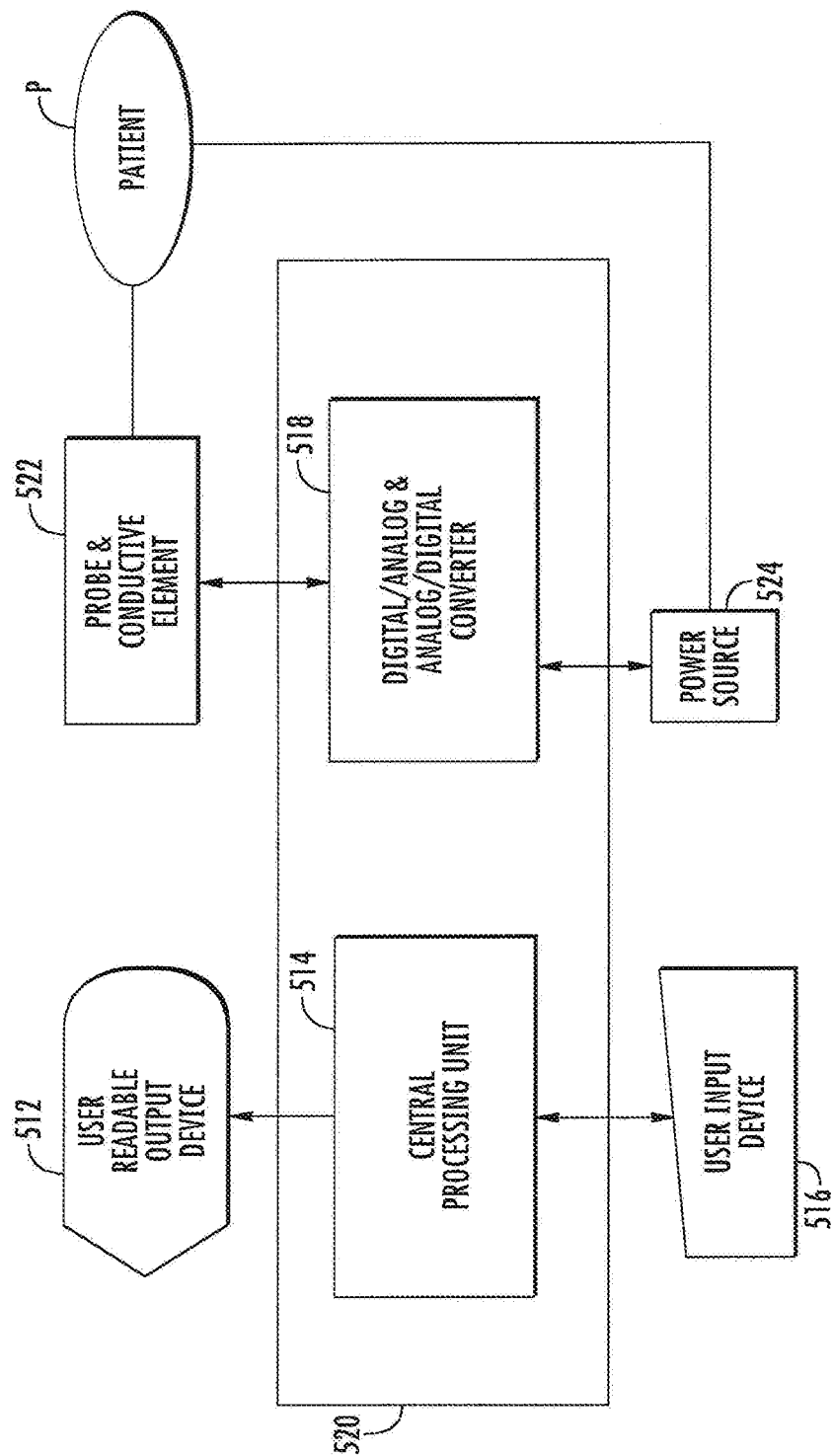
FIG. 30 is a simplified schematic illustrating components of the system of FIG. 2 that can be used for intraluminal tissue and other material analysis and characterization.

Referring now to FIGS. 30 and 31A, advantageous embodiments may employ aspects of electrical tissue discrimination techniques and devices described in U.S. Pat. No. 6,760,616 to Hoey et al., entitled "Tissue Discrimination and Applications in Medical Procedures," the full disclosure of which is incorporated herein by reference. As more fully described in that reference, tissue identification system 510 includes a user readable output device 512, a user input device 516, a processor 520, and a probe 522. The processor 520 includes a central processing unit ("CPU") 514, a Digital to Analog converter ("D/A"), and an Analog to Digital converter ("A/D") 518. Processor 520 may be included in processor 49 (see FIGS. 2 and 3), and probe 522 may comprise any of the catheter structures described herein, so that tissue identification system 510 may be, embodied in system 10.

Tissue identification system 510 may apply a sliding or variable frequency electrical signal by energizing the electrode with a variable frequency power source 524. Power source 524, the electrode of probe 522, and the engaged tissue of patient P can thus generally be included in a circuit, and an electrical characteristic of the circuit can be measured at different frequencies. In exemplary embodiments, an impedance (both phase angle and magnitude) of the circuit is measured at a plurality of frequencies within a frequency range of about 4 KHz to about 2 MHz. Each frequency/magnitude/phase angle datapoint may represent a tissue signature measurement, with a series of individual datapoints often being taken under similar conditions (for example, at a given frequency and without moving the electrodes) and averaged for enhanced accuracy. The tissue signature datapoints may be measure at a plurality of frequencies throughout a range of frequencies so as to generate frequency/phase angle/phase magnitude curves representing a tissue signature profile or correlation 530, 532, or 534, which may be used to characterize the tissue of the circuit.

The signals used to derive the tissue signature profiles 530, 532, 543 will often be driven between electrodes of the catheters described herein. Conveniently, the tissue included in the circuit may be controlled by selecting different electrode pairs for testing, with or without repositioning of the electrodes. There may be significant patient-to-patient differences (or even region to region differences within a patient) for individual tissue signature measurements, and these differences may, at least in part, be caused by the different configurations of the electrodes during testing, different distances between electrodes, and the like. Nonetheless, the relationships (and particularly the relative slopes of the profile correlations, the offsets between correlations, and the like will be sufficiently consistent to allow tissue characterization, particularly where a baseline tissue signature profile for the patient or tissue region is obtained using IVUS, OCT, or the like. Where a region of (for example) healthy tissue can be identified using IVUS and used to generate a baseline tissue signature profile for the patient, other nearby tissue signature measurements or profiles can then be normalized to that baseline, compared to the baseline, etc. From the offsets, the differences in slope, and the like, the tissue can be analyzed.

Referring now to FIGS. 31A-31J, the relationships between tissue signature profile curves or correlations can be used to analyze and characterize the tissues engaged by the electrodes of the probe. For example, a correlation 530 associated with fibrous plaque (seen on the left side of the graph of FIG. 31A) has both a slope and a magnitude that differs significantly from that of a calcified plaque 534 (seen in the right side of the plotted data) and from a correlation 532 associated with thrombus (generally between 530 and 534). The offsets between the correlations here encompasses a difference in phase for a given impedance, a difference in impedance for a given phase, or the like. As can be understood with reference to the graphical plots, the relationships between correlations may be determined by fitting curves to the data, by statistical analysis, by lookup tables, or the like. In exemplary embodiments, tissue signature measurements may be taken by (for example) a commercially available vector impedance meter such as a Hewlett-Packard Model No. 4193A, and the correlations may be captured using LabView™ Software and plotted or manipulated using Excel™ spreadsheet software from Microsoft, or the like. Once sufficient benchmarked data has been obtained and repeatability under different probe configurations has been established, electrical circuit measurements tissue characterization without benchmarking of each patient may avoid the expense of IVUS measurements.

Figure 31B:
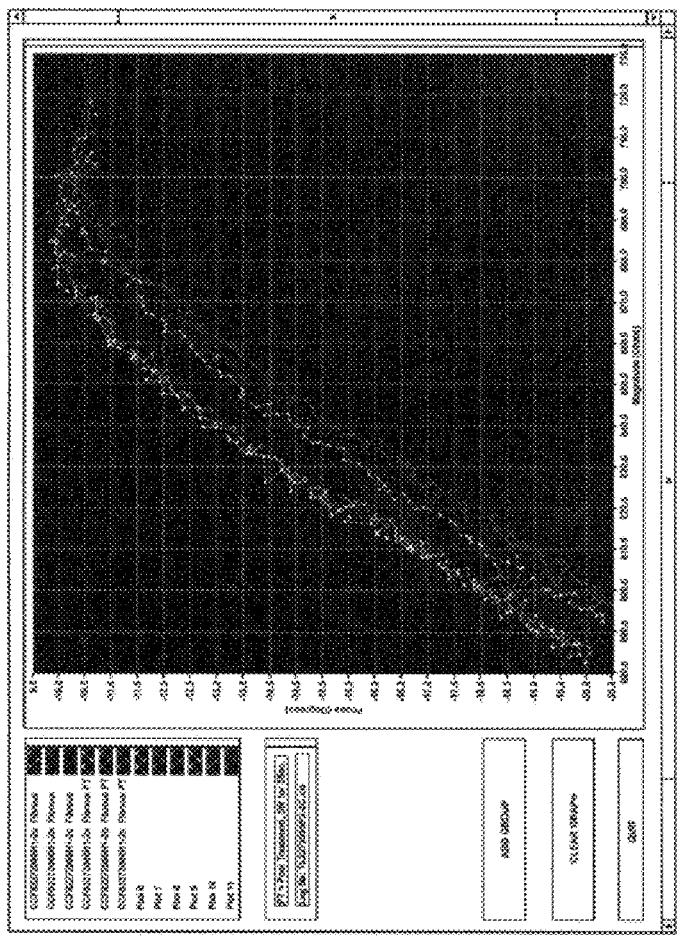

As shown in FIG. 31B, along with characterizing different tissues, the relationships can also be used as feedback on treatments of tissues proximate to luminal walls. For example, a fibrous plaque correlation or profile before treatment (toward the right side of the plot) changes in magnitude during treatment to a post-treatment correlation or profile (toward the left side). The treatment here comprised 2 W of electrosurgical energy for 2 seconds, showing that moderate remodeling or partial treatments can be monitored, verified, and/or controlled using the electrical characteristics of the circuit of tissue identification system 510.

Figure 31C:
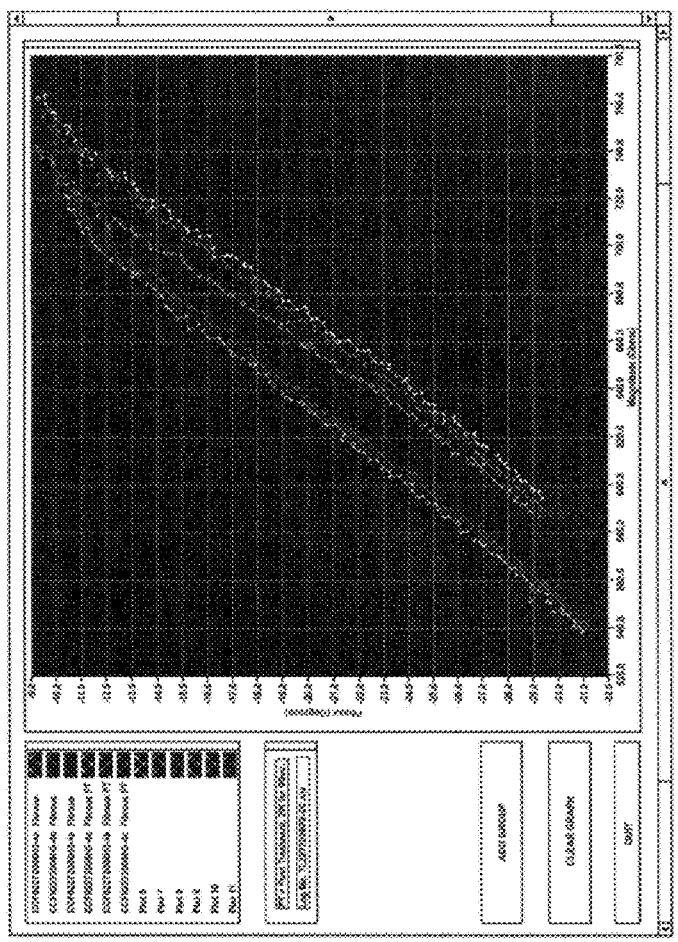
Figure 31D:
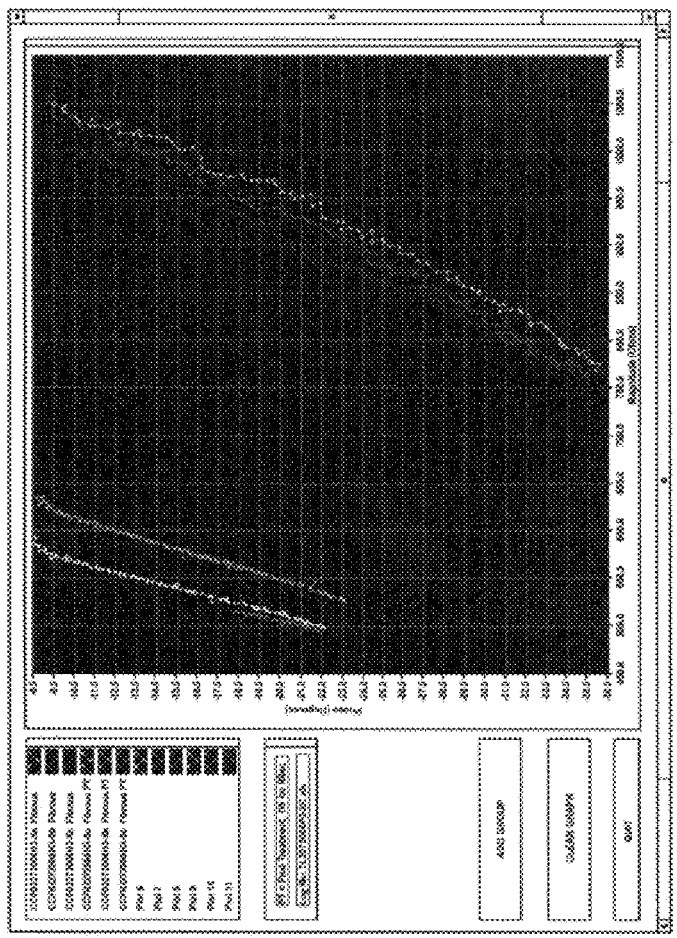

Advantageously, once an appropriate frequency or range of frequencies has been determined, the entire tissue signature profile need not be generated for analysis of ongoing tissue treatments and/or characterization of tissues, as offsets may be readily identified. Such measurements may, for example, allow tissue temperatures to be determined, particularly where the temperature is a treatment temperature that alters an offset of the tissue signatures. The energy of the electrical signals used for tissue analysis may typically be less than the remodeling treatments. A similar plot is shown in FIGS. 31C and 31D, with the post treatment correlation here being after treatment with 2 W for 9 seconds and 1 W for 9 seconds, respectively.

Figure 31E:
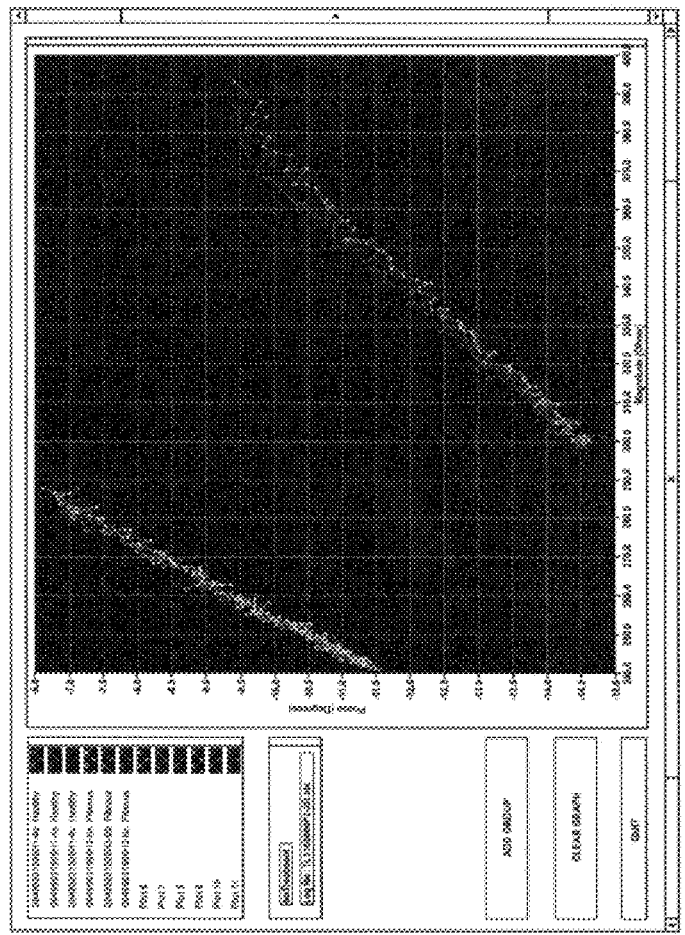
Figure 31F:
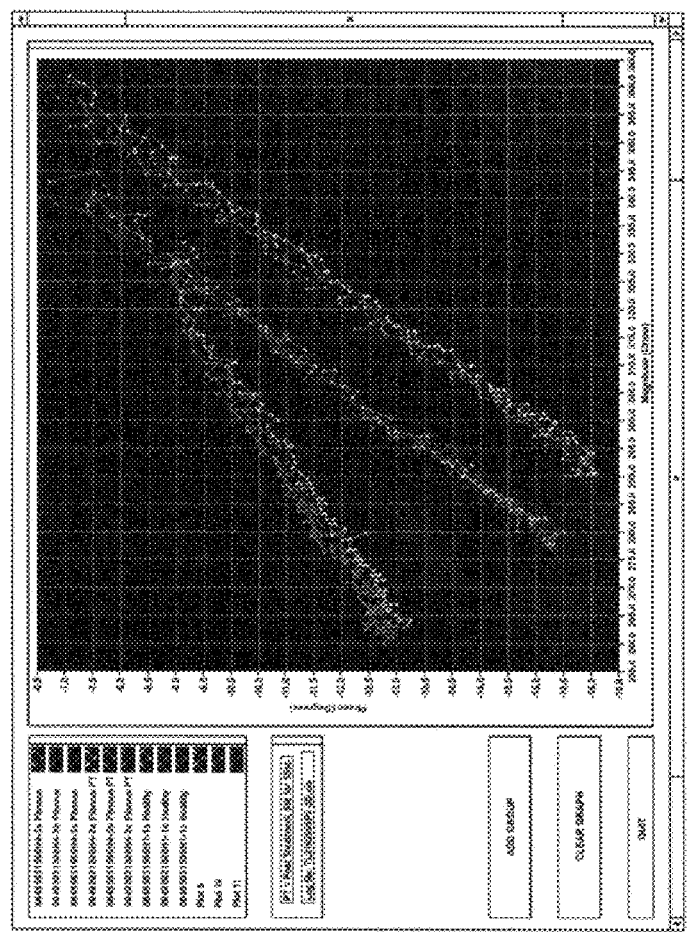
Figure 31G:
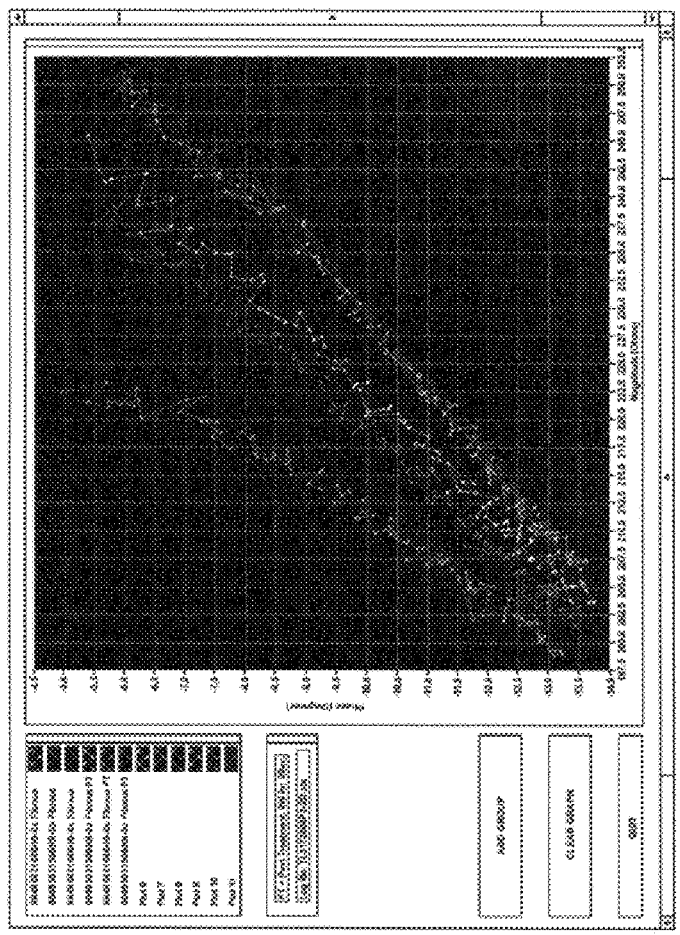
Figure 31H:
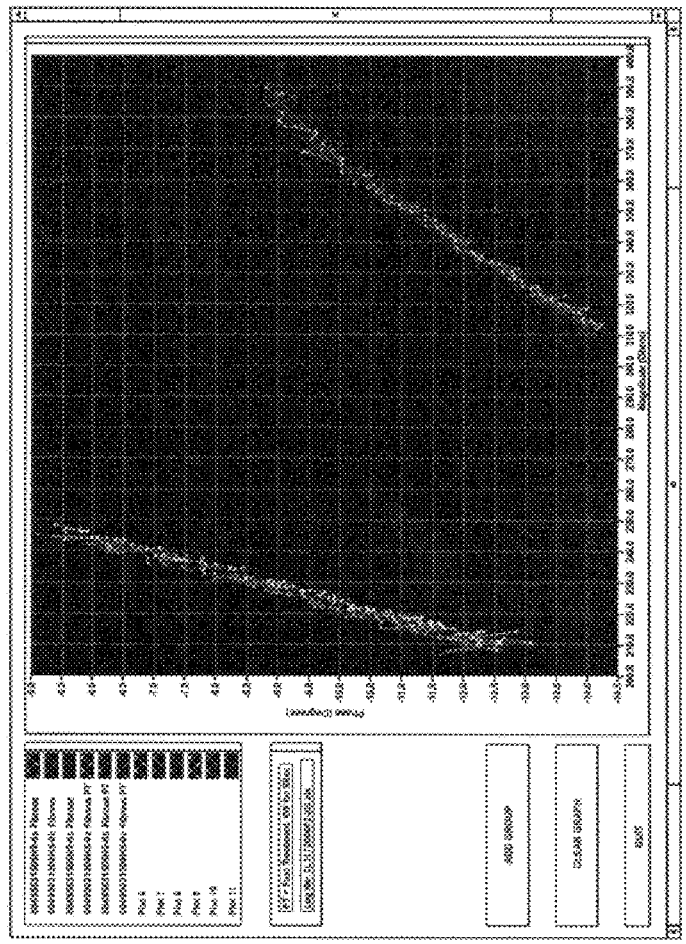
Figure 31I:
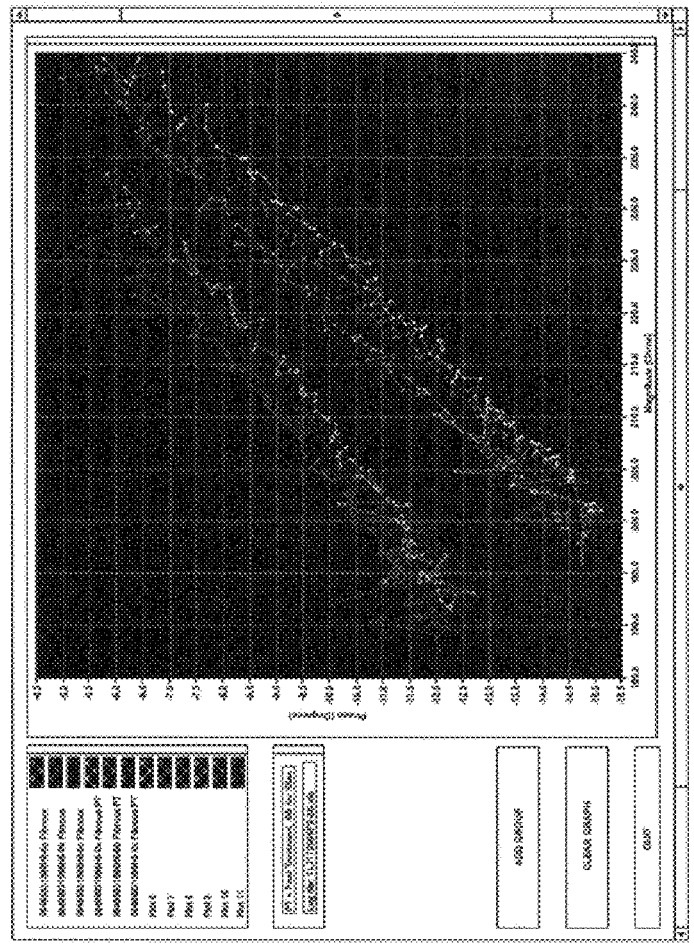
Figure 31J:
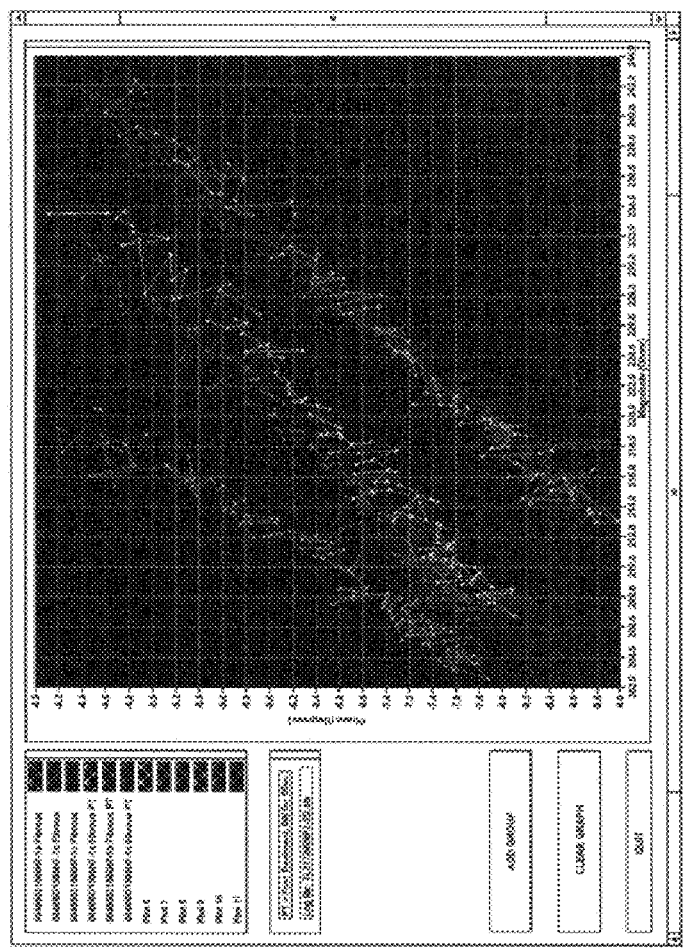

Referring now to FIG. 31E, relationships between healthy tissue (toward the right) and fibrous plaques (toward the left) can be identified from their associated tissue signature profiles or correlations, which differ significantly in both slope and magnitude. FIG. 31F shows relationships between correlations or profiles for fibrous tissue before treatment (left), fibrous tissue after treatment (right), and healthy tissue (center). FIGS. 31G-31J illustrate additional plots of relationships between profiles or correlations associated with fibrous tissues and treated fibrous tissues.

Figure 32:
FIG. 32 illustrates a variety of tissues for characterization and selective treatment by the system of FIG. 2.

Referring to FIG. 32 a severely diseased blood vessel with three basic categories of plaque can be seen: lipid rich (fatty) plaque, fibrous plaque, and calcified plaque or tissue. All may be present in one sample, and may also be present in the diseased tissue of (or adjacent to) one lesion, making the lesion hard to treat using conventional techniques. Through the tissue analysis techniques described herein, the correct prescription and dosage of energy may be targeted and delivered to effect a safe and appropriate (and often different) remodeling of the different tissue categories or types, at the appropriate locations of the constituent parts that make up each lesion.

Figure 32A:
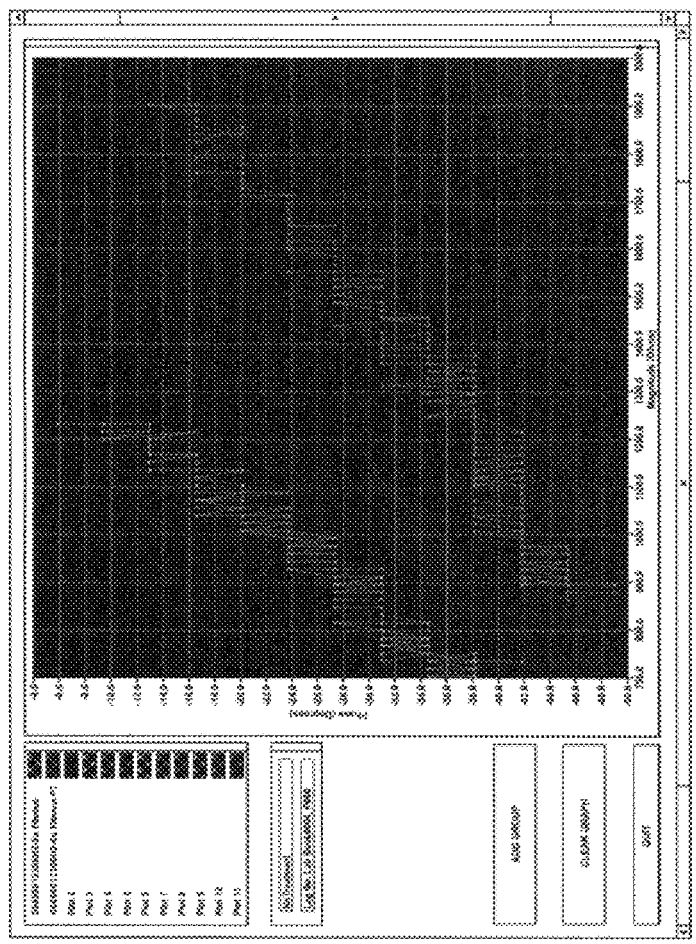
FIGS. 32A-C illustrate changes in a relationship between phase angle and impedance in a frequency range associated with treatment of a tissue, along with histological images of the tissue before and after treatment.
Figure 32B:
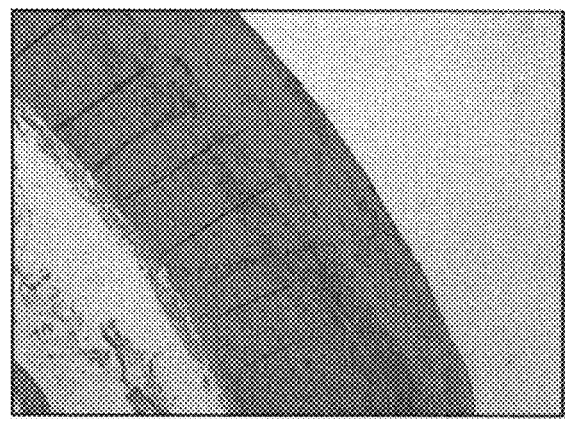
Figure 32C:

Referring now to FIG. 32A, this graph shows tissue signature measurements and tissue signature profile results obtained from a human aorta specimen, with these results for an engaged fibrous plaque before and after treatment. FIGS. 32B and 32C show histopathology slides of the tissue. The cracks visible on each slide may be artifacts of the mounting process. The nucleation or voids that show up in FIG. 32C, however, may indicate a remodeling of the tissue itself.

Experimental

Testing of the delivery of energy to tissue proximate to a lumen has included the treatment of in-stent restenosis, trials have yielded preclinical and in-human data.

1. Preclinical

An experiment was conducted to establish a comparison of temperature measurement during different energy doses at four depth levels, upon low pressure (less than 6 atmospheres) balloon inflation: 1) 0 mm, at the surface of the balloon, representing the endothelial layer of the vessel wall; 2) 1 mm, representing the border between the neointima and the media, at the stent location; 3) 2 mm, representing 0.5 mm into the adventitia; and 4) 3 mm, representing 1.5 mm into the adventitia. Comparisons of temperature were made between two population groups; one group in tissue with an implanted stent, and the second group without an implanted stent. The objective of the study is to determine the energy dosing that would provide a temperature of about 55° C. or greater while having minimal temperature elevation beyond the stent (1 mm and deeper).

Measuring temperature at the surface of three pairs of electrodes (7-8, 8-9, and 9-10), and 1, 2 and 3 mm deep, bipolar radiofrequency energy delivery was conducted in two rounds: for the first round only half of the electrodes are activated (electrodes 1-2, 3-4, 5-6, 7-8, 9-10 each pair energized in sequence), and for the second round, the other half of electrodes are activated (electrodes 2-3, 4-5, 6-7, 8-9, 10-1, again, pair energized in sequence). The test medium is heated to a baseline temperature of 37° C., representing nominal human body temperature. Temperature was captured from each of six thermocouples, starting 1-2 seconds before the electrodes were activated, and lasting for about 10 seconds following the activation of the last electrode (10-1). In all treatments, all the electrodes were activated, meaning that both first and second rounds were activated, leading to a "full circumferential" (FC) treatment.

Referring to FIGS. 43A-48, the individual lines demonstrate temperature measurement at the surface of three pairs of electrodes 705 (7-8; blue line), 706 (8-9; red line), 707 (9-10; green line), and measurement at three depths 708 (1 mm deep; purple line), 709 (2 mm deep; light blue line), and 710 (3 mm deep; orange line). As may be seen in FIGS. 43A-44B, the temperature measurements for energy doses, with stent vs. without a stent, are comparable. The peak temperature for each round is slightly higher with stent, vs. without a stent. In addition, the temperature measured in 1 mm deep, is slightly higher with a stent vs. without a stent. Proposed energy doses for in-stent tissue are shown in FIGS. 45A-48; among the energy doses tested, the dose of 4 watts for 2 seconds for the first round, followed by 4 watts for 1 second for the second round ("4×2×1") shown by FIG. 48, demonstrated the highest preferred peak surface temperature (~60° C.) while maintaining a preferred temperature at 1 mm depth. A peak temperature of about 55° to about 65° C. may enable collagen denaturation of the neointima tissue, dehydration and volume reduction, and, cell death is expected to be limited to the neointima tissue. Prevention of heat penetration into the adventitia may better avoid injury, inflammation, fibrosis and restenosis, while neointima volume reduction during balloon inflation, may prevent flow-limiting dissections inside the stent, which, can lead to better acute and long term results.

Figure 52A:
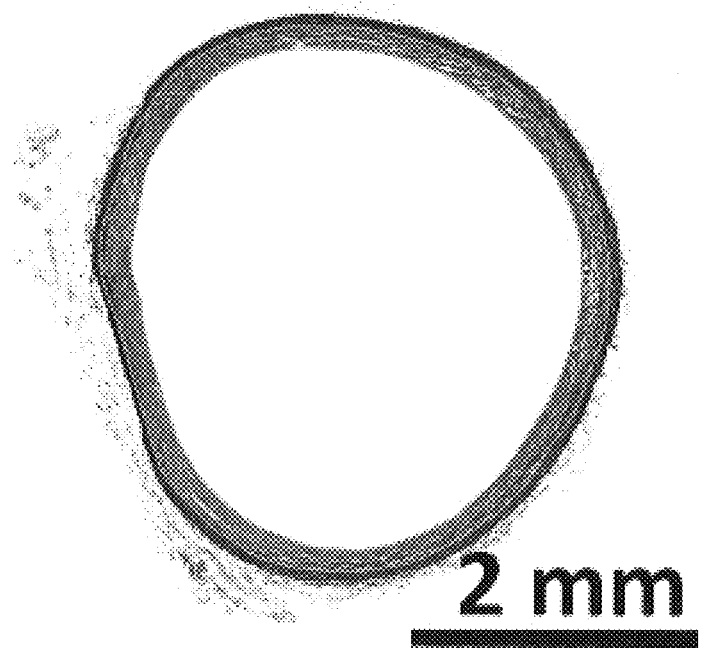
FIG. 52A illustrates 27-day histology results in a porcine left femoral artery for 4 W×2 s×1 s energy treatment.
Figure 52B:
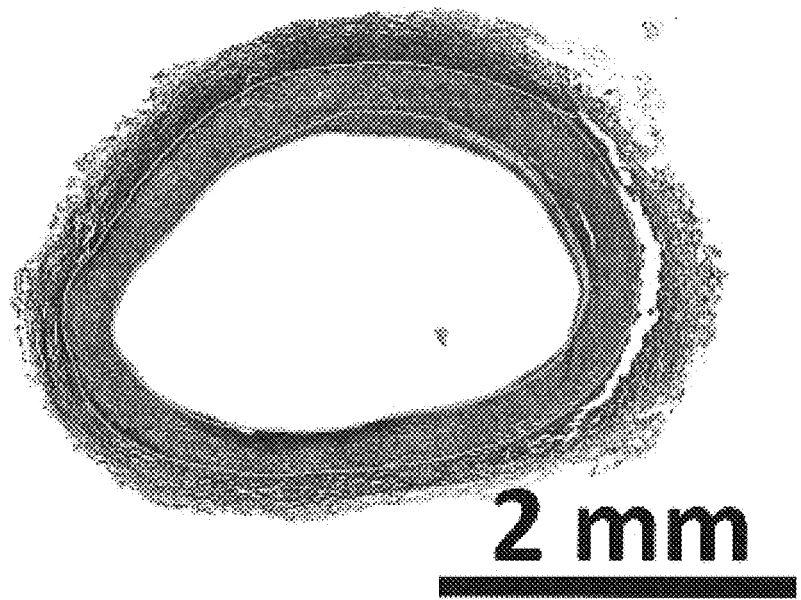
FIG. 52B illustrates 27-day histology results in a porcine left iliac artery for 4 W×2 s×1 s energy treatment.

Porcine animal subjects were treated with the 4×2×1 energy treatment and sacrificed at 27 days. A representative histology sample of the left femoral artery and of the left iliac artery are shown in FIG. 52A and FIG. 52B, respectively. It is observed that luminal patency is maintained after energy treatment in subject vessels, the vessels showing re-endothelialization and no thrombus formation. The greatest observed post-treatment luminal stenosis in response to 4×2×1 energy treatment was approximately 10.6% supporting the conclusion that such treatment may be a preferred means for heating a tissue treatment zone while avoiding subsequent stenosis response in either target or collateral tissues.

2. In-Human

Applying the understanding of preferred energy delivery from preclinical testing, the 4 W×2 s×1 s energy dose (electrodes fired sequentially, full circumference) was applied to a first in human trial under the appropriate procedures and protocols. A pool of patients were selected, each having a significantly restenosed 6 mm×150 mm stent implanted in the superficial femoral artery. Pre-operative assessment of each patient was conducted to verify the degree of in-stent restenosis and any pertinent additional lesion information (for example, the presence of calcification). Each patient received a number of energy treatments based on the length of the stenotic lesion relative to the working length of the balloon-mounted electrodes, wherein a 6 mm diameter balloon was used in for each patient. As is shown in Table 3, percent stenosis is reported as the percentage of the native artery diameter that is reduced by tissue in-growth. A pre-treatment stenosis of 95% would therefore correspond to only 5% of the natural lumen diameter remaining open; the lesser the reported percentage of stenosis, the more favorable the result in terms of restoring normal blood flow through the artery, however, both the percentage reduction in stenosis and the remaining percentage of stenosis may be considered as factors for determining an overall result. The data in Table 3 show a substantial reduction of in-stent restenosis lasting beyond an acute result. As is shown in FIGS. 49A-51C, pre-operative angiograms for each patient as compared to post-operative and 90-day post-operative angiograms demonstrate a substantial restoration of blood flow and an observable removal of the previously present in-stent restenosis. As one of skill in the art will appreciate, diffuse arterial disease in the leg is known to be tenacious, and often present along a significant portion of the diseased artery.

TABLE 3

| Patient Number | Pre-Treatment % Stenosis | Post-Treatment % Stenosis | 90-Day % Stenosis |
| --- | --- | --- | --- |
| 001 | 90-95% | 23-26% | 32% |
| 002 | 66% | 21% | 12% |
| 005 | 55% | 24% | 19% |

Figure 49A:
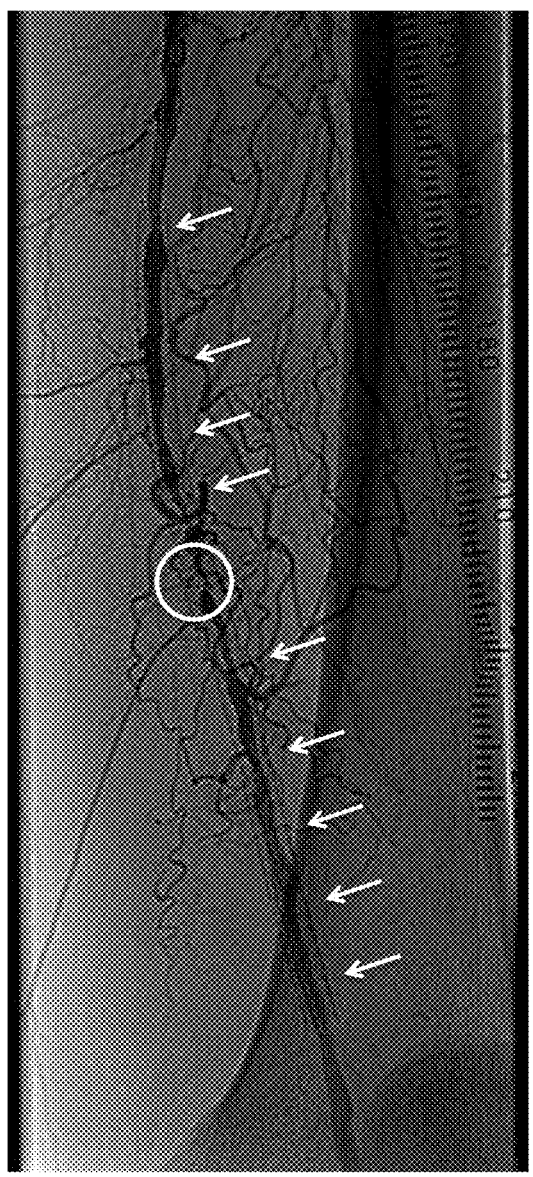
FIGS. 49A-49C show patient number 001's in-stent restenosis pre-operatively, acutely post-operative, and at 90 days post-operative, respectively.
Figure 49B:
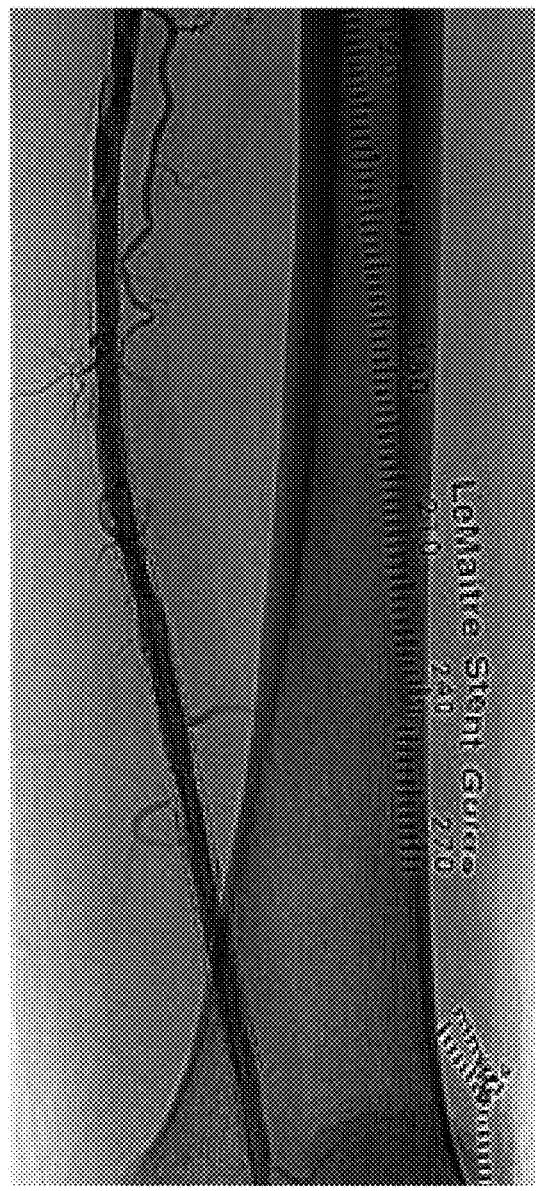
Figure 49C:
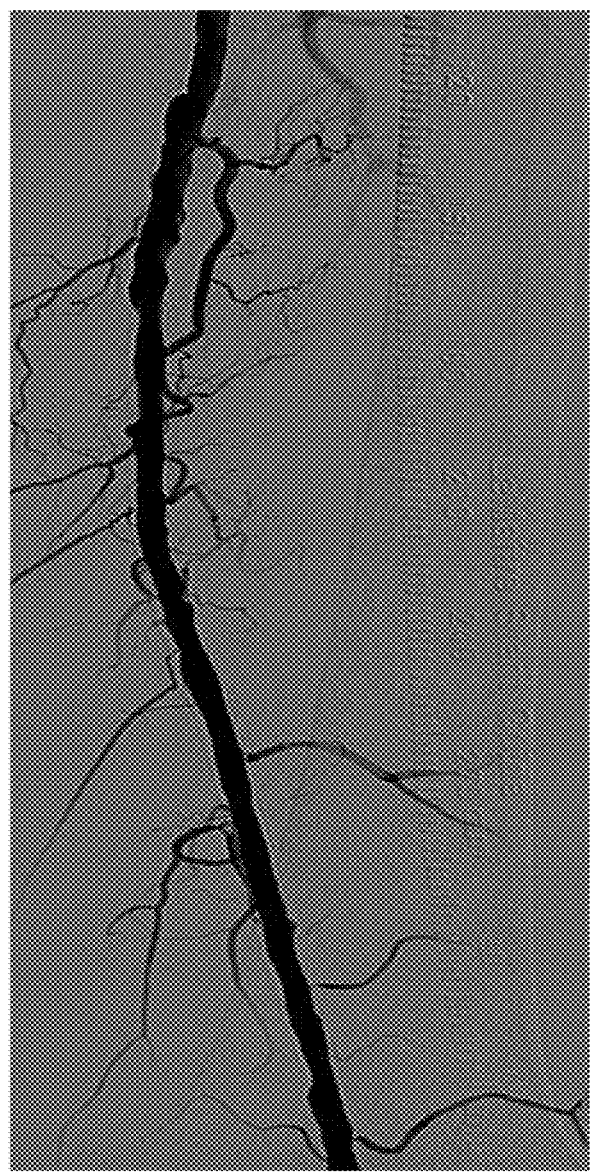

Biomechanics of arteries of the leg are known to include pulsatile, bending, torsion, and elongation/foreshortening motions that further complicate treatment options both for initial stenosis treatment and more so for restenosis treatment. Referring now to FIG. 49A, patient number 001's pre-operative condition shows substantial and readily observable narrowing of the artery by in-stent restenosis (shown by arrow markers) along the entire length of the 150 mm stent, with the most highly stenosed location being 90% to 95% reduced from the native artery diameter (shown inside of circled portion). FIGS. 49B and 49C respectively show patient number 001's acute post-operative and 90-day post-operative lumen diameter to be visibly improved throughout the length of the 150 mm stent.

Figure 50A:
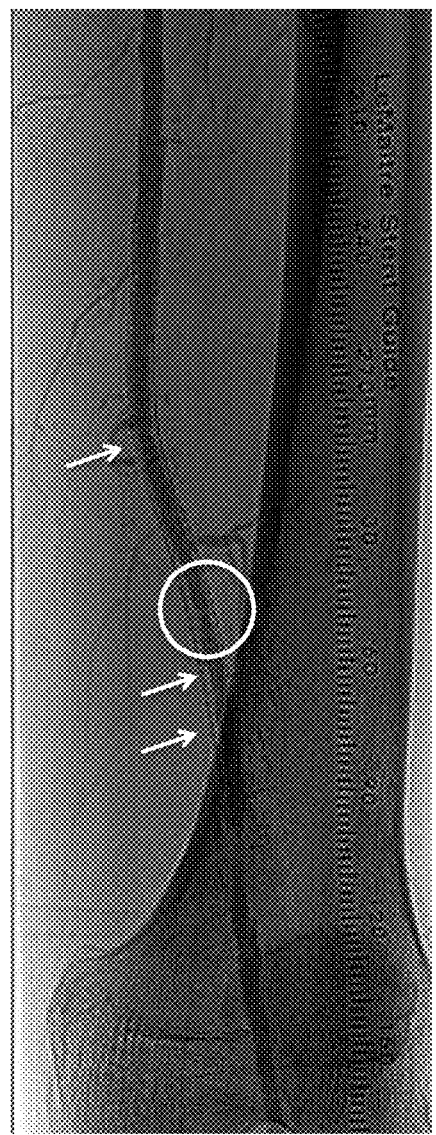
FIGS. 50A-50C show patient number 002's in-stent restenosis pre-operatively, acutely post-operative, and at 90 days post-operative, respectively.
Figure 50B:
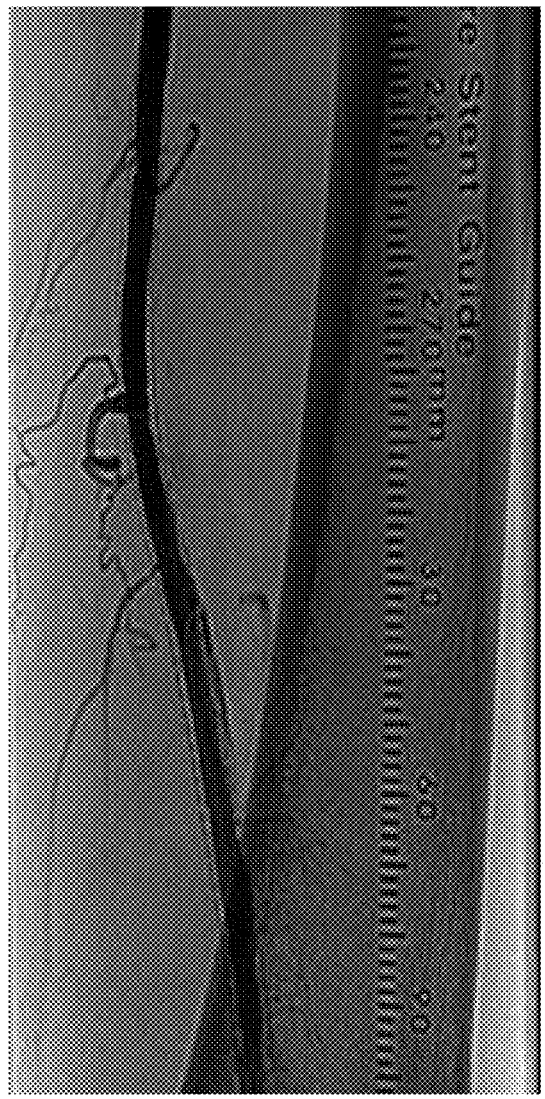
Figure 50C:

As shown in FIG. 50A, patient number 002's most stenosed section is more focal (shown inside of circled portion) than patient number 001's lesions, however, as is common for in-stent restenosis in the leg, diffuse stenosis can be observed along the full length of the 150 mm stent (shown by arrow markers). As seen in FIGS. 50B and 50C respectively, patient number 002's acute post-operative and 90-day post-operative lumen diameter is observably improved.

Figure 51A:
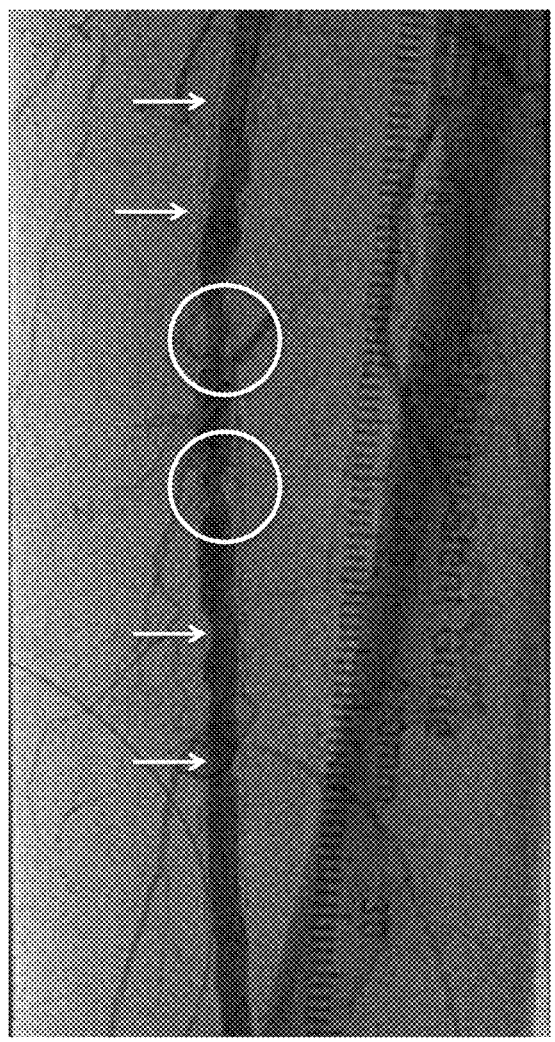
FIGS. 51A-51C show patient number 005's in-stent restenosis pre-operatively, acutely post-operative, and at 90 days post-operative, respectively.
Figure 51B:
Figure 51C:
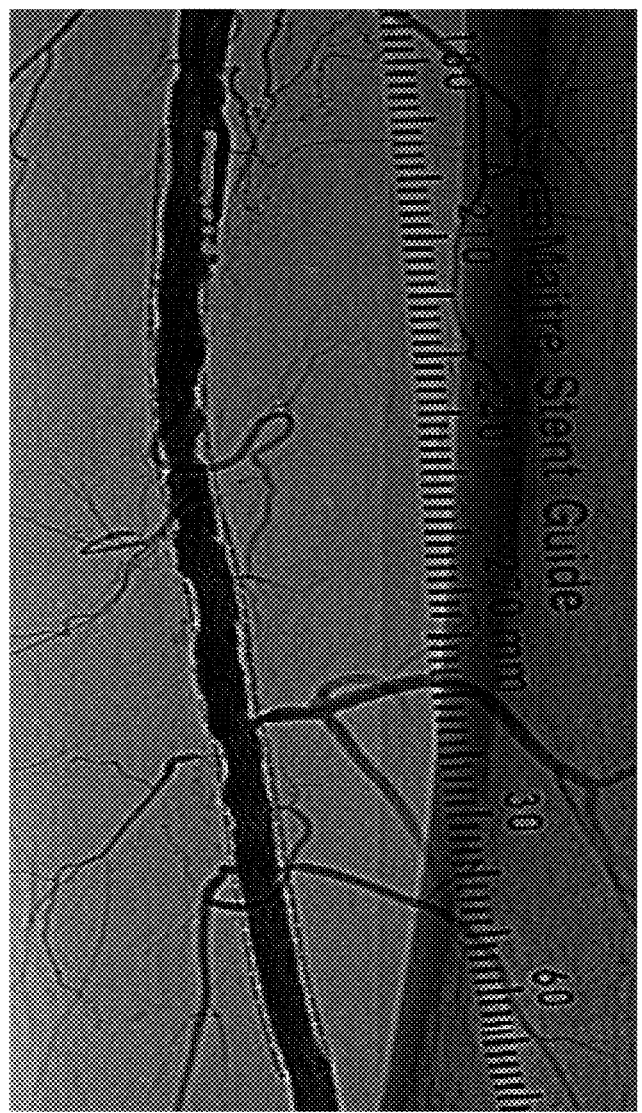

Referring to FIG. 51A, patient number 005 has two focally stenotic sections pre-operatively (shown inside of circled areas), but, similar to patient numbers 001 and 002, has diffuse stenosis throughout most of the length of the 150 mm stent (shown by arrow markers). The acute post-operative and 90-day post-operative lumen diameters shown respectively in FIGS. 51B and 51C again provide readily observable improvement of luminal patency as compared to the pre-operative condition. Table 3 reports the measured changes in stenosis acutely post-operative and at 90 days corresponding to FIGS. 49A-51C.

While the exemplary embodiments have been described in some detail, by way of example and for clarity of understanding, those of skill in the art will recognize that a variety of modifications, adaptations, and changes may be employed.

What is claimed is:

1. A system for delivering energy-based treatment for in-stent restenosis and other stenosis of the vasculature, the system comprising:
    an elongate flexible catheter body having a proximal end and a distal end with an axis therebetween;
    a radially expandable structure near the distal end of the catheter body;
    a plurality of electrodes positioned on the radially expandable structure so as to engage tissue upon expansion of the radially expandable structure, wherein the plurality of electrodes are included in one or more flex circuits, wherein the one or more flex circuits further comprise a temperature sensing structure mounted thereon adjacent to at least one of the electrodes;
    a power source coupled with the electrodes such that when an electrode engages tissue an electrical circuit comprising the power source, the electrode, and the engaged tissue is defined; and,
    a processor coupled with the power source and the temperature sensing structure, the processor configured to verify the presence of the electrical circuit, to selectively energize the engaged electrodes, and to control the delivery of energy by regulating one or more parameters of the electrical circuit based on monitoring feedback from the electrical circuit and the temperature sensing structure such that energy delivered to a tissue treatment zone heats tissue therein to a surface temperature of about 55° C. to about 75° C. while tissue collateral to the treatment zone 1 mm from the surface and deeper is heated to less than about 45° C., thereby inducing a tissue response that remodels stenosis and avoids a subsequently occluding tissue response caused by thermal damage,
    wherein the processor is configured to monitor and modify energy delivery to at least one of the plurality of electrodes by the power source in response to a change in at least one of frequency range, impedance magnitude, impedance phase angle, temperature, power, voltage, and current, the change being associated with proximity to a metallic implanted structure.

2. The system of claim 1, wherein the plurality of electrodes are distributed about the circumference of the expandable structure so as to form an electrode array, the electrodes having an elongate shape oriented to be substantially parallel to the catheter axis upon expansion of the expandable structure.

3. The system of claim 1, wherein the expandable structure comprises a balloon.

4. The system of claim 3, wherein the one or more flex circuits include a monopolar electrode or a bipolar electrode pair.

5. The system of claim 3, wherein the balloon inflation pressure is about 10 atmospheres or less.

6. The system of claim 1, wherein the electrodes include a radiopaque material.

7. The system of claim 1, wherein the processor is configured to monitor and modify energy delivery to at least one of the plurality of electrodes by the power source in response to a change in at least one of frequency range, impedance magnitude, impedance phase angle, temperature, power, voltage, and current, the change being associated with heating of tissue.

8. The system of claim 7, wherein the processor halts energy delivery to said at least one of the plurality of electrodes while optionally continuing to energize and regulate energy delivery to another electrode.

9. The system of claim 1, wherein the expanded diameter of the expandable structure is about 2 mm to about 10 mm.

10. The system of claim 1, wherein the processor is configured to characterize tissue in the treatment zone using a tissue signature profile curve, within a frequency range, of impedance magnitude and phase angles of the circuit.

11. The system of claim 10, wherein the processor is configured to characterize tissue by comparing the tissue signature profile curve to at least one other tissue signature profile curve, by selectively energizing at least one of the plurality of electrodes, so as identify at least one of tissue to be treated and an implanted structure.

12. The system of claim 11, wherein the processor is configured to selectively energize said at least one of the plurality of electrodes, and by using at least one of a relative slope of the tissue signature profile curves and an offset between the tissue signature profiles, characterize the tissue to be treated.

13. The system of claim 11, wherein energy delivery may be selected by the processor based on a determination of a composition of the implanted structure according to an impedance measurement.

14. The system of claim 10, wherein the processor is configured to localize and characterize a plurality of materials about the vasculature, and to selectively treat different characterized materials by applying different remodeling energy treatments to selected electrodes.

15. The system of claim 1, wherein the processor selectively energizes at least one of the plurality of electrodes by modulating one or more of power, duty cycle, current, and voltage based on at least one of the one or more parameters of the electrical circuit.

16. The system of claim 1, wherein the electrodes are energized in a sequence.

17. The system of claim 16, wherein a first group of electrodes is energized in a sequence so as to define a first pattern of treatment zones, and wherein a second group of electrodes is energized in a sequence so as to define a second pattern of treatment zones, so as to minimize the gap between the first and second pattern of treatment zones.

18. The system of claim 1, wherein at least one of the plurality of electrodes is energized with a power of 0.5 Watts to 20 Watts for 0.5 seconds to 180 seconds.

19. The system of claim 1, wherein the expandable structure may be expanded and collapsed so as to allow for repositioning of the catheter along a portion of the vasculature.

20. The system of claim 1, wherein the power source includes a radiofrequency generator.

21. A catheter for delivering energy-based treatment for in-stent restenosis and other stenosis of the vasculature, the system comprising:
an elongate flexible catheter body having a proximal end and a distal end with an axis therebetween;
a radially expandable structure near the distal end of the catheter body;
a plurality of electrodes positioned on the radially expandable structure so as to engage tissue at an electrode position upon expansion of the radially expandable structure, the tissue in proximity to engaged electrodes defining a tissue treatment zone, wherein the electrodes are positioned on a flex circuit; and
a temperature sensing structure mounted on the flex circuit adjacent at least one of said plurality of electrodes, the temperature sensing structure being electrically coupled to a processor so as to comprise a means of feedback for control by a power source by sensing temperature in proximity to at least one electrode, wherein the processor is configured to deliver energy to a tissue treatment zone to heat tissue therein to a surface temperature of about 55° C. to about 75° C. while tissue collateral to the treatment zone 1 mm from the surface and deeper is heated to less than about 45° C., thereby inducing a tissue response that remodels stenosis and avoids a subsequently occluding tissue response caused by thermal damage,
wherein the processor is configured to monitor and modify energy delivery to at least one of the plurality of electrodes by the power source in response to a change in at least one of frequency range, impedance magnitude, impedance phase angle, temperature, power, voltage, and current, the change being associated with proximity to a metallic implanted structure.

22. The catheter of claim 21, wherein the plurality of electrodes are distributed about the circumference of the expandable structure so as to form an electrode array, the electrodes having an elongate shape oriented to be substantially parallel to the catheter axis upon expansion of the expandable structure.

23. The catheter of claim 21, wherein the expandable structure comprises a balloon.

24. The catheter of claim 23, wherein the circuit includes a monopolar electrode or a bipolar electrode pair.

25. The catheter of claim 23, wherein the balloon inflation pressure is about 10 atmospheres or less.

26. The catheter of claim 21, wherein the electrodes are comprised of a radiopaque material.

27. The catheter of claim 21, wherein the expanded diameter of the expandable structure is about 2 mm to about 10 mm.

28. The catheter of claim 21, wherein the expandable structure may be expanded and collapsed so as to allow for repositioning of the catheter along a portion of the vasculature.

29. A system for delivering energy-based treatment for in-stent restenosis and other stenosis of the vasculature, the system comprising:
an elongate flexible catheter body having a proximal end, a distal end, and a longitudinal axis extending therebetween;
a radially expandable structure disposed on the catheter body near the distal end thereof;
a plurality of electrodes positioned on the radially expandable structure so as to engage a tissue upon expansion of the radially expandable structure, the tissue in proximity to engaged electrodes defining a tissue treatment zone, wherein the plurality of electrodes are included in one or more flex circuits, wherein the one or more flex circuits further comprise a temperature sensing structure mounted thereon adjacent to at least one of the electrodes;
a power source coupled with the electrodes such that when an electrode of the plurality engages the tissue, an electrical circuit comprising the power source, the engaged electrode, and the tissue engaged by the electrode can be defined; and a processor coupled with the power source and the temperature sensing structure, the processor configured to control the delivery of energy by regulating one or more parameters of the electrical circuit based on monitoring feedback acquired from the electrical circuit and the temperature sensing structure such that the controlled delivery of energy heats the tissue to be treated to a surface temperature of about 55° C. to about 75° C. while a collateral tissue adjacent the treatment zone 1 mm from the surface and deeper is heated to less than about 45° C. thereby inducing a tissue response that remodels stenosis and avoids a subsequently occluding tissue response caused by thermal damage,
wherein the processor is configured to monitor and modify energy delivery to at least one of the plurality of electrodes by the power source in response to a change in at least one of frequency range, impedance magnitude, impedance phase angle, temperature, power, voltage, and current, the change being associated with proximity to a metallic implanted structure.

* * * * *